US008647574B2

(12) United States Patent
Halverson et al.

(10) Patent No.: US 8,647,574 B2
(45) Date of Patent: *Feb. 11, 2014

(54) SAMPLE PREPARATION CONTAINER AND METHOD

(75) Inventors: Kurt J. Halverson, Lake Elmo, MN (US); Stephen C. P. Joseph, Woodbury, MN (US); Raj Rajagopal, Woodbury, MN (US); David J. Velasquez, Cannon Falls, MN (US); Cynthia D. Zook, Hudson, WI (US); Sailaja Chandrapati, Woodbury, MN (US); Daniel E. Siltberg, White Bear Township, MN (US); Paul J. Cobian, Woodbury, MN (US); Theresa J. Gerten, Inver Grove Heights, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 367 days.

This patent is subject to a terminal disclaimer.

(21) Appl. No.: 12/743,252
(22) PCT Filed: Nov. 19, 2008
(86) PCT No.: PCT/US2008/084007
§ 371 (c)(1),
(2), (4) Date: May 17, 2010
(87) PCT Pub. No.: WO2009/067498
PCT Pub. Date: May 28, 2009

(65) Prior Publication Data
US 2010/0255484 A1 Oct. 7, 2010

Related U.S. Application Data
(60) Provisional application No. 60/989,170, filed on Nov. 20, 2007.

(51) Int. Cl.
*G01N 15/06* (2006.01)
(52) U.S. Cl.
USPC ............ 422/68.1; 422/50; 436/174; 436/178; 436/180; 436/807; 436/810; 210/516

(58) Field of Classification Search
USPC ........... 422/50, 68.1; 436/174, 177, 178, 180, 436/807, 810; 210/516
See application file for complete search history.

(56) References Cited

U.S. PATENT DOCUMENTS

| | | |
|---|---|---|
| 3,163,160 A | 12/1964 | Cohen |
| 3,367,191 A | 2/1968 | Richard |

(Continued)

FOREIGN PATENT DOCUMENTS

| | | |
|---|---|---|
| BE | 849898 | 6/1977 |
| EP | 0175326 | 3/1986 |

(Continued)

OTHER PUBLICATIONS

Andrews, W. H, et al., "Food Sampling and Preparation of Sample Homogenate," Bacteriological Analytical manual Online, U.S. Food and Drug Admin., Center for Food Safety & Applied Nutrition,[Retrieved from the internet Apr. 7, 2006] pp. 1-10, http://www.cfsan.fda.gov/~ebam/bam-1.html.

(Continued)

*Primary Examiner* — Melanie Y Brown
(74) *Attorney, Agent, or Firm* — Nicole J. Einerson

(57) ABSTRACT

A system and method for preparing and collecting samples for analyte testing. The system can include a sample preparation system and a sample collection system coupled to the sample preparation system. The sample preparation system can include at least one of a deformable self-supporting receptacle comprising a reservoir and a freestanding receptacle comprising a reservoir. The reservoir can be adapted to contain a liquid composition. The sample collection system can be positioned in fluid communication with a reservoir of the sample preparation system, and can be adapted to capture an analyte of interest. The method can include providing a fluid path defined at least partially by the sample preparation system and the sample collection system, positioning the liquid composition in a reservoir of the sample preparation system, and moving at least a portion of the liquid composition in the fluid path to the sample collection system.

24 Claims, 13 Drawing Sheets

(56) References Cited

U.S. PATENT DOCUMENTS

| | | |
|---|---|---|
| 3,449,081 A | 6/1969 | Hughes |
| 3,601,317 A | 8/1971 | Genantonio |
| 3,748,905 A | 7/1973 | Fletcher et al. |
| 3,784,039 A | 1/1974 | Marco |
| 3,819,158 A | 6/1974 | Sharpe et al. |
| 4,121,306 A | 10/1978 | Bringman |
| 4,427,406 A | 1/1984 | Nielsen |
| 4,937,194 A | 6/1990 | Pattillo et al. |
| 4,984,715 A | 1/1991 | Green |
| 5,100,801 A | 3/1992 | Ward, Jr. et al. |
| 5,119,830 A | 6/1992 | Davis |
| 5,186,897 A | 2/1993 | Eason et al. |
| 5,230,865 A | 7/1993 | Hargett |
| 5,291,779 A | 3/1994 | Govoni |
| 5,341,693 A | 8/1994 | Banu |
| 5,350,080 A | 9/1994 | Brown et al. |
| 5,385,251 A | 1/1995 | Dunn |
| 5,403,551 A | 4/1995 | Galloway et al. |
| 5,403,745 A | 4/1995 | Ollington |
| 5,543,115 A * | 8/1996 | Karakawa ............ 422/535 |
| 5,569,225 A | 10/1996 | Fleury |
| 5,617,972 A | 4/1997 | Morano et al. |
| 5,728,542 A | 3/1998 | Charm et al. |
| 5,728,587 A * | 3/1998 | Kang et al. ............ 436/518 |
| 5,806,711 A | 9/1998 | Morano et al. |
| 5,833,860 A | 11/1998 | Kopaciewicz et al. |
| 5,849,505 A | 12/1998 | Guirguis |
| 6,021,681 A | 2/2000 | Jezek |
| 6,107,085 A | 8/2000 | Coughlin et al. |
| 6,168,758 B1 * | 1/2001 | Forsberg et al. ............ 422/412 |
| 6,180,335 B1 | 1/2001 | Wilkins et al. |
| 6,187,209 B1 * | 2/2001 | Shurtliff et al. ............ 210/808 |
| 6,221,655 B1 | 4/2001 | Fung et al. |
| 6,273,600 B1 | 8/2001 | Sharpe et al. |
| 6,303,363 B1 | 10/2001 | Ward |
| 6,338,569 B1 | 1/2002 | McGill |
| 6,458,067 B1 | 10/2002 | Dorin |
| 6,461,853 B1 | 10/2002 | Zhu |
| 6,471,069 B2 | 10/2002 | Lin |
| 6,516,953 B1 | 2/2003 | DiCesare |
| 6,536,687 B1 | 3/2003 | Navis et al. |
| 6,541,262 B1 | 4/2003 | Baugh |
| 6,576,193 B1 | 6/2003 | Cui et al. |
| 6,588,681 B2 | 7/2003 | Rothrum et al. |
| 6,595,441 B2 | 7/2003 | Petrie et al. |
| 6,599,420 B2 | 7/2003 | Sugiyama et al. |
| 6,669,908 B2 | 12/2003 | Weyker et al. |
| 6,746,601 B2 | 6/2004 | Dorin |
| 6,789,945 B2 | 9/2004 | Mobs et al. |
| 6,820,824 B1 | 11/2004 | Joesph et al. |
| 6,854,875 B2 | 2/2005 | McGill |
| 6,955,099 B2 | 10/2005 | Goodin |
| 7,022,289 B1 | 4/2006 | Schlein et al. |
| 7,100,461 B2 | 9/2006 | Bradley et al. |
| 7,108,662 B2 | 9/2006 | Miller et al. |
| D532,253 S | 11/2006 | White |
| 7,147,365 B2 | 12/2006 | McGill |
| 7,168,845 B2 | 1/2007 | McGill |
| 7,188,785 B2 | 3/2007 | Joseph et al. |
| 7,211,225 B2 | 5/2007 | Ferguson et al. |
| 7,223,364 B1 | 5/2007 | Johnston et al. |
| 7,309,156 B2 | 12/2007 | McGill |
| 7,374,111 B2 | 5/2008 | Joseph et al. |
| 7,555,965 B1 | 7/2009 | Mayeaux |
| 2001/0031491 A1 | 10/2001 | Curtis |
| 2002/0000403 A1 * | 1/2002 | Tanaka et al. ............ 210/263 |
| 2002/0015355 A1 | 2/2002 | Sanpei et al. |
| 2002/0042145 A1 | 4/2002 | Forsberg |
| 2002/0078766 A1 * | 6/2002 | Diaz ............ 73/863.86 |
| 2002/0085957 A1 | 7/2002 | Moore |
| 2002/0094548 A1 * | 7/2002 | Feistel ............ 435/7.92 |
| 2002/0127307 A1 | 9/2002 | McGill |
| 2002/0127630 A1 | 9/2002 | DiGuiseppi et al. |
| 2004/0014237 A1 | 1/2004 | Sugiyama |
| 2004/0015786 A1 | 1/2004 | Pugliese |
| 2004/0038425 A1 | 2/2004 | Ferguson |
| 2004/0072367 A1 | 4/2004 | Ding |
| 2004/0114457 A1 | 6/2004 | McGill |
| 2004/0140373 A1 | 7/2004 | Joesph et al. |
| 2004/0164182 A1 | 8/2004 | Joseph et al. |
| 2004/0237674 A1 | 12/2004 | Wu et al. |
| 2004/0256484 A1 | 12/2004 | Joseph et al. |
| 2004/0256485 A1 | 12/2004 | Joseph et al. |
| 2005/0023182 A1 | 2/2005 | Shah |
| 2005/0112024 A1 | 5/2005 | Guo et al. |
| 2005/0132775 A1 | 6/2005 | Laugharn, Jr. et al. |
| 2005/0244943 A1 | 11/2005 | Ladisch et al. |
| 2006/0039742 A1 | 2/2006 | Cable |
| 2006/0073538 A1 | 4/2006 | Konrad |
| 2006/0102550 A1 | 5/2006 | Joseph et al. |
| 2006/0151630 A1 | 7/2006 | Joseph et al. |
| 2006/0240458 A1 | 10/2006 | Steichen et al. |
| 2006/0275798 A1 | 12/2006 | Steichen et al. |
| 2007/0084736 A1 | 4/2007 | Igota et al. |
| 2007/0269341 A1 | 11/2007 | Halverson |
| 2007/0297698 A1 | 12/2007 | Berich |
| 2008/0054087 A1 | 3/2008 | Joseph et al. |
| 2008/0268446 A1 | 10/2008 | Steichen et al. |
| 2009/0005747 A1 | 1/2009 | Michaels |
| 2009/0193880 A1 | 8/2009 | Halverson et al. |

FOREIGN PATENT DOCUMENTS

| | | |
|---|---|---|
| EP | 0471947 | 2/1992 |
| EP | 1005909 | 6/2000 |
| GB | 2298272 | 8/1996 |
| JP | 61-73054 | 4/1986 |
| JP | 7-223651 | 8/1995 |
| JP | 2004-501761 | 1/2004 |
| WO | WO 86/00704 | 1/1986 |
| WO | WO 94/14068 | 6/1994 |
| WO | WO 98/07828 | 2/1998 |
| WO | WO 98/32534 | 7/1998 |
| WO | WO 98/32539 | 7/1998 |
| WO | WO 00/15328 | 3/2000 |
| WO | WO 00/42419 | 7/2000 |
| WO | WO 02/06791 | 1/2002 |
| WO | WO 03/092573 | 11/2003 |
| WO | WO 2004/031734 | 4/2004 |
| WO | WO 2004/037433 | 5/2004 |
| WO | WO 2004/060574 | 7/2004 |
| WO | WO 2004/060575 | 7/2004 |
| WO | WO 2004/094072 | 11/2004 |
| WO | WO 2004/105949 | 12/2004 |
| WO | WO 2006/037140 | 4/2006 |
| WO | WO 2006/107843 | 10/2006 |
| WO | WO 2007/016691 | 2/2007 |
| WO | WO 2007/062263 | 5/2007 |
| WO | WO 2007/079143 | 7/2007 |
| WO | WO 2007/079188 | 7/2007 |
| WO | WO 2007/137257 | 11/2007 |
| WO | WO 2009/067503 | 5/2009 |
| WO | WO 2009/067513 | 5/2009 |
| WO | WO 2009/067518 | 5/2009 |
| WO | WO 2010/080223 | 7/2010 |

OTHER PUBLICATIONS

Andrews, W.H., et al., "Usefullness of the Stomacher in a Microbiological Regulatory Laboratory," Applied and Environmental Microbiology, Jan. 1978, vol. 35, No. 1, pp. 89-93.

Fung, D.Y.C. et al., "The Pulsifier: A New Instrument for Preparing Food Suspensions for Microbiological Analysis," Journal of Rapid Methods and Automation Microbiology 6, Jun. 20, 1997, pp. 43-49.

Ingham, Steven C. et al., "Manual Shaking as an Alternative to Mechanical Stomaching in Preparing Ground Meats for Microbiological analysis," Food Protection Trends, Apr. 2004, vol. 24 No. 4, pp. 253-256.

Sharpe, A.N. et al., "Stomaching: A New Concept in Bactheriological Sample Preparation," Applied Microbiology, Aug. 1972, vol. 24, No. 2, pp. 175-178.

(56) References Cited

OTHER PUBLICATIONS

Wu, Vivian, C.H., et al., "Comparison of the Pulsifier and the Stomacher for Recovering Microorganisms in Vegetables," Journal of Rapid Methods and Automation Microbiology 11, Sep. 22, 2003, pp. 145-152, Food & Nutrition Press, Inc., Trumbull, USA.

Sharpe, et al. Ultrasound and Vortex Stirring as Bacteriological Sampling Methods for Foods, Fournal of Applied Bacteriology, 33 (1970), p. 351-357.

International Search Report PCT/US2008/084007, Feb. 24, 2009, 4 pgs.

* cited by examiner

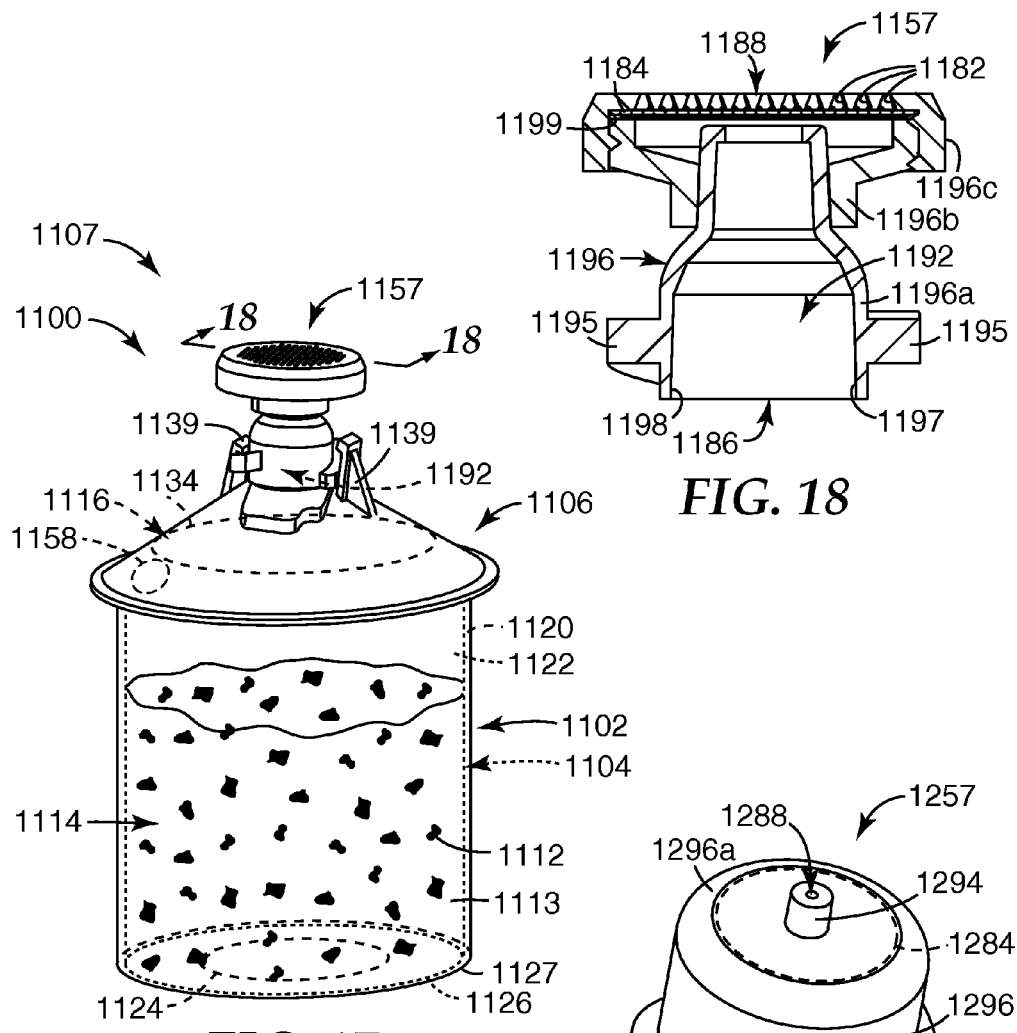
FIG. 17
FIG. 18
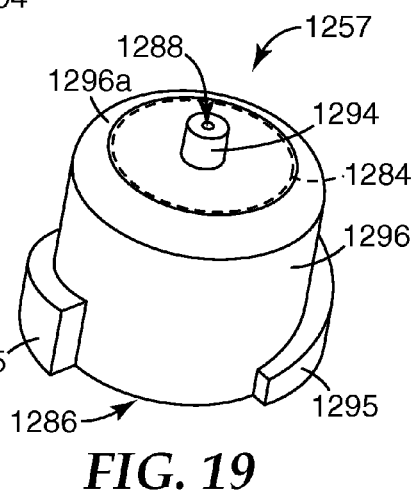
FIG. 19
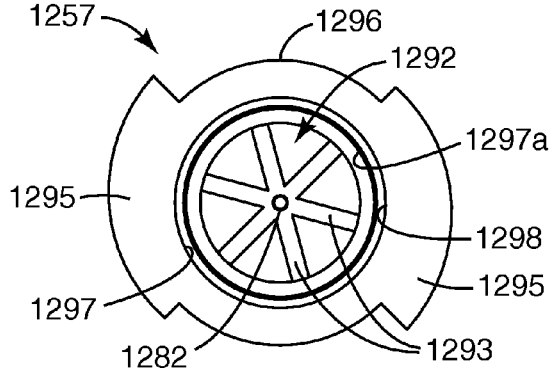
FIG. 20

SAMPLE PREPARATION CONTAINER AND METHOD

CROSS REFERENCE TO RELATED APPLICATIONS

This application is a national stage filing under 35 U.S.C. 371 of PCT/US2008/084007, filed Nov. 19, 2008, which claims priority to U.S. Provisional Application No. 60/989,170, filed Nov. 20, 2007, the disclosure of which is incorporated by reference in its entirety herein.

BACKGROUND

In a variety of applications, food and non-food sources may need to be tested for microorganisms (e.g., bacteria, viruses, fungi, spores, etc.) and/or other analytes of interest (e.g., toxins, allergens, hormones, etc.). For example, foods grown, purchased and consumed by the general population may contain or acquire microorganisms or other analytes, which can flourish or grow as a function of the environment in which they are located. This growth may lead to accelerated spoilage of the food product or to the proliferation of pathogenic organisms, which may produce toxins or multiply to infective doses. By way of further example, a variety of analytical methods can be performed on samples of non-food sources (e.g., groundwater, urine, etc.) to determine if the sample contains a particular analyte. For example, groundwater can be tested for a microorganism or a chemical toxin; and urine can be tested for a variety of diagnostic indicators to enable a diagnosis (e.g., diabetes, pregnancy, etc.).

SUMMARY

The present disclosure relates to a sample preparation and collection system and method, and particularly, to a sample preparation and collection system and method for analyte testing, the sample preparation and collection system comprising a sample preparation system and a sample collection system coupled to the sample preparation system that captures or collects an analyte of interest from a liquid composition, a filtrate thereof, or a sample taken from the liquid composition or the filtrate.

Some embodiments of the present disclosure provide a system for preparing and collecting samples for analyte testing. The system can include a sample preparation system comprising, and a sample collection system coupled to the sample preparation system. The sample preparation system can include a deformable self-supporting receptacle comprising a reservoir, and the reservoir can be adapted to contain a liquid composition comprising a source and a diluent. The sample collection system can be positioned in fluid communication with the reservoir of the sample preparation system, and the sample collection system can be adapted to capture an analyte of interest from the liquid composition.

Some embodiments of the present disclosure provide a system for preparing and collecting samples for analyte testing. The system can include a sample preparation system and a sample collection system coupled to the sample preparation system. The sample preparation system can include a freestanding receptacle comprising a reservoir, and the reservoir can be adapted to contain a liquid composition comprising a source and a diluent. The sample collection system can be positioned in fluid communication with the reservoir of the sample preparation system, and the sample collection system can be adapted to capture an analyte of interest from the liquid composition.

Some embodiments of the present disclosure provide a system for preparing and collecting samples for analyte testing. The system can include a sample preparation system and a sample collection system coupled to the sample preparation system. The sample preparation system can include a freestanding container comprising a first reservoir, a deformable self-supporting receptacle dimensioned to be received in the first reservoir of the freestanding container and comprising a second reservoir, and a lid adapted to be coupled to at least one of the freestanding container and the deformable self-supporting receptacle. The second reservoir can be adapted to contain a liquid composition comprising a source and a diluent. The sample collection system coupled can be positioned in fluid communication with the second reservoir of the sample preparation system, and the sample collection system can be adapted to capture an analyte of interest from the liquid composition.

Some embodiments of the present disclosure provide a method for preparing and collecting samples for analyte testing. The method can include providing a sample preparation system comprising a freestanding receptacle comprising a reservoir, and providing a sample collection system coupled to the sample preparation system. The sample collection system can be positioned in fluid communication with the reservoir of the freestanding receptacle, and the sample collection system can be adapted to capture an analyte of interest. The method can further include providing a liquid composition comprising a source and a diluent, and providing a fluid path defined at least partially by the sample preparation system and the sample collection system. The method can further include positioning the liquid composition in the reservoir of the freestanding receptacle, and moving at least a portion of the liquid composition in the fluid path to the sample collection system.

Some embodiments of the present disclosure provide a method for preparing and collecting samples for analyte testing. The method can include providing a sample preparation system comprising a deformable self-supporting receptacle comprising a reservoir, and providing a sample collection system coupled to the sample preparation system. The sample collection system can be positioned in fluid communication with the reservoir of the deformable self-supporting receptacle, and the sample collection system can be adapted to capture an analyte of interest. The method can further include providing a liquid composition comprising a source and a diluent, and providing a fluid path defined at least partially by the sample preparation system and the sample collection system. The method can further include positioning the liquid composition in the reservoir of the deformable self-supporting receptacle, and moving at least a portion of the liquid composition in the fluid path to the sample collection system.

Other features and aspects of the invention will become apparent by consideration of the detailed description and accompanying drawings.

BRIEF DESCRIPTION OF THE DRAWINGS

FIG. 17 is a perspective view of a sample preparation and collection system according to another embodiment of the present disclosure, the sample preparation and collection system including a sample collection system.

FIG. 18 is a cross-sectional side view of the sample collection system of FIG. 17, taken along line 18-18 in FIG. 17.

FIG. 19 is a perspective view of a sample collection system according to another embodiment of the present disclosure.

FIG. 20 is a bottom view of the sample collection system of FIG. 19.

DETAILED DESCRIPTION

Figure 1:
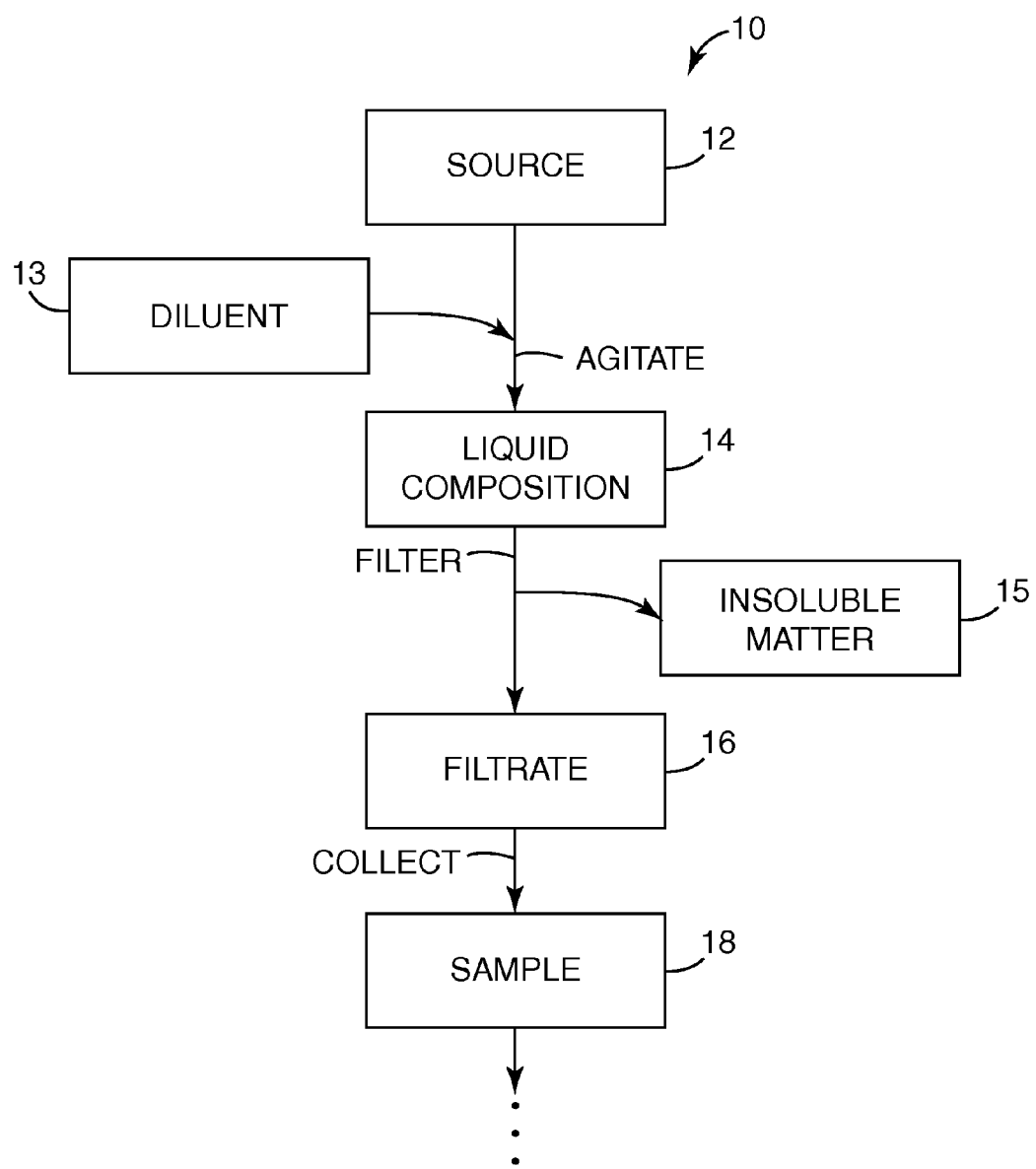
FIG. 1 is a schematic flow chart depicting a sample preparation and collection method according to one embodiment of the present disclosure.

Before any embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways. Also, it is to be understood that the phraseology and terminology used herein is for the purpose of description and should not be regarded as limiting. The use of "including," "comprising," "containing," or "having" and variations thereof herein is meant to encompass the items listed thereafter and equivalents thereof as well as additional items. Unless specified or limited otherwise, the terms "supported," and "coupled" and variations thereof are used broadly and encompass both direct and indirect supports and couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure is generally directed to a system and method for preparing and collecting samples. The collected samples can be further concentrated, enriched, and/or analyzed for the presence or absence of a variety of analytes.

The term "source" is generally used to refer to the food or nonfood desired to be tested for analytes. The source can be a solid, a liquid, a semi-solid, a gelatinous material, and combinations thereof. In some embodiments, the source can be provided by a substrate that was used, for example, to collect the source from a surface of interest. In some embodiments, the liquid composition can include the substrate, which can be further broken apart (e.g., during an agitation or dissolution process) to enhance retrieval of the source and any analyte of interest. The surface of interest can include at least a portion of a variety of surfaces, including, but not limited to, walls (including doors), floors, ceilings, drains, refrigeration systems, ducts (e.g., airducts), vents, toilet seats, handles, doorknobs, handrails, bedrails (e.g., in a hospital), countertops, tabletops, eating surfaces (e.g., trays, dishes, etc.), working surfaces, equipment surfaces, clothing, etc., and combinations thereof. All or a portion of the source can be used in the sample preparation system and method. When a portion of the source is used, this can sometimes be referred to as a "sample" of the source. However, the term "sample" is generally used herein to refer to a volume or mass of material that is extracted from the sample preparation system for further analysis (e.g., detection of analytes).

The term "food" is generally used to refer to a solid, liquid (e.g., including, but not limited to, solutions, dispersions, emulsions, suspensions, etc., and combinations thereof) and/or semi-solid comestible composition. Examples of foods include, but are not limited to, meats, poultry, eggs, fish, seafood, vegetables, fruits, prepared foods (e.g., soups, sauces, pastes), grain products (e.g., flour, cereals, breads), canned foods, milk, other dairy products (e.g., cheese, yogurt, sour cream), fats, oils, desserts, condiments, spices, pastas, beverages, water, animal feed, other suitable comestible materials, and combinations thereof.

The term "nonfood" is generally used to refer to sources of interest that do not fall within the definition of "food" and are generally not considered to be comestible. Examples of nonfood sources can include, but are not limited to, clinical samples, cell lysates, whole blood or a portion thereof (e.g., serum), other bodily fluids or secretions (e.g., saliva, sweat, sebum, urine), feces, cells, tissues, organs, biopsies, plant materials, wood, soil, sediment, medicines, cosmetics, dietary supplements (e.g., ginseng capsules), pharmaceuticals, fomites, other suitable non-comestible materials, and combinations thereof.

The term "fomite" is generally used to refer to an inanimate object or substrate capable of carrying infectious organisms and/or transferring them. Fomites can include, but are not limited to, cloths, mop heads, towels, sponges, wipes, eating utensils, coins, paper money, cell phones, clothing (including shoes), doorknobs, feminine products, diapers, etc., portions thereof, and combinations thereof.

The term "analyte" is generally used to refer to a substance to be detected (e.g., by a laboratory or field test). A source can be tested for the presence or absence of particular analytes or for quantitation of particular analytes. Such analytes can be present within a source (e.g., on the interior), or on the exterior (e.g., on the outer surface) of a source. Examples of analytes can include, but are not limited to, microorganisms, parasites (some of which are also microorganisms), biomolecules, chemicals (e.g. pesticides, antibiotics), metal ions (e.g. mercury ions, heavy metal ions), metal-ion-containing complexes (e.g., complexes comprising metal ions and organic ligands), and combinations thereof.

A variety of testing methods can be used to identify and/or quantitate an analyte, including, but not limited to, microbiological assays, biochemical assays (e.g. immunoassay), or a combination thereof. Specific examples of testing methods that can be used include, but are not limited to, lateral flow assays, titration, thermal analysis, microscopy (e.g., light microscopy, fluorescent microscopy, immunofluorescent microscopy, scanning electron microscopy (SEM), transmission electron microscopy (TEM)), spectroscopy (e.g., mass spectroscopy, nuclear magnetic resonance (NMR) spectroscopy, Raman spectroscopy, infrared (IR) spectroscopy, x-ray spectroscopy, attenuated total reflectance spectroscopy, Fourier transform spectroscopy, gamma-ray spectroscopy, etc.), spectrophotometry (e.g., absorbance, fluorescence, luminescence, etc.), chromatography (e.g., gas chromatography, liquid chromatography, ion-exchange chromatography, affinity chromatography, etc.), electrochemical analysis, genetic techniques (e.g., polymerase chain reaction (PCR), transcription mediated amplification (TMA), hybridization protection assay (HPA), DNA or RNA molecular recognition assays, etc.), adenosine triphosphate (ATP) detection assays, immunological assays (e.g., enzyme-linked immunosorbent assay (ELISA)), cytotoxicity assays, viral plaque assays, techniques for evaluating cytopathic effect, culture techniques such as those that can be done using a growth medium (e.g., agar) and/or 3M™ Petrifilm™ Plates (e.g., and imaged, quantified and/or interpreted using a 3M™ Petrifilm™ Plate Reader (3M Company, St. Paul, Minn.)), other suitable analyte testing methods, or a combination thereof.

The term "microorganism" is generally used to refer to any prokaryotic or eukaryotic microscopic organism, including without limitation, one or more bacteria (e.g., motile or vegetative, Gram positive or Gram negative), viruses (e.g., Norovirus, Norwalk virus, Rotavirus, Adenovirus, DNA viruses, RNA viruses, enveloped, non-enveloped, human immunodeficiency virus (HIV), human Papillomavirus (HPV), etc.), bacterial spores or endospores, algae, fungi (e.g., yeast, filamentous fungi, fungal spores), prions, mycoplasmas, and protozoa. In some cases, the microorganisms of particular interest are those that are pathogenic, and the term "pathogen" is used to refer to any pathogenic microorganism. Examples of pathogens can include, but are not limited to, members of the family Enterobacteriaceae, or members of the family Micrococaceae, or the genera *Staphylococcus* spp., *Streptococcus*, spp., *Pseudomonas* spp., *Enterococcus* spp., *Salmonella* spp., *Legionella* spp., *Shigella* spp., *Yersinia* spp., *Enterobacter* spp., *Escherichia* spp., *Bacillus* spp., *Listeria* spp., *Campylobacter* spp., *Acinetobacter* spp., *Vibrio* spp., *Clostridium* spp., and *Corynebacteria* spp. Particular examples of pathogens can include, but are not limited to, *Escherichia coli* including enterohemorrhagic *E. coli* e.g., serotype O157:H7, *Pseudomonas aeruginosa, Bacillus cereus, Bacillus anthracis, Salmonella enteritidis, Salmonella typhimurium, Listeria monocytogenes, Clostridium botulinum, Clostridium perfringens, Staphylococcus aureus*, methicillin-resistant *Staphylococcus aureus, Campylobacter jejuni, Yersinia enterocolitica, Vibrio vulnificus, Clostridium difficile*, vancomycin-resistant *Enterococcus*, and *Enterobacter sakazakii*. Environmental factors that may affect the growth of a microorganism can include the presence or absence of nutrients, pH, moisture content, oxidation-reduction potential, antimicrobial compounds, temperature, atmospheric gas composition and biological structures or barriers.

The term "parasite" is generally used to refer to an organism that lives in (i.e., an endoparasite) or on (i.e., an ectoparasite) a second organism (i.e., a host), and typically causes the second organism harm. Parasites can include, but are not limited to, microorganisms, and worms (e.g., roundworms, threadworms, hookworms, macroscopic multicellular worms, pinworms, whipworms, etc.). Specific examples of parasites can include, but are not limited to, *Cryptosporidium* spp., *Giardia* spp., *Blastocystis hominis, Endolimax nana, Cryptosporidium parvum, Entamoeba histolytica, Entamoeba coli, Entamoeba hartmanni, Giardia lamblia, Chilomastix mesnili, Cyclospora cayetanensis, Helminths* (macroscopic multicellular worms), *Ascaris lumbricoides* (human roundworm), *Strongyloides stercoralis* (threadworm), *Ancylostoma duodenale* (hookworm), *Necator americanus* (hookworm), *Enterobius vermicularis* (pinworm), and *Trichuris trichiura* (whipworm).

The term "biomolecule" is generally used to refer to a molecule, or a derivative thereof, that occurs in or is formed by an organism. For example, a biomolecule can include, but is not limited to, at least one of an amino acid, a nucleic acid, a polypeptide, a protein, a polynucleotide, a lipid, a phospholipid, a saccharide, a polysaccharide, and combinations thereof. Specific examples of biomolecules can include, but are not limited to, a metabolite (e.g., staphylococcal enterotoxin), an allergen (e.g., peanut allergen(s), egg allergen(s), pollens, dust mites, molds, danders, or proteins inherent therein, etc.), a hormone, a toxin (e.g., *Bacillus* diarrheal toxin, aflatoxin, *Clostridium difficile* toxin etc.), RNA (e.g., mRNA, total RNA, tRNA, etc.), DNA (e.g., plasmid DNA, plant DNA, etc.), a tagged protein, an antibody, an antigen, ATP, and combinations thereof.

The terms "soluble matter" and "insoluble matter" are generally used to refer to matter that is relatively soluble or insoluble in a given medium, under certain conditions. Specifically, under a given set of conditions, "soluble matter" is matter that goes into solution and can be dissolved in the solvent (e.g., diluent) of a system. "Insoluble matter" is matter that, under a given set of conditions, does not go into solution and is not dissolved in the solvent of a system. A source can include soluble matter and insoluble matter (e.g., cell debris). Insoluble matter is sometimes referred to as particulate(s) or debris and can include portions of the source material itself (i.e., from internal portions or external portions (e.g., the outer surface) of the source) or other source residue or debris resulting from an agitation process. The analyte of interest can be present in the soluble matter or the insoluble matter.

The term "agitate" and derivatives thereof is generally used to describe the process of giving motion to a liquid composition, for example, to mix or blend the contents of such liquid composition, or to liquefy a solid source by blending with a liquid. A variety of agitation methods can be used, including, but not limited to, manual shaking, mechanical shaking (e.g., linear shaking), ultrasonic vibration, vortex stirring, manual stirring, mechanical stirring (e.g., by a mechanical propeller, a magnetic stirbar, or another agitating aid, such as ball bearings), manual beating, mechanical beating, blending, kneading, and combinations thereof.

The term "filtering" is generally used to describe the process of separating matter by size, charge and/or function. For example, filtering can include separating soluble matter and a solvent (e.g., diluent) from insoluble matter, or it can include separating soluble matter, a solvent and relatively small insoluble matter from relatively large insoluble matter. A variety of filtration methods can be used, including, but not limited to, passing the liquid composition through a filter, settling followed by aspiration or decanting, other suitable filtration methods, and combinations thereof "Settling" is used to refer to allowing the insoluble matter in the liquid composition to settle. Settling may occur by gravity or by centrifugation. The insoluble matter (or relatively large insoluble matter) can then be separated from the soluble matter (or soluble matter and relatively small insoluble matter) and solvent by aspirating the soluble matter and solvent from the insoluble matter, decanting the soluble matter and solvent, or a combination thereof.

A "filter" is generally used to describe the device used to separate the soluble matter (or soluble matter and relatively small insoluble matter) and solvent from the insoluble matter (or relatively large insoluble matter) in a liquid composition. Examples of filters can include, but are not limited to, a woven or non-woven mesh (e.g., a wire mesh, a cloth mesh, a plastic mesh, etc.), a woven or non-woven polymeric web (e.g., comprising polymeric fibers laid down in a uniform or non-uniform process, which can be calendered), a surface filter, a depth filter, a membrane (e.g., a ceramic membrane (e.g., ceramic aluminum oxide membrane filters available under the trade designation ANOPORE from Whatman Inc., Florham Park, N.J.), a polycarbonate membrane (e.g., track-etched polycarbonate membrane filters available under the trade designation NUCLEOPORE from Whatman, Inc.)), a polyester membrane (e.g., comprising track-etched polyester, etc.), a sieve, glass wool, a frit, filter paper, foam, etc., and combinations thereof.

The term "filtrate" is generally used to describe the liquid remaining after the insoluble matter (or at least the relatively large insoluble matter) has been removed from the liquid composition. Because filtering includes a broad range of methods, the term "filtrate" can also be used to refer to the supernatant that results from allowing insoluble matter (or relatively large insoluble matter) in a mixture to settle.

FIG. 1 illustrates a sample preparation and collection method 10 according to one embodiment of the present disclosure. As shown in FIG. 1, the sample preparation and collection method 10 can begin with obtaining a source 12. A diluent 13 can be combined with all or a portion of the source 12 and agitated to form a liquid composition 14 comprising the source 12 dissolved, dispersed, suspended and/or emulsified in the diluent 13. As such, the liquid composition 14 is generally a mixture, and can be a solution, an emulsion, a dispersion, a suspension, or a combination thereof.

The source 12, when combined with the diluent 13, can include soluble matter and insoluble matter 15, such that some portions of the source 12 can be dissolved in the diluent 13, while other portions of the source 12 are suspended, dispersed or emulsified in the diluent 13. The liquid composition 14 is then filtered to form a filtrate 16 that comprises the analyte of interest (if present). The analyte of interest can be present in the soluble matter or the insoluble matter of the liquid composition 14. If the analyte of interest is present in the insoluble matter, and if a filter is employed to remove the analyte of interest from debris or unwanted material, the filter is typically adapted to allow the analyte of interest (and perhaps other similarly-sized insoluble matter) to pass through the filter as filtrate 16, while restricting relatively large insoluble matter 17 from passing through the filter. Therefore, it should be understood that the filtrate 16 can also include some insoluble matter, and insoluble matter 17 is shown in FIG. 1 as being removed from the liquid composition 14 for simplicity and by way of example only. A sample 18 comprising an analyte of interest (if present) can then be captured or collected from at least a portion of the filtrate 16. Samples 18 from a variety of sample preparation systems can be pooled together for one or more of collection, enrichment, concentration, analysis, etc. In some embodiments, the sample 18 can include substantially only the analyte of interest (if present), for example, if a sample collection system used is specific to the analyte of interest. In some embodiments, the sample 18 will include the analyte of interest (if present) among other things, for example, if the sample collection system used is nonspecific.

Throughout the present disclosure, one or more of the liquid composition 14, the filtrate 16, and any samples 18 thereof, may be described as including the analyte of interest. However, in some embodiments, the liquid composition 14 may not include the analyte of interest and may lead to a negative test result when the sample is analyzed. For example, if a sample is prepared from a food source, and the sample is then is tested for a bacterium, and the food source did not include that bacterium, the liquid composition 14 formed from that food, and any filtrates 16 and samples 18 thereof will also not include that bacterium of interest. Thus, even if one or more of the liquid composition 14, the filtrate 16, and any samples 18 taken therefrom are described as including the analyte of interest, it should be understood that this would only be the case if the analyte of interest was present. Furthermore, the sample collection systems of the present disclosure are adapted to isolate or capture the analyte of interest from the filtrate (or liquid composition). In some embodiments, the sample collection system is specific (e.g., the sample collection system is functionalized) and will capture substantially only the analyte of interest, if it is present. In some embodiments, the sample collection system is nonspecific (e.g., the sample collection system is size-restrictive) and will capture a sample that comprises the analyte of interest, if is present, possibly among other things.

The sample preparation and collection method 10 illustrated in FIG. 1 and described above is illustrated and described by way of example only. However, one of ordinary skill in the art should understand that the sample preparation and collection method of the present disclosure need not include every step illustrated in FIG. 1 and described above. For example, in some embodiments of the present disclosure, the sample preparation and collection method does not include the filtering step, but rather a sample is collected from the liquid composition 14.

The diluent 13 is generally a liquid and, in some embodiments, is a sterile liquid. In some embodiments, the diluent 13 can include a variety of additives, including, but not limited to, surfactants, or other suitable additives that aid in dispersing, dissolving, suspending or emulsifying the source for subsequent analyte testing; rheological agents; antimicrobial neutralizers (e.g., that neutralize preservatives or other antimicrobial agents); enrichment or growth medium comprising nutrients (e.g., that promote selective growth of desired microorganism(s)) and/or growth inhibitors (e.g., that inhibit the growth of undesired microorganism(s)); pH buffering agents; enzymes; indicator molecules (e.g. pH or oxidation/reduction indicators); spore germinants; an agent to neutralize sanitizers (e.g., sodium thiosulfate neutralization of chlorine); an agent intended to promote bacterial resuscitation (e.g., sodium pyruvate); or a combination thereof. In some embodiments, the diluent 13 includes sterile water (e.g., sterile double-distilled water (ddH$_2$O)); one or more organic solvents to selectively dissolve, disperse, suspend, or emulsify the source; aqueous organic solvents, or a combination thereof. In some embodiments, the diluent 13 is a sterile buffered solution (e.g., Butterfield's Buffer, available from Edge Biological, Memphis Term.). In some embodiments, the diluent 13 is a selective or semi-selective nutrient formulation, such that the diluent 13 may be used in the selective or semi-selective growth of the desired analyte(s) (e.g., bacteria). In such embodiments, the diluent 13 can be incubated with the source 12 for a period of time (e.g., at a specific temperature) to promote such growth of the desired analyte(s).

Examples of growth medium can include, but are not limited to, Tryptic Soy Broth (TSB), Buffered Peptone Water (BPW), Universal Pre-enrichment Broth (UPB), *Listeria* Enrichment Broth (LEB), Lactose Broth, Bolton broth, or other general, non-selective, or mildly selective media known to those of ordinary skill in the art. The growth medium can include nutrients that support the growth of more than one desired microorganism (i.e., analyte of interest).

Examples of growth inhibitors can include, but are not limited to, bile salts, sodium deoxycholate, sodium selenite, sodium thiosulfate, sodium nitrate, lithium chloride, potassium tellurite, sodium tetrathionate, sodium sulphacetamide, mandelic acid, selenite cysteine tetrathionate, sulphamethazine, brilliant green, malachite green oxalate, crystal violet, Tergitol 4, sulphadiazine, amikacin, aztreonam, naladixic acid, acriflavine, polymyxin B, novobiocin, alafosfalin, organic and mineral acids, bacteriophages, dichloran rose bengal, chloramphenicol, chlortetracycline, certain concentrations of sodium chloride, sucrose and other solutes, and combinations thereof.

In some embodiments, the source 12 includes the diluent 13, such that the liquid composition 14 includes the source 12 and the diluent 13, but the diluent 13 was not added separately. For example, a food source that includes a substantial amount of water or other liquid can be mixed to form the liquid composition 14 comprising the source 12 and the diluent 13, without requiring the addition of a separate diluent 13. In some embodiments, the source 12 may be substantially dissolved in the diluent 13, such that the liquid composition 14 includes a minimal amount of insoluble matter 15, making the filtering step unnecessary.

FIG. 17 illustrates a sample preparation and collection system 1107 according to one embodiment of the present disclosure. The sample preparation and collection system 1107 includes a sample preparation system 1100 and a sample collection system 1157 coupled to the sample preparation system 1100, such that the sample collection system 1157 is in fluid communication with the sample preparation system 1100. The sample preparation system 1100 prepares a liquid composition 1114 (and, optionally, a filtrate 1116) from a source 1112, and the sample collection system 1157 is configured to collect a sample from the sample preparation system 1100 that comprises an analyte of interest, if present. The sample can be further removed (e.g., by elution) from the sample collection system 1157 for further processing, such as enrichment, concentration, incubation, analysis (e.g., identification or quantification of analyte(s) of interest), etc.

FIGS. 2-13 illustrate various embodiments of the sample preparation system according to the present disclosure, FIGS. 18-20 and 23-24 illustrate various embodiments of the sample collection system according to the present disclosure, and FIGS. 14-17, 21-22 and 25 illustrate various embodiments of the sample preparation and collection system according to the present disclosure (including various embodiments of the sample preparation system and the sample collection system).

Figure 2:
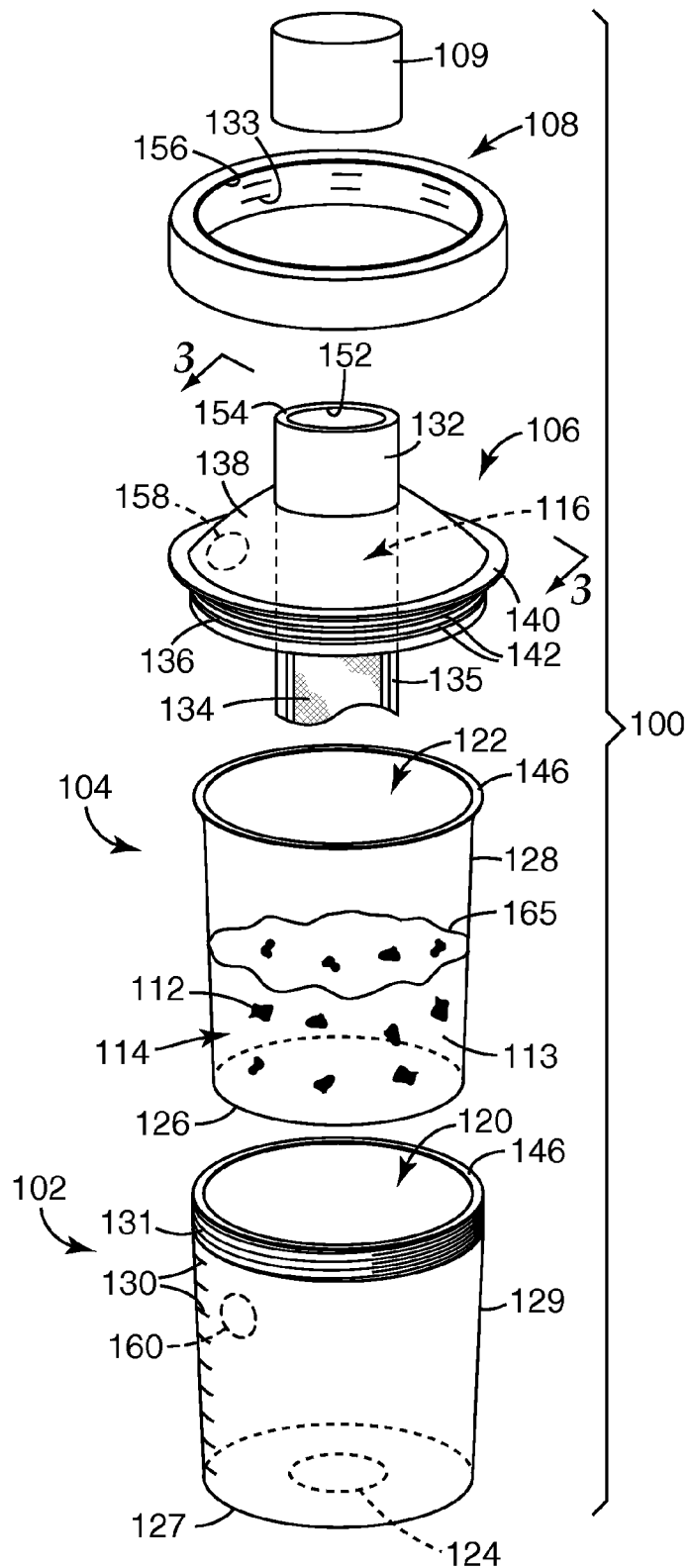
FIG. 2 is an exploded perspective view of a sample preparation system according to one embodiment of the present disclosure, the sample preparation system including a lid.

FIG. 2 illustrates a sample preparation system 100 according to one embodiment of the present disclosure. As shown in FIG. 2, the sample preparation system 100 includes a container 102, a liner 104, a lid 106, a collar 108, and a cover 109. In some embodiments, one or more of the components of the sample preparation system 100 are sterile or sterilizable by sterilization and disinfection procedures such as steam, gamma radiation, ethylene oxide, hydrogen peroxide, peracetic acid, hydro-alcoholic solutions, bleach, and combinations thereof. A system having similar features to that of the sample preparation system 100 is described in PCT Publication No. WO 98/32539, U.S. Pat. Nos. 6,536,687 and 6,588,681, PCT Publication No. 2004/060574, PCT Publication No. 2004/060575, US Publication No. 2004/0164182, PCT Publication No. 2004/094072, PCT Publication No. WO 2007/079143, PCT Publication No. WO 2007/079188, each of which is incorporated herein in its entirety by reference.

Some embodiments of the present disclosure employ a plurality of sample preparation systems 100 to allow multiple sample preparation systems 100 be employed in parallel (or to have samples pooled) to expedite sample preparation and/or collection, and to increase productivity/output. In such embodiments, the plurality of sample preparation systems 100 can be at least partially integrally formed, or they can be separately formed. For example, in some embodiments, multiple liners 104 can be used in one relatively large container 102 (e.g., with multiple reservoirs for the liners 104).

In some embodiments, as shown in FIG. 2, the container 102 is freestanding and/or self-supporting and includes a base 127 and a sidewall 129. The term "freestanding" is generally used to refer to an object that is capable of standing on its own without collapsing or distorting, and without being held by another object. The term "self-supporting" is generally used to refer to an object that does not collapse or deform under its own weight. For example, a bag is typically not "self-supporting" in that it does not maintain its shape, but rather collapses or distorts, under its own weight. A self-supporting object is not necessarily freestanding.

The container 102 can be formed of a variety of materials including, but not limited to, polymeric materials, metals (e.g., aluminum, stainless steel, etc.), ceramics, glasses, and combinations thereof. Examples of polymeric materials can include, but are not limited to, polyolefins (e.g., polyethylene, polypropylene, combinations thereof, etc.), polycarbonate, acrylics, polystyrene, high density polyethylene (HDPE), polypropylene, other suitable polymeric materials capable of forming a freestanding and/or self-supporting container, or a combination thereof. The container 102 can be translucent (or even transparent), or opaque, and can be any suitable size, depending on the type, amount and size of source to be analyzed. For example, in some embodiments, the container 102 can have a capacity of 50 mL, 100 mL, 250 mL, or larger.

In some embodiments, as shown in FIG. 2, the sample preparation system 100 includes a liner 104, which is shaped and dimensioned to be received within the container 102. The liner 104 can be disposable (e.g., made for one-time use), to allow the container 102 to be reused without substantial risk of contamination and without extensive cleaning required between uses. As described in greater detail below and illustrated in FIG. 9, in some embodiments, the sample preparation system includes a liner without a container. When the liner is used without a container, it is not functioning as a "liner," per se, and can be referred to generally as a receptacle or container.

As shown in FIG. 2, the container 102 defines a first reservoir 120, and the liner 104 defines a second reservoir 122. The liner 104 is shaped and dimensioned to be received within the first reservoir 120 of the container 102. In some embodiments, a source 112 and a diluent 113 can be added to the first reservoir 120. In some embodiments, as shown in FIG. 2, the liner 104 is employed, and the source 112 and diluent 113 are positioned within the second reservoir 122, and the liner 104 is positioned within the first reservoir 120. Whether added to the first reservoir 120 or the second reservoir 122, the source 112 and the diluent 113 can be combined (and agitated) to form a liquid composition 114. In some embodiments, the liner 104 is freestanding, and the liner 104 or the container 102 can serve as a freestanding receptacle that can contain the liquid composition 114.

The source 112 can be added to the container 102 or the liner 104 first, followed by addition of the diluent 113, the diluent 113 can be added first, followed by the source 112, or the source 112 and the diluent 113 can be added simultaneously. Alternatively, the source 112 and diluent 113 can be combined prior to being added to the sample preparation system 100.

In some embodiments in which the diluent 113 is added to the container 102 or the liner 104 first, a pre-measured amount of the diluent 113 (e.g., a sterile liquid diluent) can be sealed in the container 102 or the liner 104 with a removably coupled cover (e.g., a one-time use removable barrier film that is coupled to the container 102 or the liner 104 by one or more of an adhesive, heat sealing, ultrasonic welding, or any of the other coupling means described below), so that the cover can be removed just prior to adding the source 112. Alternatively, in some embodiments, a pre-measured amount of a dry powdered media (e.g., nutrient media for analyte(s) of interest and/or growth inhibitors for analyte(s) not of interest) can be sealed in the container 102 or the liner 104 with a removably coupled cover, or the desired media can be coated or adsorbed onto an inner surface of the container 102 or the liner 104. In such embodiments, the cover can be removed and a solvent (e.g., ddH$_2$O) can be added to form the diluent 113, either prior to or at the same time as the source 112 is added. Alternatively, if the source 112 includes enough of a liquid capable of dissolving the media, the source 112 can be added to the dry powdered media to form the liquid composition 114 that comprises the source 112 and a diluent 113 (e.g., the media dissolved in a solvent provided by the source 112).

In some embodiments, the container 102 and/or the liner 104 (if the liner 104 is employed) can be compartmentalized to include more than one first reservoir 120 and/or more than one second reservoir 122, respectively. Multiple reservoirs 120/122 can be used, for example, for multi-stage enrichment, for parallel or simultaneous enrichment of different microorganisms, or a combination thereof. By way of example, the liner 104 can include two second reservoirs 122 (referred to in this example as reservoir A and B for simplicity). A first enrichment media can be positioned in reservoir A for primary enrichment of a microorganism, and a second enrichment media can be positioned in reservoir B for secondary enrichment of the same microorganism. Reservoirs A and B can be positioned, for example, such that both are accessible for positioning of the media but that the source 112 can be added to one without being added to the other. After the liquid composition 114 has been formed and primary enrichment has occurred in reservoir A, the liquid composition 114, or a portion thereof, can be moved to reservoir B for secondary enrichment. The liquid composition 114 can be moved to reservoir B in a variety of ways, including agitation of the sample preparation system 100, breaking of a frangible barrier between the two reservoirs A and B, etc.

In some embodiments, one container 102 can be employed with a plurality of liners 104, such that one container 102 can include one or more first reservoirs 120, and/or one or more liners 104 (each including one or more second reservoirs 122) can be positioned in the container 102. Other configurations are possible, and one of ordinary skill in the art will recognize the different permutations possible for achieving multiple compartments. No matter what the configuration, the multiple reservoirs or compartments can be positioned side-by-side, vertically, concentrically, or a combination thereof.

The liner 104 can be formed of a variety of materials, including a variety of polymeric materials, including, but not limited to, a polyolefin, including, but not limited to polypropylene (e.g., low density polyethylene (LDPE)), polyethylene, and poly(methylpentene), polyamide (e.g., NYLON®), or a combination thereof. In some embodiments, the liner 104 is formed from a molding process, such as a thermoforming process. The liner 104 can be translucent (or even transparent), or opaque.

In some embodiments, as illustrated in FIG. 2, the liner 104 is freestanding and/or self-supporting, either of which can allow the source 112 and diluent 113 to be loaded into the liner 104 prior to positioning the liner 104 within the container 102, without the liner 104 collapsing or distorting. In addition, a freestanding and/or self-supporting liner 104 can aid in weighing, source 112 and/or diluent 113 addition, transporting, handling, and/or sample removal.

In some embodiments, the liner 104 is self-supporting and/or freestanding while also being deformable. The term "deformable" is used to refer to a structure that can be altered from its original shape or state by pressure (e.g., positive or negative) or stress. In embodiments employing a deformable liner 104, pressure can be applied to the liner 104 to reduce its size from its original (i.e., unstressed) dimensions. Such pressure can be used to promote removal of the liquid composition 114 (or a filtrate thereof) from the liner 104. In such embodiments, the liner 104 can serve as a deformable self-supporting receptacle that can contain the liquid composition 114. In some embodiments, the deformable self-supporting receptacle is also freestanding.

In some embodiments, as shown in FIG. 2, the container 102 includes an aperture 124 formed in its base 127, through which a user can access the liner 104 to apply pressure to the liner 104 to cause it to deform. Such pressure can be applied directly by hand, or by an additional device, and could be a manual or automated process. The aperture 124 can be shaped and dimensioned according to the desired application of use. In some embodiments, base 127 of the container 102 is nothing more than the bottom of the sidewall 129, or a slight inward projection of the sidewall 129, such that the liner 104 is easily accessible at the bottom of the container 102. Said another way, in some embodiments, the aperture 124 of the container 102 defines a majority of the bottom of the container 102 (e.g., a majority of the cross-sectional area of the container 102), and the base 127 is only a small portion of the container 102 surrounding the aperture 124. In embodiments that do not employ the liner 104, the container 102 need not include the aperture 124.

In some embodiments, the liner 104 includes a relatively rigid base 126 and a relatively thin and deformable sidewall 128, such that when pressure is applied to the base 126 in a direction parallel to the longitudinal axis of the liner 104 (e.g., via the aperture 124 in the container 102), the liner 104 deforms in the longitudinal direction (e.g., by virtue of the sidewall 128 collapsing rather than the base 126). Alternatively, or in addition, the base 126 can be thicker than the sidewall 128. By way of example only, in some embodiments, the thickness of the sidewall 128 is at least 50 µm, in some embodiments, at least 100 µm, in some embodiments, at least 150 µm, and in some embodiments, at least 200 µm. In some embodiments, the thickness of the base 126 is at least 225 µm, in some embodiments, 275 µm, in some embodiments, at least 300 µm, and in some embodiments, at least 350 µm.

The liner 104 can further include one or more of baffles, pleats, corrugations, seams, joints, gussets, weakened portions (e.g., annular weakened portions), or a combination thereof, which may be incorporated to assist in controlling the deformability of the liner 104, and/or can further reduce the internal volume of liner 104. In some embodiments, as described in greater detail below and illustrated in FIG. 9, the liner 104 includes an accordion-type configuration. In some embodiments, liner 104 does not include any grooves on its internal surface, particularly, at the internal junction between the base 126 and the sidewall 128.

In some embodiments, the liner 104 is deliberately deformed to impart a disruption to the surface geometry of the liner 104. Such a disrupted surface geometry can assist in the breakup of the source 112 during agitation. For example, in some embodiments, an obstruction (e.g., a relatively rigid material) can be positioned between the sidewall 128 of the liner 104 and the container 102 to create a different surface geometry in the sidewall 128 of the liner 104.

As shown in FIG. 2, the container 102 can include indicia 130 to indicate the level (i.e., volume) of contents within the container 102. The indicia 130 can be used to achieve a desired weight ratio of the liquid composition 114, for example, where the weight ratio of the source 112 to the diluent 113 ranges from 1:100 to 1:1. One example of suitable indicia is described in U.S. Pat. No. 6,588,681. Alternatively, or in addition, the liner 104 can include indicia. To enable the use of the indicia 130 on the container 102 and/or the liner 104, the container 102 and/or the liner 104 can be translucent, or even transparent to afford seeing the liquid composition 114 through the sidewall 129 of the container 102 and/or the sidewall 128 of the liner 104. The sidewalls 128 and 129 may also bear other types of markings, such as trademarks, brand names, and the like. The indicia 130 can also be provided on a film that is dimensioned to be received within the container 102 or the liner 104 and which can be formed of a material that includes sufficient internal stresses to cause the film to press outwardly (i.e., radially) against an inner surface of the container 102 or the liner 104.

In the embodiment illustrated in FIG. 2, the lid 106 is removably coupled to the liner 104, and the collar 108 is employed to further secure the lid 106 to the container 102. For example, in FIG. 2, the container 102 includes threads 131 at the upper end of the outer surface of the sidewall 129, which are shaped and dimensioned for the collar 108 (having internal threads 133 capable of engaging with the threads 131 on the container 102) to be screwed onto the upper end of the container 102. As an alternative to using the collar 108 for securing the lid 106 to the container 102, other coupling means can be employed including clamping and/or any of the other coupling means described below. In some embodiments, the liner 104 is not employed, and the lid 106 can be coupled directly to the container 102. In such embodiments, the collar 108 need not be employed. Thus, the lid 106 can form a seal (e.g., a hermetic seal) with either the container 102 or the liner 104. In some embodiments, the lid 106 and the container 102 (or the lid 106 and the liner 104) are integrally formed or permanently coupled together.

A variety of coupling means can be employed either between the lid 106 and the liner 104, the lid 106 and the container 102, and/or the collar 108 and the container 102 to allow the respective components to be removably coupled to one another, including, but not limited to, gravity (e.g., one component can be set atop another component, or a mating portion thereof), screw threads, press-fit engagement (also sometimes referred to as "friction-fit engagement" or "interference-fit engagement"), snap-fit engagement, magnets, adhesives, heat sealing, other suitable removable coupling means, and combinations thereof. In some embodiments, the sample preparation system 100 need not be reopened after the source 112 and the diluent 113 are added, such that the container 102, the liner 104, the lid 106 and the collar 108 need not be removably coupled to one another, but rather can be permanently or semi-permanently coupled to one another. Such permanent or semi-permanent coupling means can include, but are not limited to, adhesives, stitches, staples, screws, nails, rivets, brads, crimps, welding (e.g., sonic (e.g., ultrasonic) welding), any thermal bonding technique (e.g., heat and/or pressure applied to one or both of the components to be coupled), snap-fit engagement, press-fit engagement, heat sealing, other suitable permanent or semi-permanent coupling means, and combinations thereof. One of ordinary skill in the art will recognize that some of the permanent or semi-permanent coupling means can also be adapted to be removable, and vice versa, and are categorized in this way by way of example only.

Figure 3:
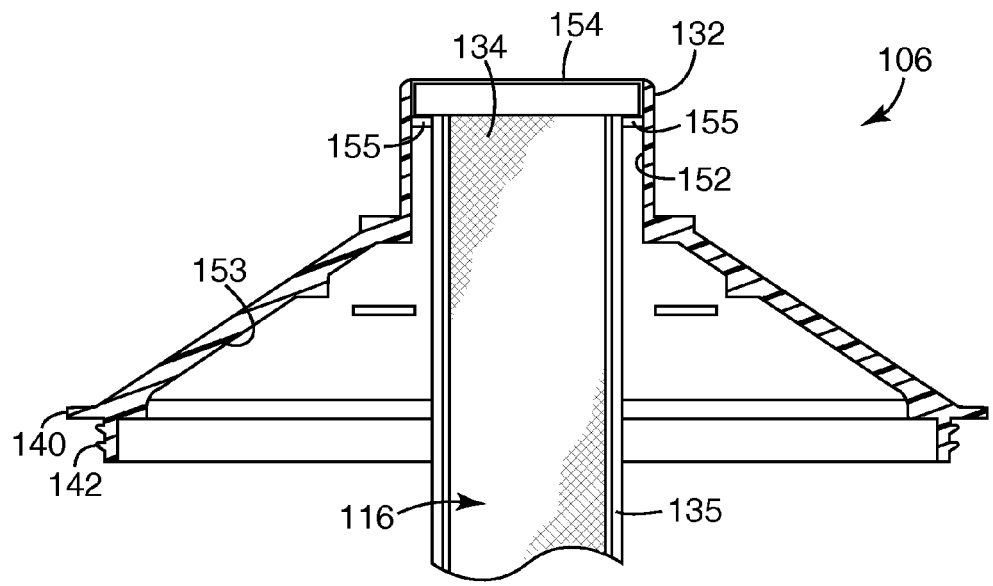
FIG. 3 is close-up cross-sectional view of the lid of FIG. 2, taken along line 3-3 in FIG. 2.

As shown in FIGS. 2 and 3, the lid 106 further includes a port 132, which can be coupled to a filter 134, a cylindrical portion 136 that is dimensioned to be received within the liner 104, and a generally conical (e.g., frusto-conical) portion 138 that extends from the cylindrical portion 136 to the port 132. At the junction between the cylindrical portion 136 and the conical portion 138, the lid 106 further includes a lip 140 that extends radially outwardly from the cylindrical portion 136 and the conical portion 138.

In some embodiments, the filter 134 is coupled directly to the lid 106. In some embodiments, as shown in FIGS. 2-3, the filter 134 can be supported by a frame 135 and coupled to the lid 106 via the frame 135. The frame 135 can form a portion of the filter 134, the frame 135 can be a part of the lid 106, or the frame 135 can be a separate element that is coupled to both the filter 134 and the lid 106. The frame 135 can be formed of a variety of materials, including, but not limited to, a variety of polymers, metals, ceramics, glasses, and combinations thereof. In the embodiment illustrated in FIGS. 2-3, the filter 134 is formed of a metal mesh, and the frame 135 is formed of a polymer that is bonded to the metal filter 134. The frame 135 is coupled to the lid 106, as described in greater detail below.

The filter 134 and the frame 135 of the embodiment illustrated in FIGS. 2 and 3 are shaped and dimensioned so as to extend below the bottom end of the lid 106, such that when the sample preparation system 100 is assembled, the filter 134 and the frame 135 extend into the second reservoir 122 of the liner 104 (or the first reservoir 120 of the container 102). However, the filter 134 and frame 135 can take on a variety of shapes and sizes. In some embodiments, for example, the frame 135 can include a rigid upper portion (e.g., that is coupled to the lid 106) and a rigid lower portion, and the filter 134 can be coupled therebetween, and the filter 134 can be collapsible. Such an embodiment is described in greater detail below and illustrated in FIG. 9.

The cylindrical portion 136 of the lid 106 includes a plurality of circumferential outwardly-projecting protrusions 142 to allow the cylindrical portion 136 to be snap-fit or press-fit to the inner surface of the liner 104. In some embodiments, the inner surface of the liner 104 can include inwardly-projecting protrusions that are used either in lieu of the outwardly-projecting protrusions 142, or in addition to the outwardly-projecting protrusions 142 (e.g., to form a mating relationship therewith).

The liner 104 can include a lip 144 that projects radially outwardly from the sidewall 128 of the liner 104, and which can form an abutting relationship with an upper surface 146 of the container 102 and the lip 140 of the lid 106, such that when the sample preparation system 100 is assembled, the lip 144 of the liner 104 is positioned between the lip 140 of the lid 106 and the upper surface 146 of the container 102, and a seal (e.g., a hermetic seal) is formed. As shown in FIG. 2, the collar 108 includes an inwardly-projecting lip 156, such that when the collar 108 is coupled to the container 102, the lip 156 of the collar 108 presses the lip 140 of the lid 106 into contact with the lip 144 of the liner 104, which is pressed into contact with the upper surface 146 of the container 102 (e.g., to form a higher integrity seal). The above-described means for assembling the sample preparation system 100 and for forming a seal between the components of the sample preparation system 100 are described and illustrated by way of example only. One of ordinary skill in the art will understand, however, that a variety of other mechanisms could be employed to assemble the components of the sample preparation system 100 and to form a seal (e.g., a liquid-tight seal, a hermetic seal, or a combination thereof), such that the sample preparation system 100 is inhibited from leaking under normal operating conditions.

While the lid 106 of the embodiment illustrated in FIGS. 2 and 3 is illustrated as having a generally conical or frusto-conical shape. It should be understood that the lid 106 could have a variety of other shapes, including, but not limited to, a cylindrical shape, a tubular shape having a rectangular or square cross-sectional area, or other shapes suitable to being coupled to the other components of the sample preparation system 100. Similarly, the container 102, the liner 104, and the collar 108 could have a variety of other shapes than the substantially cylindrical shapes illustrated in FIG. 2. In addition, the lid 106 can be dimensioned to accommodate the other components of the sample preparation system 100.

The lid 106 can be formed of a variety of materials, including the materials listed above with respect to the container 102. The lid 106 can be translucent (or even transparent), or opaque, depending on the application of use.

The collar 108 can be formed of a variety of materials, including, but not limited to a variety of polymeric materials, metal materials, and combinations thereof. For example, the collar 108 can be formed of a molded plastic component, or a machined metal (such as aluminum) component. In some embodiments, the collar 108 is formed of a molded plastic component comprising glass fiber reinforced polypropylene.

As shown in FIG. 2, the port 132 of the lid 106 is generally cylindrical and tubular in shape, such that the port 132 defines a portion 152 of the inner surface 153 of the lid 106 and an opening 154 in the lid 106. The lid 106 is hollow and is in fluid communication with the second reservoir 122 when the sample preparation system 100 is assembled. The port 132 does not need to be cylindrical and can instead take on any shaped necessary for a given application. In the embodiment illustrated in FIGS. 2 and 3, the filter 134 is coupled to the port 132 (i.e., via the frame 135) such that the filter 134 is in fluid communication with the lid opening 154, as well as the second reservoir 122.

In the embodiment shown in FIG. 2, the cover 109 is shaped and dimensioned to receive at least a portion of the port 132. As a result, the cover 109 can be coupled to the port 132 of the lid 106 to close the opening 154 in the lid 106 and to seal (e.g., hermetically seal) the sample preparation system 100 from the environment. The cover 109 can be coupled to the lid 106 using any of the above-described coupling means. The cover 109 can be integrally formed with the lid 106 (e.g., a flip-top snap-on cover, as described in greater detail below and illustrated in FIG. 13), or the cover 109 can be separate from the lid 106 (e.g., a screw-on cover, as described in greater detail below and illustrated in FIGS. 9-12). The cover 109 can be formed of a variety of materials, including the materials listed above with respect to the container 102 or the collar 108.

In some embodiments, the lid 106 includes a frangible or penetrable barrier or a removable film separating at least a portion of the interior of the lid 106 from the environment, such that the barrier can be punctured or pierced or the film removed to access the interior of the lid 106. In such embodiments, the cover 109 need not be employed.

Figure 5:
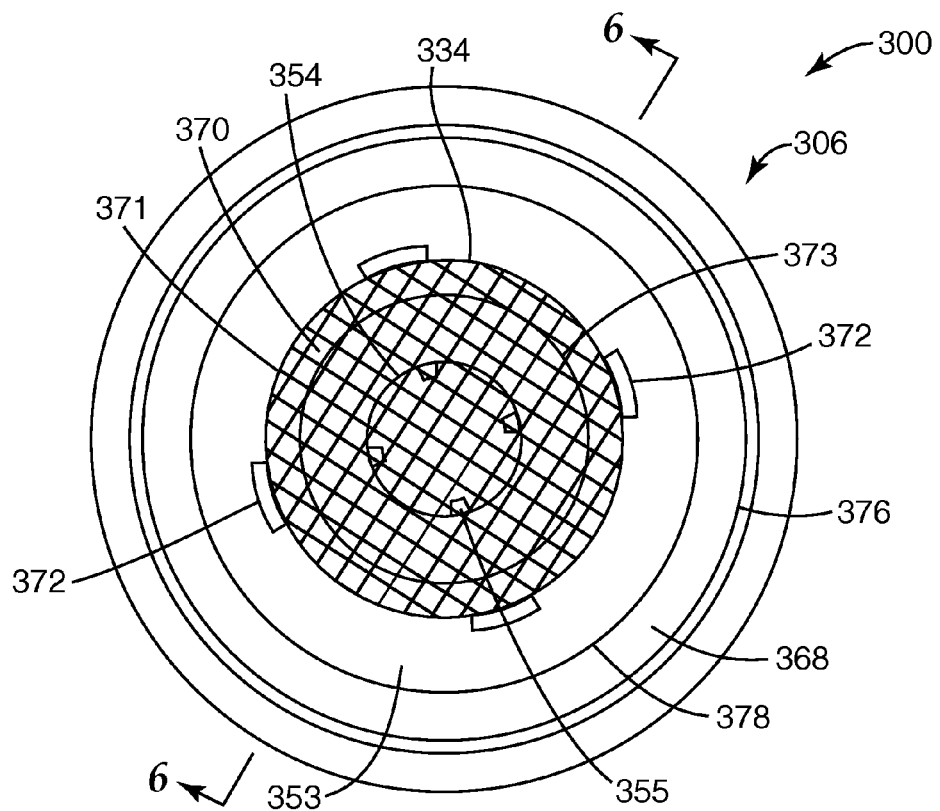
FIG. 5 is a bottom view of a lid of a sample preparation system according to another embodiment of the present disclosure.
Figure 6:
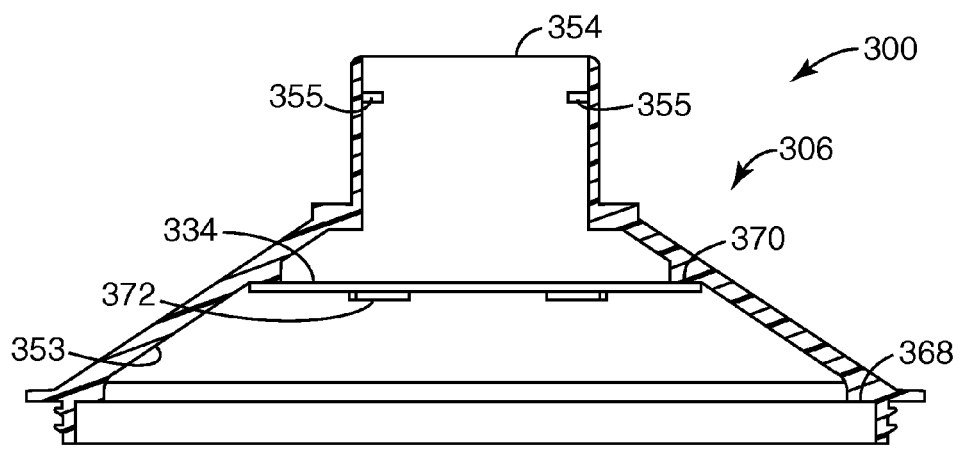
FIG. 6 is a cross-sectional view of the lid of FIG. 5, taken along line 6-6 in FIG. 5.

As shown in FIG. 3, the inner surface 153 of the lid 106 can include a variety of inner circumferential edges to which other components (e.g., additional or alternative filters, the concept of which is illustrated in FIGS. 5-6 and described below) can be coupled. The inner circumferential edges can have any orientation desired, depending on what other components are desired to be coupled to the edges. In some embodiments, the inner circumferential edges are oriented substantially orthogonally to the central longitudinal axis of the lid 106, such that the edges are substantially horizontal in FIG. 3.

In addition, the lid 106 can include a variety of inwardly-extending members to which other components (e.g., filters) can be coupled. For example, as shown in FIG. 3, the filter 134 is supported by the frame 135, and the lid 106 includes inwardly-extending members 155 to which the frame 135 can be coupled via a variety of coupling means, including, but not limited to, any of the coupling means described above. The inwardly-extending members 155 can be integrally formed with the lid 106.

The filter 134 can be of any geometrical shape to sufficiently filter the liquid composition 114. In some embodiments, the filter 134 is deformable and/or collapsible (i.e., such that the filter 134 folds under its own weight). In some embodiments, the filter 134 is rigid and retains its shape (i.e., does not fold under its own weight). The size and number of filters 134 used in a sample preparation system 100, and porosity thereof, may vary, depending on the desired analyte(s) and the insoluble matter in the source 112.

By way of example only, in some embodiments, the liquid composition 114 comprises food, the desired analyte is bacteria, and the insoluble matter is food particles or debris. In such embodiments, for example, the filter 134 can be selected to retain and/or separate the food particles, while allowing the bacteria of interest (if present) to pass through the filter 134 for subsequent analysis. By way of further example, in some embodiments, the liquid composition 114 comprises a lysed bacterial cell culture, the desired analyte is one or more of DNA, RNA, a protein, or a metabolite, and the insoluble matter is cellular debris. In such embodiments, for example, the filter 134 can be selected or treated (e.g., derivatized with biomolecule-binding agents, such as antibodies) to retain and/or separate the cellular debris, while allowing the desired DNA, RNA, protein, and/or metabolite to pass through the filter 134 for subsequent analysis. Alternatively, for example, the filter 134 can be selected or treated to retain the desired DNA, RNA, protein and/or metabolite, while allowing the cellular debris to pass through the filter 134.

The filter 134 can have a variety of pore sizes sufficient for retaining particles from the liquid composition 114, while allowing the desired analyte(s) (if present) in the liquid composition 114 to pass through the filter 134 for extraction and/or sampling. Alternatively, the filter 134 can be sized, charged and/or functionalized to retain the desired analyte(s), while allowing undesired material to pass through the filter 134. In such embodiments, the sample can include at least a portion of the filter 134, which can be further processed (e.g., enriched, concentrated, analyzed, etc.).

In some embodiments, the filter 134 has an average pore or mesh size of at least 2 µm, in some embodiments, at least 5 µm, in some embodiments, at least 40 µm, in some embodiments, at least 80 µm, and in some embodiments, at least 120 µm. In some embodiments, the filter 134 has an average pore or mesh size of at most 2000 µm, in some embodiments, at most 1000 µm, in some embodiments, at most 500 µm, in some embodiments, at most 200 µm, in some embodiments, at most 50 µm, in some embodiments, at most 10 µm and in some embodiments, at most 1 µm (e.g., if it is desired to restrict bacteria from passing through the filter 134).

In the embodiment illustrated in FIGS. 2 and 3, the filter 134 is located in the lid 106, generally in line with the central longitudinal axis of the lid 106. However, in some embodiments, the filter 134 is positioned in an "off-axis" position of the lid 106. For example, an aperture 158 is shown in dashed lines in FIG. 2 to represent a possible "off-axis" position for the filter 134 in the lid 106. An alternative or an additional port can be positioned at the location of the aperture 158 and coupled thereto. The filter 134 can be permanently or removably coupled at one or both locations.

In some embodiments, particularly embodiments that do not employ the liner 104, the filter 134 can alternatively, or additionally, access the interior of the sample preparation system 100 (i.e., the first reservoir 120 of the container 102) via an aperture 160 in the sidewall 129 of the container 102 or the aperture 124 in the base 127 of the container 102 (or an aperture formed in a different location of the base 127 of the container 102). In such embodiments, the filter 134 can be permanently or removably coupled to the sidewall 129 or the base 127 of the container 102. An alternative or additional port can be positioned at the location of the apertures 160 and 124 and coupled thereto. In some embodiments, the sample preparation system 100 can include more than one port, such as the port 132 in the lid 106, an additional port at the location of the aperture 158 in the lid 106, an additional port at the location of the aperture 160 in sidewall 129 of the container 102, and/or an additional port at the location of the aperture 124 in the base 127 of the container 102. The cover 109 or a similar closure device can be used to seal any of the ports at any location on the sample preparation system 100.

Because of the different locations possible for the filter 134, the filter 134 can be shaped and dimensioned to accommodate its position in the sample preparation system 100 and the particular application of use. In any of the possible locations for the filter 134, the filter 134 can be positioned wholly above or wholly below the level 165 of the liquid composition 114, or the filter 134 can be positioned partially above and partially below the level 165 of the liquid composition 114, depending on the type of filtering desired, and how the filter 134 is intended to filter the liquid composition 114. For example, in the embodiment illustrated in FIG. 2, the filter 134 is coupled to the port 132 and, depending on how high the level 165 of the liquid composition 114 is, would typically extend from the port 132 into the interior of the sample preparation system 100, such that the filter 134 is positioned partially above and partially below the level 165 of the liquid composition 114.

The filter 134 is in fluid communication with the interior of the liner 104 and the liquid composition 114 and acts to filter the liquid composition 114 to form a filtrate 116. The filtrate 116 is disposed within the volume of the filter 134 and can be extracted and/or sampled from the adjacent port 132. In embodiments employing filters 134 at multiple locations, the filtrate 116 can be sampled from any of the ports or apertures described above.

The filter 134 can be formed from a variety of materials, including, but not limited to one or more of nylon, fluorinated polymers (e.g., polytetrafluoroethylene (PTFE)), cellulosics (e.g., modified celluloses such as cellulose esters (e.g., cellulose acetate) and nitrocelluloses), fiberglass, papers, and combinations thereof. In some embodiments, the filter 134 can be formed of a woven web, a nonwoven web, a molded structure, a foam, fabric, a fibrous web, and combinations thereof. The surface area of the filter 134 can be increased by pleating the filter 134, or by other similar techniques. The thickness of the filter 134 can be controlled by calendering or felting processes.

In some embodiments (no matter which location the filter 134 is in), the filter 134 can be used as a retainer or holder of the source 112. An example of this concept is illustrated in FIG. 4 and described below.

As mentioned above, the liner 104 can be disposable. In addition, in some embodiments, one or more of the lid 106, the cover 109 and the filter 134 can also be disposable. For example, in some embodiments, the lid 106 can be coupled to the liner 104, and the cover 109 and the filter 134 can be coupled to the lid 106. The liner 104, the lid 106, the filter 134 and the cover 109 can form a disposable portion of the sample preparation system 100 that can be used without contaminating the container 102 or the collar 108. The disposable portion can be removed from the container 102 and disposed. The container 102 and collar 108 can then be reused with a new liner 104, lid 106, filter 134 and cover 109.

Figure 4:
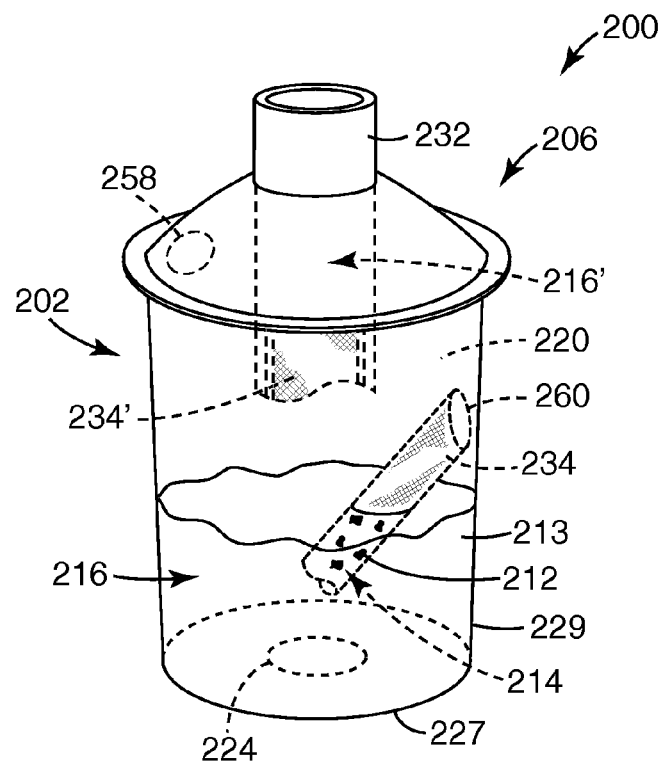
FIG. 4 is a perspective view of a sample preparation system according to another embodiment of the present disclosure.

FIG. 4 illustrates a sample preparation system 200 according to another embodiment of the present disclosure, wherein like numerals represent like elements. The sample preparation system 200 shares many of the same elements and features described above with reference to the illustrated embodiment of FIGS. 2-3. Accordingly, elements and features corresponding to elements and features in the illustrated embodiment of FIGS. 2-3 are provided with the same reference numerals in the 200 series. Reference is made to the description above accompanying FIGS. 2-3 for a more complete description of the features and elements (and alternatives to such features and elements) of the embodiment illustrated in FIG. 4.

The sample preparation system 200 includes a container 202 and a lid 206. The sample preparation system 200 does not include a liner, and the lid 206 is coupled directly to the container 202. The sample preparation system 200 further includes a filter 234 which is fluidly coupled to an aperture 260 formed in a sidewall 229 of the container 202. Unlike the filter 134 of the sample preparation system 100, the filter 234 functions as a retainer or holder for the source 212.

The filter 234 can be permanently coupled to the container 202 and the source 212 can be added to the filter 234, or the filter 234 can be removably coupled to the container 202, and the source 212 can be added to the filter 234 prior to or after the filter 234 is coupled to the container 202. In some embodiments, the filter 234 can be free-floating within the first reservoir 220 of the container 202, such that the filter 234 contains the source 212 and the diluent 213 is able to flow in and out of the interior of the filter 234 to mix with the source 212.

The source 212 is positioned within the filter 234, and the filter 234 is positioned at least partially below the level of the diluent 213 in the container 202 and is in fluid communication with the interior of the container 202, such that the source 212 can be combined with the diluent 213 to form a liquid composition 214 within the filter 234. The liquid composition 214 positioned within the filter 234 includes the analyte(s) of interest (if present) in the diluent 213, as well as any other soluble or insoluble matter from the source 212. During agitation, the source 212 and the diluent 213 can be mixed to allow the source 212 to be dissolved, dispersed, suspended and/or emulsified in the diluent 213. The pore size of the filter 234 will be adapted such that the diluent 213 and any analyte(s) of interest (if present) in the diluent 213 are free to flow in and out of the filter 234, such that the resulting filtrate 216 is positioned outside of the filter 234 and within the reservoir 220 of the container 202, and includes the diluent 213 and any present analyte(s) of interest.

The filtrate 216 can be sampled from any of a variety of ports or apertures, including the port 232 in the lid 206, the aperture 258 in the lid 206, an additional aperture in the sidewall 229 of the container 202, and/or an aperture 224 in the base 227 of the container 202. In addition, instead of being coupled to the sample preparation system 200 via the aperture 260, the filter 234 can instead be coupled to the sample preparation system 200 via any of a variety of ports or apertures, including the port 232 in the lid 206, the aperture 258 in the lid 206, and/or an aperture 224 in the base 227 of the container 202. In some embodiments, as shown in FIG. 4, one or more of the ports can include an additional filter 234' that functions in the same way as the filter 134 of the sample preparation system 100. In such embodiments, the filtrate 216 can be further filtered by the filter 234', and the resulting filtrate 216' is disposed within the filter 234' and can be extracted and/or sampled from the adjacent port (i.e., port 232 in FIG. 4).

The sample preparation system 200 can further include a liner, in which case the diluent 213 and resulting filtrate 216 can be positioned within the liner, provided that sufficient sealing is provided between the liner and the container 202 at the location of the aperture 260.

FIGS. 5-6 illustrate a sample preparation system 300 according to another embodiment of the present disclosure, wherein like numerals represent like elements. The sample preparation system 300 shares many of the same elements and features described above with reference to the illustrated embodiment of FIGS. 2-3. Accordingly, elements and features corresponding to elements and features in the illustrated embodiment of FIGS. 2-3 are provided with the same reference numerals in the 300 series. Reference is made to the description above accompanying FIGS. 2-3 for a more complete description of the features and elements (and alternatives to such features and elements) of the embodiment illustrated in FIGS. 5-6.

FIGS. 5-6 show only the lid 306 of the sample preparation system 300. The other components of the sample preparation system 300 can be assumed to include any of the other respective components of the sample preparation systems described above and illustrated in FIGS. 2-4, and thus for simplicity, are not shown in FIGS. 5-6.

The lid 306 is substantially similar to the lid 106 described above and illustrated in FIGS. 2-3, except that the lid 306 includes a filter 334 that is substantially planar and coupled to the inner surface 353 of the lid 306. The inner surface 353 of the lid 306 includes an upper inner circumferential edge 370 and a lower inner circumferential edge 368. As shown in FIG. 5, the upper inner circumferential edge 370 includes a downwardly facing surface that extends from an outer circumference 371 to an inner circumference 373. Similarly, the lower inner circumferential edge 368 includes a downwardly facing surface that extends from an outer circumference 376 to an inner circumference 378. The outer periphery of the filter 334 is coupled to the upper inner circumferential edge 370 of the inner surface 353. In addition, the filter 334 is in contact with retaining walls 372. The retaining walls 372 extend downwardly from the inner surface 353 of the lid 106 to retain the outer periphery of the filter 334.

The filter 334 can be coupled to the lid 306 using the same coupling means described above with respect to the lid 106. The filter 334 can be permanently or removably coupled to the lid 306. The degree of coupling between the filter 334 and the lid 306 may vary depending on a number of factors including, but not limited to, the filter 334 material, the lid 306 material, the size and texture of the coupled surface area, and the type of coupling means used. For example, if the filter 334 includes frayed edges, a wider and/or knurled coupling surface area may be used (e.g., the upper inner circumferential edge 370 can be knurled). Such a wider and/or knurled ultrasonic weld may capture frayed edges of the filter 334. To minimize the amount of fraying, the filter 334 can be cut using a laser, which can fuse the edges of the filter 334. Because the resulting laser-cut filter 334 would include a minimum amount of fraying, if any, a narrower coupling area can be used. In some embodiments, the coupling area extends completely around the outer periphery of the filter 334. In some embodiments, the coupling area can have an average width (i.e., a dimension within the same plane and substantially perpendicular to the outer periphery of the filter 334) of up to 5.0 mm, and in some embodiments, ranging from 1.0 mm to 3.0 mm. Alternatively, the filter 334 can be integrally formed with the lid 306, for example, by a molding process.

The filter 334 can be formed of the same material as the lid 306 or a different material. The filter 334 may be flexible, or semi-rigid. In some embodiments, the filter 334 is formed from a nylon nonwoven or woven fabric, while the lid 306 is an injection molded part formed of a polymer, such as polypropylene. In such embodiments, the nylon filter 334 can be coupled to the lid 306 via an ultrasonic welding technique. During ultrasonic welding, at least a portion of the upper inner circumferential edge 370 can melt to mechanically bond the filter 334. Since nylon has a higher melting temperature than polypropylene, the nylon filter 334 can maintain its structural integrity during the ultrasonic welding process. In such embodiments, at least a portion of the upper inner circumferential edge 370 can enter into a portion of filter 334, thereby encapsulating a portion of the filter 334.

The filter 334 can have dimensions and shapes that vary for a given application. The filter 334 can have any desired shape including, but not limited to, a circular shape, a square shape, a rectangular shape, a triangular shape, a polygonal shape, a star shape, other suitable shapes, and combinations thereof. In the embodiment illustrated in FIGS. 5 and 6, the filter 334 has a substantially circular shape.

The dimensions of the filter 334 may vary depending on the size of the lid 306. In some embodiments, the filter 334 has a largest dimension (i.e., length, width, or diameter) ranging from 15 mm to 100 mm, although the filter 334 may have smaller or larger dimensions. For example, in some embodiments, the filter 334 can have a circular shape and a diameter of 56 mm.

With continued reference to FIGS. 5 and 6, the retaining walls 372 can be integrally formed with the lid 306. In some embodiments, as shown in FIG. 5, the lid 306 comprises two or more retaining walls 372, wherein (i) each retaining wall 372 has a circumferential length greater than its thickness, (ii) each retaining wall 372 is positioned along an outer periphery of the filter 334, and (iii) the total circumferential length of the two or more retaining walls 372 is less than the total circumferential length of the outer periphery of the filter 334.

As shown in FIG. 5, the lid 306 includes four retaining walls 372 equally spaced from one another along outer circumference 371 of the upper inner circumferential edge 370. In some embodiments, each retaining wall 372 has a thickness ranging from 800 μm to 1200 μm, a length (i.e., in this exemplary embodiment, an arc length) extending a distance ranging from 1.0 mm to 22.0 mm along outer circumference 371, and a height ranging from 1.0 mm to 5.0 mm. In some embodiments, each retaining wall 372 has a segmented configuration so as to not inhibit (or to minimize the effect on) fluid flow around the retaining wall 372.

The lid 306 includes an opening 354 and inwardly-extending members 355. The inwardly-extending members 355 can be used to couple an additional filter (not shown) to the lid 306 in the same way that the filter 134 is coupled to the lid 106 in FIGS. 2 and 3. In such embodiments, the filter 334 is located below the additional filter, and the additional filter can have a length dimension less than the distance from the top the lid 306 to the filter 334.

In some embodiments, as shown in FIGS. 5 and 6, the filter 334 has a total surface area that is greater than a smallest cross-sectional area of the lid 306. In the lid 306, the smallest cross-sectional area is the cross-sectional area of lid opening 354. In some embodiments, more than one filter is coupled to the lid 306 in a similar manner as the filter 334. For example, in some embodiments, the filter 334 or an additional filter (not shown) can be coupled to the lower inner circumferential edge 368. That is, one or more filters 334 can be coupled to the lid 306 and positioned anywhere along the inner surface 353 of the lid 306. In embodiments employing more than one filter 334, the filters 334 can be similar to one another or different from one another. That is, the filters 334 can be formed of the same or different materials, and the filters 334 can have the same or sequentially smaller pore sizes.

As an example, a first filter 334 can be coupled to the upper inner circumferential edge 370 and can have a diameter of 56 mm, an element pore size of 80 μm, and can be at least partially surrounded by one or more retaining walls 372, while a second filter 334 can be coupled to the lower inner circumferential edge 368 and can have a diameter of 96 mm, an element pore size of 200 μm, and can be at least partially surrounded by the inner surface 353 of the lid 306.

Any of the above-described filters 134, 234 and 334 can be used in combination with one another in one sample preparation system. For example, as described above, the filter 134 can be used in combination with the filter 234 and/or the filter 334, to provide a series of filters for different applications, and/or for the removal of successively smaller particulates from the liquid composition.

Alternatively, or in addition, more than one of each type of filter 134, 234 or 334 can be employed (and in some embodiments, can be nested) for the removal of successively smaller particulates from the liquid composition. For example, the filters may be arranged where a coarse filter acts as a pre-filter with a larger pore size relative to subsequent filters, which have successively smaller pore sizes for the collection of a filtrate. The filters may be arranged for use of the sample preparation system in an upright position, and/or the filters may be arranged for use of the sample preparation system when it is tipped or inverted.

Figure 7:
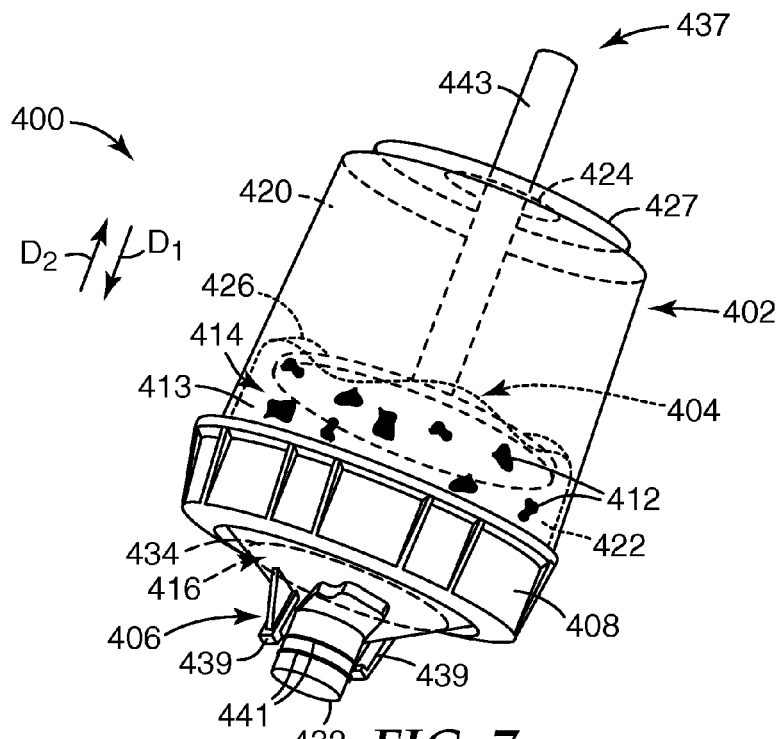
FIG. 7 is a perspective view of a sample preparation system according to another embodiment of the present disclosure.

FIG. 7 illustrates a sample preparation system 400 according to another embodiment of the present disclosure, wherein like numerals represent like elements. The sample preparation system 400 shares many of the same elements and features described above with reference to the illustrated embodiments of FIGS. 2-3 and 5-6. Accordingly, elements and features corresponding to elements and features in the illustrated embodiment of FIGS. 2-3 and 5-6 are provided with the same reference numerals in the 400 series. Reference is made to the description above accompanying FIGS. 2-3 and 5-6 for a more complete description of the features and elements (and alternatives to such features and elements) of the embodiment illustrated in FIG. 7.

The sample preparation system 400 includes a container 402 having a first reservoir 420, a liner 404 having a second reservoir 422 and dimensioned to be received in the first reservoir 420 of the container 402, a lid 406, a collar 408, and a plunger 437. The lid 406 is similar to that of lids 106, 206 and 306 described above and illustrated in FIGS. 2-6, but further includes two upwardly-extending projections 439, which allow the sample preparation system 400 to be coupled to other devices, or provide coupling means for a cover (not shown). The lid 406 includes a port 432, which includes a plurality of ridges 441 that can provide alternative or additional coupling means for coupling the sample preparation system 400 to a cover or other devices. The lid 406 further includes a filter 434 that is substantially similar to the filter 334 shown in FIGS. 5-6 and described above.

In some embodiments, as shown in FIG. 7, the plunger 437 is configured to apply positive pressure to the exterior of the liner 404 when the plunger 437 is moved in a first direction $D_1$ toward the top of the container 402. As shown in FIG. 7, when the plunger 437 is used to apply pressure to the exterior of the liner 404, the liner 404 is compressed, the volume in the second reservoir 422 is reduced, and a liquid composition 414 (including a source 412 and a diluent 413) is forced through the filter 434 to form a filtrate 416 that collects inside the lid 406 (e.g., when the sample preparation system 400 is inverted as shown in FIG. 7). The filtrate 416 can then be moved out of the sample preparation system 400 via the port 432.

In some embodiments, the plunger 437 is configured to apply negative pressure to the interior of the liner 404. For example, in some embodiments, the plunger 437 is coupled to the liner 404, such that when the plunger 437 is moved in a second direction $D_2$ opposite the first direction $D_1$, toward the bottom of the container 402, the liner 404 expands, which creates a reduced pressure in its interior (i.e., the second reservoir 422), and which establishes a pressure differential between the second reservoir 422 and the exterior of the sample preparation system 400. This pressure differential can cause fluid to move into the second reservoir 422 via the port 432, for example. As a result of the plunger 437 cooperating with the exterior of the liner 404 to create a pressure differential, the plunger 437 can be used without contacting the liquid composition 414 and can be reused without risk of contamination.

In some embodiments, as shown in FIG. 7, the plunger 437 can include a handle 443 that is dimensioned to be received in an aperture 424 of the base 427 of the container 402. In some embodiments, the handle 443 of the plunger 437 can be sized more closely to the size of the aperture 424, and/or a sealing means (e.g., an o-ring) can be positioned between the handle 443 and the aperture 424 to form a seal. In the embodiment illustrated in FIG. 7, the handle 443 has a smaller diameter than the portion of the plunger 437 that contacts the liner 404 (e.g., a base 426 of the liner 404). The portion of the plunger 437 that contacts the liner 404 is dimensioned to be received in the first reservoir 420 of the container 402. However, in some embodiments, the plunger 437 has a uniform cross-section or a gradually decreasing cross-section (e.g., in the second direction $D_2$), and the aperture 424 in the container 402 is sized accordingly. The plunger 437 shown in FIG. 7 is shown by way of example only, but one of ordinary skill in the art should understand that a variety of shapes and sizes of plungers can be used without departing from the spirit and scope of the present disclosure.

The plunger 437 can be formed of a variety of materials, including the materials listed above with respect to the container 102, and the plunger 437 can be solid or hollow. The plunger 437 can be translucent (or even transparent), or opaque, depending on the application of use.

Figure 8:
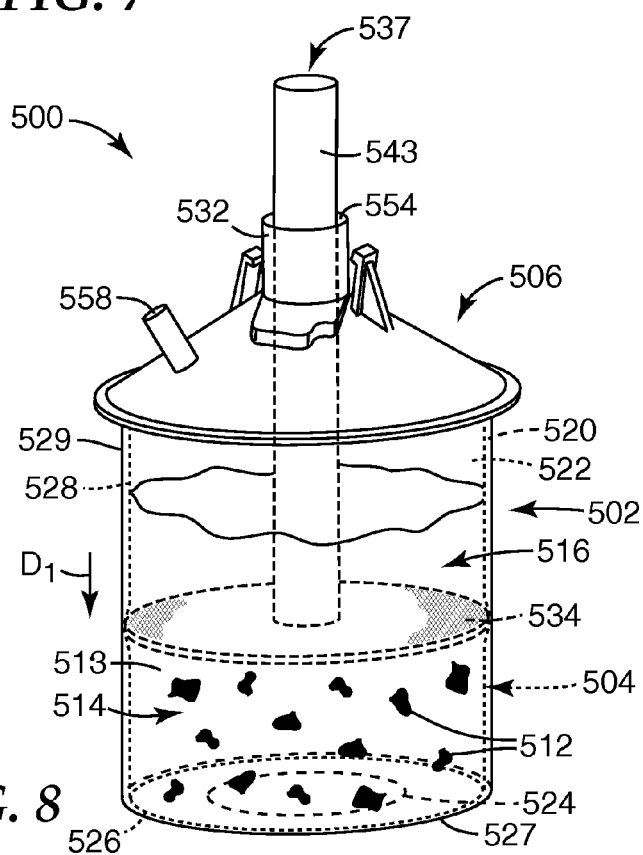
FIG. 8 is a perspective view of a sample preparation system according to another embodiment of the present disclosure.

FIG. 8 illustrates a sample preparation system 500 according to another embodiment of the present disclosure, wherein like numerals represent like elements. The sample preparation system 500 shares many of the same elements and features described above with reference to the illustrated embodiments of FIGS. 2-3 and 7. Accordingly, elements and features corresponding to elements and features in the illustrated embodiments of FIGS. 2-3 and 7 are provided with the same reference numerals in the 500 series. Reference is made to the description above accompanying FIGS. 2-3 and 7 for a more complete description of the features and elements (and alternatives to such features and elements) of the embodiment illustrated in FIG. 8.

As shown in FIG. 8, the sample preparation system 500 includes a container 502 that includes a first reservoir 520, a liner 504 dimensioned to be received in the first reservoir 520 and including a second reservoir 522, and a lid 506. A collar (not shown) can also be employed to further secure the components of the sample preparation system 500 together. The second reservoir 522 is adapted to contain a liquid composition 514 comprising a source 512 and a diluent 513. The sample preparation system 500 further includes a plunger 537 coupled to a filter 534. The filter 534 is adapted to filter the liquid composition 514 to form a filtrate 516 that comprises the analyte of interest (if present).

The container 502 includes a base 527, a sidewall 529, and an aperture 524 defined in the base 527. The liner 504 includes a sidewall 528 and a base 526 that can be accessed, for example, via the aperture 524 in the base 527 of the container 502. The lid 506 includes a port 532 that defines an opening 554 in the lid 506 and the sample preparation system 500. The plunger 537 includes a handle 543 that is dimensioned to be received in the port 532, such that the handle 543 can be accessed from outside of the sample preparation system 500 to force the filter 534 through the liquid composition 514. In some embodiments, the handle 543 of the plunger 537 can be sized more closely to the size of the opening 554, and/or a sealing means (e.g., an o-ring) can be positioned between the handle 543 and opening 554 to form a seal. The lid 506 further includes an off-axis aperture 558 defined in a second port of the lid 506, which can serve, for example, as a degassing outlet to allow for the release of pressure from within the sample preparation system 500.

In some embodiments, as shown in FIG. 8, the filter 534 can be dimensioned to fit within the second reservoir 522 of the liner 504. In such embodiments, the filter 534 can form a seal with the sidewall 528 of the liner 504 by virtue of the deformability of the liner 504 and does not necessarily require additional sealing means between the outer surface of the filter 534 and the inner surface of the sidewall 528 of the liner 504. The deformability of the liner 504 can also allow for wider tolerances, such that the filter 534 does not have to be sized within a narrow range to still be able to cooperate with the liner 504.

Alternatively, in some embodiments, the sample preparation system 500 does not include a liner 504, and the filter 534 can be configured to cooperate with the container 502. For example, the filter 534 can be sized to fit within the first reservoir 520 of the container 502. In some embodiments, the sample preparation system 500 can include sealing means (e.g., an o-ring) positioned between the filter 534 and the sidewall 529 of the container 502. In some embodiments, the sidewall 529 of the container 502 is straight up and down (i.e., perpendicular to the base 527) to facilitate sealing the filter 534 with the sidewall 529. In some embodiments, the filter 534 includes an outer deformable (e.g., elastomeric) flange to allow the filter 534 to accommodate a taper in the sidewall 529 of the container 502. Such a flange could also be incorporated into embodiments employing the filter 504.

As the plunger 537 is pressed downwardly along a direction $D_1$, the filter 534 moves downwardly through the liquid composition 514, such that relatively large insoluble matter (i.e., any particulates having a size greater than the pore size of the filter 534) are maintained below the filter 534, and any soluble matter and relatively small insoluble matter (i.e., any particulates having a size less than the pore size of the filter 534) pass through the filter, such that the filtrate 516 is formed above the filter 534 in the second reservoir 522. The plunger 537 can be pressed in the direction $D_1$ to a set position (e.g., the liner 504, the filter 534 and/or the plunger 537 can include one or more stops, the plunger 537 can be sized to only accommodate a certain depth in the second reservoir 522, etc.), or to a position where any remaining insoluble matter in the liquid composition 514 is at least partially compressed by the filter 534.

In some embodiments, the handle 543 of the plunger 537 can be hollow and in fluid communication with the second reservoir 522. In such embodiments, at least a portion of the filtrate 516 can be received in the interior of the handle 543 of the plunger 537 and can be removed from the sample preparation system 500 via the handle 543. In such embodiments, the plunger 537 can include a cover dimensioned to receive the upper end of the handle 543. Alternatively, the plunger 537 can be hollow and not covered at its base by the filter 534, such that at least a portion of the liquid composition 514 can be received in the interior of the handle 543 of the plunger 537. Such embodiments can allow the liquid composition 514 to take up less space in the bottom of the second reservoir 522 and can allow the filter 534 to be moved further down in the second reservoir 522 along the direction $D_1$.

FIGS. 9-12 illustrate a sample preparation system 600 according to another embodiment of the present disclosure, wherein like numerals represent like elements. The sample preparation system 600 shares many of the same elements and features described above with reference to the illustrated embodiment of FIGS. 2-3. Accordingly, elements and features corresponding to elements and features in the illustrated embodiment of FIGS. 2-3 are provided with the same reference numerals in the 600 series. Reference is made to the description above accompanying FIGS. 2-3 for a more complete description of the features and elements (and alternatives to such features and elements) of the embodiment illustrated in FIGS. 9-12.

Figure 9:
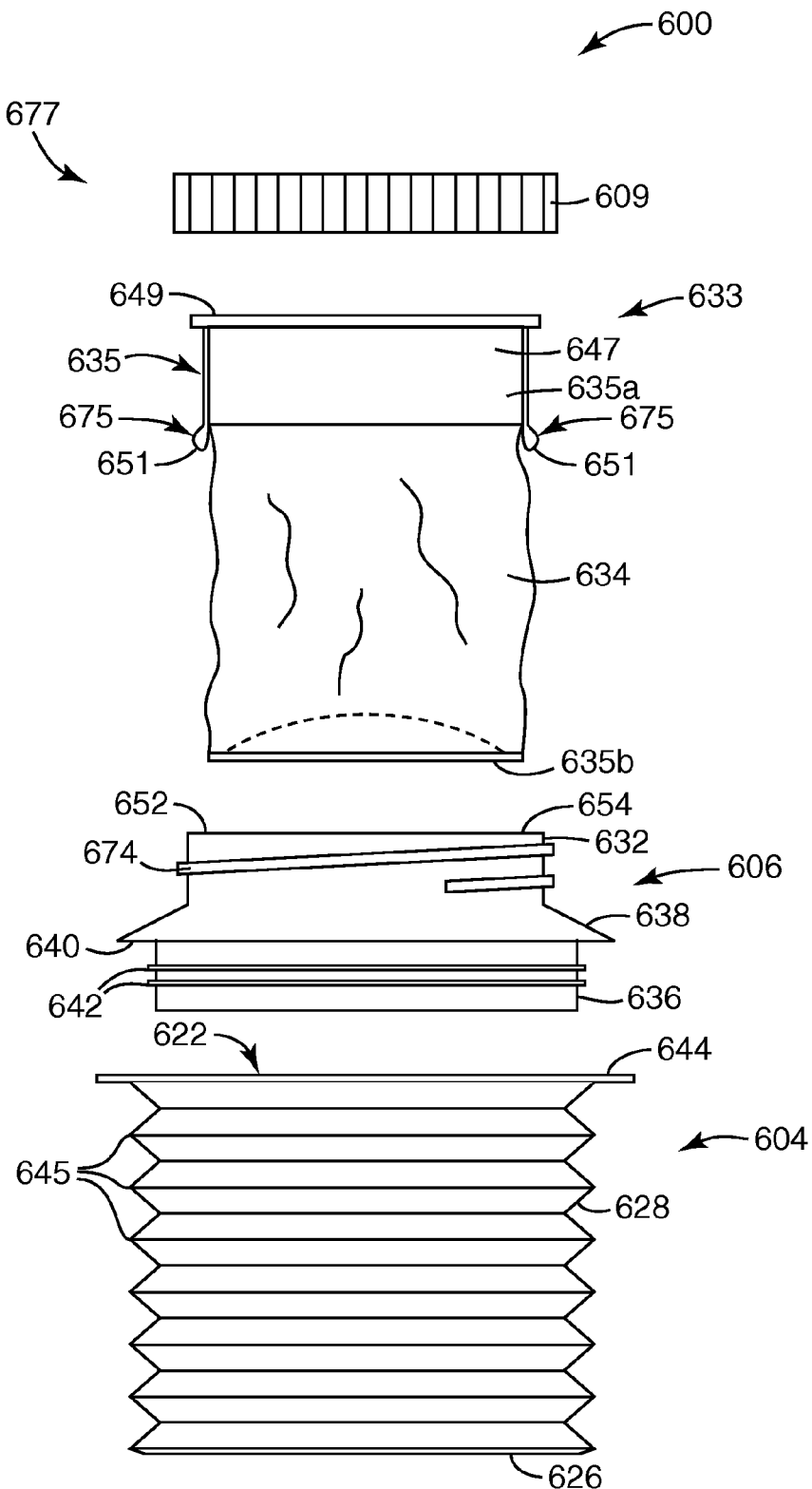
FIG. 9 is an exploded side view of a sample preparation system according to another embodiment of the present disclosure, the sample preparation system including a filter, and a lid assembly that includes a lid and a cover.

As shown in FIG. 9, the sample preparation system 600 includes a receptacle 604, a lid 606, a cover 609, and a filter assembly 633. The receptacle 604 is deformable, self-supporting and freestanding. The receptacle 604 includes a base 626 and a sidewall 628. The sidewall 628 includes an accordion-type configuration and includes a plurality of pleats or folds 645 (e.g., a plurality of annular pleats or folds 645) to allow the sidewall 628 to be folded at each pleat 645 and to facilitate the collapse of the receptacle 604 substantially along its longitudinal axis, and particularly, to facilitate the collapse of the receptacle 604 substantially uniformly substantially along its longitudinal axis. In the embodiment illustrated in FIG. 9, the sidewall 628 includes a plurality of pleats or folds 645 by way of example only. However, it should be understood that the sidewall 628 can include other structures that would allow the sidewall 628 to collapse substantially uniformly substantially along its longitudinal axis, such as annular weakened portions in the sidewall 628 that are less rigid and/or less thick than the remainder of the sidewall 628 to allow the sidewall 628 to buckle at the locations of the annular weakened portions. Other suitable structures are also possible and within the spirit and scope of the present disclosure.

The base 626 of the receptacle 604 can be reinforced, made of a more rigid material, and/or made to be thicker relative to the sidewall 628 to encourage the receptacle 604 to collapse along its longitudinal axis. The receptacle 604 includes a reservoir 622 that is adapted to contain a liquid composition that comprises a source and a diluent.

The receptacle 604 can be formed of a variety of materials, including the materials listed above with respect to the liner 104. The receptacle 604 can be translucent (or even transparent), or opaque, depending on the application of use. Any or all of the components of the sample preparation system 600 can be disposable (e.g., made for one-time use).

The lid 606 includes a port 632, which can be coupled to the filter assembly 633, a cylindrical portion 636 that is dimensioned to be received within the receptacle 604, and a generally conical (e.g., frusto-conical) portion 638 that extends from the cylindrical portion 636 to the port 632. At the junction between the cylindrical portion 636 and the conical portion 638, the lid 106 further includes a lip 640 that extends radially outwardly from the cylindrical portion 636 and the conical portion 638. The port 632 of the lid 606 is generally cylindrical and tubular in shape, such that the port 632 includes an inner surface 652 and defines an opening 654 in the lid 606, and in the sample preparation system 600, when assembled.

The cylindrical portion 636 of the lid 606 includes a plurality of circumferential outwardly-projecting protrusions 642 to allow the cylindrical portion 636 to be snap-fit or press-fit to the inner surface of the receptacle 604. The receptacle 604 can include an upper surface 644 that can form an abutting relationship with the lip 640 of the lid 606. The lid 606 and the receptacle 604 can be coupled together using any of the above removable or permanent coupling means in order to form a seal (e.g., a liquid-tight seal, a hermetic seal, or a combination thereof), such that the sample preparation system 600 is inhibited from leaking during normal operation. For example, the plurality of circumferential outwardly-projecting protrusions 642 can be ultrasonically-welded to the inner surface of the receptacle 604.

The filter assembly 633 includes a frame 635 and a filter 634. The frame 635 includes an upper portion 635a and a lower portion 635b, and the filter 634 is coupled therebetween. The upper portion 635a of the frame 635 is shaped and dimensioned to be coupled to the port 632 of the lid 606 and received within the port 632 of the lid 606 and the reservoir 622 of the receptacle 604. The frame 635 need not include the lower portion 635b, but the lower portion 635b gives the filter 634 additional weight and aids in exposing the filter 634 to the liquid composition in the reservoir 622 of the receptacle 604.

The upper portion 635a includes a tubular body 647 dimensioned to be received in the port 632 of the lid 606, a lip 649 coupled to the upper end of the tubular body 647 dimensioned to sit atop the port 632 of the lid 606, and a plurality of ribs 651. The ribs 651 are circumferentially-spaced about the tubular body 647. The embodiment illustrated in FIG. 9 includes two ribs 651, but as few or as many as necessary can be used. The ribs 651 are shaped to be coupled to the lid 606 in a snap-fit engagement. Particularly, the ribs 651 each include a cam surface 675 adapted to slide along the inner surface 652 of the port 632 as the upper portion 635a of the frame is moved into the port 632. In addition, the cam surface 675 of each rib 651 causes the respective rib 651 to be forced radially inwardly as the tubular body 647 is moved into the port 632, and further allows the respective rib 651 to snap (e.g., radially outwardly) into position under the bottom of the port 632 (i.e., on the inside of the lid 606).

The filter assembly 633 can then be removed from the lid 606 by pulling upwardly on the lip 649 of the frame 635 with sufficient force to move at least one rib 651 inwardly far enough to bring its cam surface 675 into contact with the inner surface 652 of the port 632, and to continue sliding the cam surface 675 upwardly along the inner surface 652 until the rib 651 is released from contact with the inner surface 652 of the port 632. Alternatively, the filter assembly 633 can be removed from the lid 606 by moving at least one rib 651 radially inwardly while applying an upward force to bring the cam surface 675 of the respective rib 651 into contact with the inner surface 652 of the port 632, or by squeezing the ribs 651 toward one another (e.g., radially inwardly) and moving the upper portion 635a of the frame 635 upwardly out of the port 632.

The filter 634 illustrated in FIG. 9 is collapsible and can be caused to hang downwardly in the reservoir 622 of the receptacle 604 at least partially by the weight of the lower portion 635b of the frame 635.

The cover 609 is shaped and dimensioned to receive at least a portion of the port 632. As a result, the cover 609 can be coupled to the port 632 of the lid 606 to close the opening 654 in the lid 606 and to seal (e.g., hermetically seal) the sample preparation system 600 from ambience. The cover 609 can be coupled to the lid 106 using any of the above-described coupling means. In the embodiment illustrated in FIG. 9, the port 632 of the lid 606 includes a plurality of threads 674 adapted to matingly engage with threads (not shown) on the inside of the cover 609, such that the cover 609 can be screwed onto the port 632. However, any of the other coupling means described above can be employed to couple the cover 609 to the lid 606 to close the opening 654 in the lid 606. The cover 609 and the lid 606 can together form a lid assembly 677, and the lip 649 of the filter assembly 633 can be sandwiched between the cover 609 and the upper end of the port 632 of the lid 606 when the sample preparation system 600 is assembled and closed.

Figure 10:
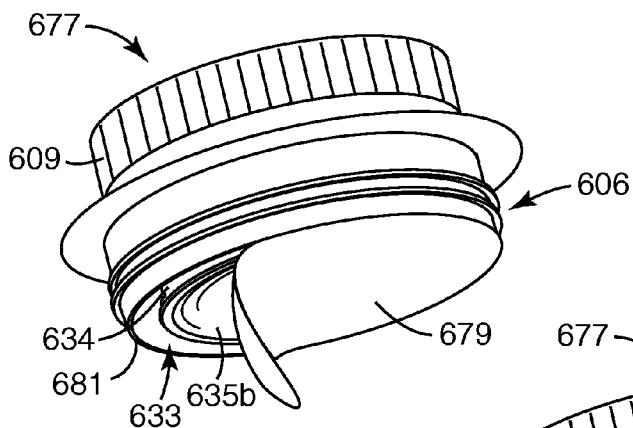
FIG. 10 is a perspective view of the lid assembly and filter of FIG. 9, with the filter in a compressed state.
Figure 11:
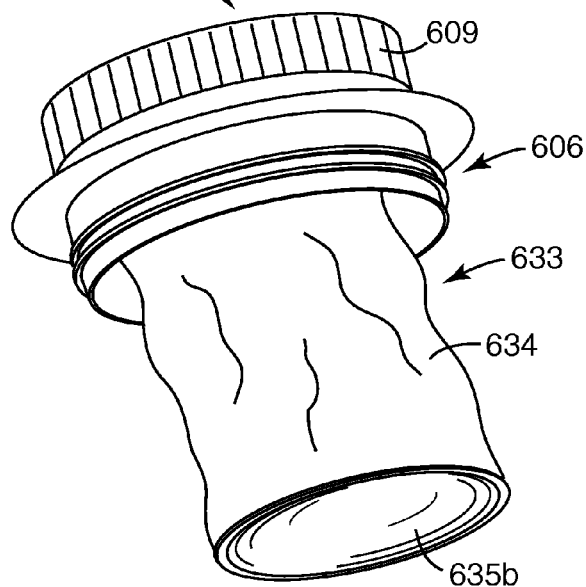
FIG. 11 is a perspective view of the lid assembly and filter of FIGS. 9 and 10, with the filter in an uncompressed state.

FIG. 10 illustrates the lid assembly 677 and the filter assembly 633 with the cover 609 coupled to the lid 606, and the filter assembly 633 coupled therebetween. The filter 634 is shown in a compressed state, such that the filter assembly 633 is contained in the interior of the lid 606. The lower portion 635b of the filter frame 635 is rigid relative to the collapsible filter 634, which aids in collapsing the filter 634 along its longitudinal axis, such that the filter 634 can be compressed into the interior of the lid 606 by pressing upwardly on the lower portion 635b of the frame 635. A removable barrier film 679 can be coupled to a lower surface 681 of the lid 606 to maintain the filter 634 in a compressed state within the interior of the lid 606. The lid assembly 677 can be sterilized and packaged with the filter 634 in its compressed state and the filter assembly 633 contained inside the lid 606 by the removable barrier film 679. A user can then remove the removable barrier film 679 prior to use (e.g., in a sterile environment) to allow the filter 634 (and the lower portion 635b of the frame 635, if employed) to hang below the lid assembly 677 in an uncompressed state. The removable barrier film 679 can also be removed just prior to coupling the lid 606 to the receptacle 604 to allow the filter 634 to drop into the reservoir 622 of the receptacle 604. The uncompressed state of the filter 634 following removal of the removable barrier film 679 is shown in FIG. 11.

The removable barrier film 679 can be coupled to the lid 606 using any of the coupling means described above, and can be formed of a variety of materials, including, but not limited to, a polyolefin, including, but not limited to polypropylene (e.g., low density polyethylene (LDPE)), polyethylene; poly (methylpentene); polyamide (e.g., NYLON®); compressed blown microfiber (cBMF); urethane; polyester; polycarbonate; and combinations thereof. In some embodiments, the removable barrier film 679 can include, for example, a heat sealed "strippable" film, such as a 3M™ SCOTCHPAK™ release liner (3M Company, St. Paul, Minn.). The removable barrier film 679 can be translucent (or even transparent), or opaque. The removable barrier film 679 can be formed by a variety of processes, including, but not limited to a molding process, extrusion, a blow film forming process, etc., and combinations thereof.

Figure 12:
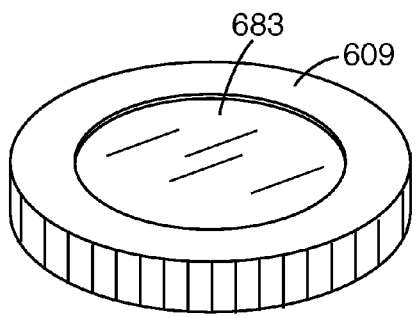
FIG. 12 is a top perspective view of the cover of FIGS. 9-11.

In some embodiments, as shown in FIG. 12, the cover 609 includes a frangible barrier 683 which can be punctured to access either the reservoir 622 of the receptacle 604, or the volume within the filter 634. The barrier 683 can include a membrane, a non-porous film, and combinations thereof. In addition, the frangible barrier 683 can be formed of a variety of materials that allow the barrier 683 to be frangible (e.g., punctured by a pipette tip), including, but not limited to, a polyolefin, including, but not limited to polypropylene (e.g., low density polyethylene (LDPE)), polyethylene; poly(methylpentene); polyamide (e.g., NYLON®); compressed blown microfiber (cBMF); urethane; polyester; polycarbonate; synthetic or natural elastomers; 3M™ TEGADERM™ film dressing (3M Company, St. Paul, Minn.), and combinations thereof. In some embodiments, the barrier 683 is instead formed over the opening 654 in the lid 606. In such embodiments, the cover 609 can be solid and can be used to cover the lid 606, for example, after the barrier 683 has been punctured, or the cover 609 can include an additional barrier. Alternatively, in embodiments in which the barrier 683 is formed over the opening 654 in the lid 606, a cover 609 need not be employed. Whether employed with the lid 606 or the cover 609, or both, or another portion of the sample preparation system 600, the barrier 683 can include the additional functionality of being gas-permeable to allow for gas exchange between the interior of the reservoir 622 and ambience (e.g., to provide oxygen to aerobic bacteria of interest).

Figure 13:
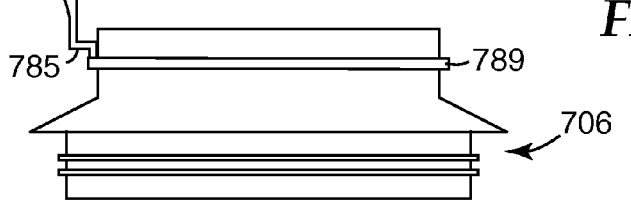
FIG. 13 is a side view of a lid assembly of a sample preparation system according to another embodiment of the present disclosure.

FIG. 13 illustrates a sample preparation system 700 according to another embodiment of the present disclosure. FIG. 13 shows only the lid assembly 777 of the sample preparation system 700. The other components of the sample preparation system 700 can be assumed to include any of the other respective components of the sample preparation systems described above and illustrated in FIGS. 2-12, and thus for simplicity, are not shown in FIG. 13.

The lid assembly 777 includes a lid 706 and a cover 709 coupled to the lid 706 via a hinge 785. In some embodiments, as shown in FIG. 13, the hinge 785 is a living hinge, and the cover 709 is integrally formed with the lid 706. In some embodiments, the hinge 785 is formed separately from one or both of the lid 706 and the cover 709. The cover 709 is a flip-top cover and can be coupled with the lid 706 via a snap-type engagement. In the embodiment illustrated in FIG. 13, the cover 709 includes a projection 787 that can be snapped onto a ridge 789 on the lid 706. The cover 709 can include other sealing means (e.g., an o-ring), such that when the cover 709 is closed over the lid 706, the cover 709 forms a seal (e.g., a liquid tight seal, a hermetic seal, etc.) with the lid 706.

Figure 14:
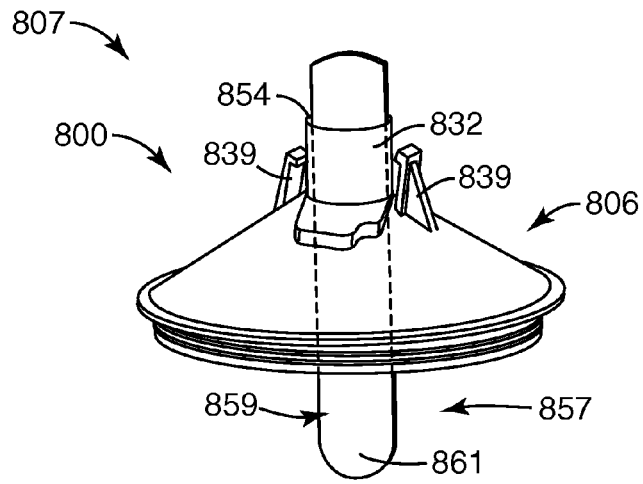
FIG. 14 is a perspective view of a sample preparation and collection system according to one embodiment of the present disclosure.

FIG. 14 illustrates a sample preparation and collection system 807 that includes a sample preparation system 800 and a sample collection system 857. For simplicity, FIG. 14 shows only a lid 806 of the sample preparation system 800. The other components of the sample preparation system 800 can be assumed to include any of the other respective components of the sample preparation systems described above and illustrated in FIGS. 2-13, and thus for simplicity, are not shown in FIG. 14.

The portion of the sample preparation system 800 that is shown shares many of the same elements and features described above with reference to the illustrated embodiments of FIGS. 2-3 and 7. Accordingly, elements and features corresponding to elements and features in the illustrated embodiments of FIGS. 2-3 and 7 are provided with the same reference numerals in the 800 series. Reference is made to the description above accompanying FIGS. 2-3 and 7 for a more complete description of the features and elements (and alternatives to such features and elements) of the embodiment illustrated in FIG. 14.

As shown in FIG. 14, the sample preparation system 800 includes a lid 806, and the sample collection system 857 is coupled to the lid 806 in such a way that the sample collection system 857 will be positioned in fluid communication with a reservoir of the sample preparation system 800 that is adapted to contain a liquid composition comprising a source and a diluent. The lid 806 includes a port 832 that defines an opening 854 into the interior of the lid 806 and the sample preparation system 800. The lid 806 further includes upwardly-extending projections 839 that can provide additional coupling means for the sample collection system 857.

In the embodiment illustrated in FIG. 14, the sample collection system 857 is coupled to the sample preparation system 800 via the port 832 of the lid 806 and includes a support 859 that is configured to extend downwardly from the lid 806 (e.g., to extend into a reservoir of the sample preparation system 800) to be in fluid communication with a liquid composition. In some embodiments, the sample preparation system 800 can include a filter positioned to allow the support 859 to be in fluid communication with a filtrate of the liquid composition. For example, the sample preparation system 800 can include a filter designed to retain and hold the liquid composition, similar to the filter 234 described above and illustrated in FIG. 4, or the filter can be designed to retain the liquid composition in one portion of a reservoir of the sample preparation system 800, similar to the filter 534 described above and illustrated in FIG. 8, such that the support 859 can extend downwardly from the lid 806 to be in fluid communication with the filtrate.

The support 859 can be adapted to capture (e.g., reversibly capture) at least one analyte of interest from a liquid composition (or filtrate), if the analyte of interest is present in the liquid composition via any of the bonds or interactions described below. As mentioned above, a diluent used in the liquid composition can include enrichment media for a specific analyte of interest or the enrichment media can be coated or adsorbed to an inner surface of the sample preparation system 800 to grow the analyte(s) of interest and, optionally, inhibit the growth of analyte(s) in the liquid composition that are not of interest. The sample preparation and collection system 807 can further be incubated at a desired temperature to promote the growth of the analyte(s) of interest.

Whether the analyte(s) of interest are enriched or the sample preparation and collection system 807 is incubated to increase the amount of the analyte(s) of interest in the liquid composition, the support 859 can be adapted to capture the analyte(s) of interest from the liquid composition. The liquid composition and/or the sample preparation and collection system 807 (or a portion thereof) can be agitated to facilitate bringing the support 859 into contact with the liquid composition, or the sample preparation and collection system 807 can be tipped or inverted to bring the liquid composition into contact with the support 859. Furthermore, in embodiments in which the sample preparation system 800 employs a liner (or a deformable self-supporting receptacle), pressure can be applied to the liner (e.g., positive pressure can be applied to the exterior of the liner or negative pressure can be applied to the interior of the liner) to move the liquid composition into contact with the support 859.

In addition, as mentioned above, the liquid composition can be filtered, and the support 859 can be positioned in fluid communication with the filtrate. In addition, detergent or other cell lysing agents can be added to the diluent or the liquid composition to lyse cells that may be present in the liquid composition, or that may have been produced as a result of enrichment and/or incubation.

The support 859 can be adapted to capture at least one analyte of interest, such that the sample collection system 857 provides specific capture of one or more analytes of interest. For example, various moieties can be immobilized (e.g., coated, adsorbed, etc.) onto an outer surface 861 of the support 859 that are adapted to bind with one or more analytes of interest. The term "bind" and derivatives thereof generally refers to a variety of chemical bonds or interactions, including, but not limited to, covalent bonds (e.g., polar covalent bonds), ionic bonds, noncovalent bonds, metallic bonds, intermolecular interactions, and combinations thereof. Examples of noncovalent bonds include, but are not limited to, hydrogen bonds (e.g., in complementary nucleic acid sequences), dipole-dipole interactions, van der Waal's forces, electrostatic interactions, hydrophobic interactions, and combinations thereof. Intermolecular interactions can include a variety of the above-described bonds and/or interactions and can include, but are not limited to protein-protein interactions, peptide-peptide interactions, complementary nucleic acid sequences, antigen-antibody complexes, carbohydrate complexes, and combinations thereof.

In some embodiments, the support 859 can be functionalized with a variety of molecules or moieties including, but not limited to, antibodies, nucleic acid sequences, polysaccharides, carbohydrates, lipids, charged moieties or molecules, peptides, proteins (e.g., avidin/streptavidin, biotin), receptors, and combinations thereof. For example, in the embodiment illustrated in FIG. 14, the support 859 can include antibodies immobilized to its outer surface 861 that are capable of forming an antigen-antibody complex with *Salmonella* spp. (e.g., the support 859 can include a 3M™ TECRA® *Salmonella* Immunocapture support (available from 3M Microbiology, 3M Company, St. Paul, Minn.)).

In some embodiments employing the port 832, as shown in FIG. 14, at least a portion of the support 859 can be dimensioned to be received in the port 832. In the embodiment illustrated in FIG. 14, the support 859 is generally planar and has a width similar to the diameter of the port 832 to facilitate coupling the support 859 to the port 832. However, the support 859 in FIG. 14 is shown by way of example only, and one of ordinary skill in the art should understand that the support 859 can take on a variety of shapes (including a variety of cross-sectional shapes) and forms without departing from the spirit and scope of the present disclosure. For example, the support 859 can instead be generally cylindrical in shape. In addition, in the embodiment illustrated in FIG. 14, the support 859 has a length greater than its width to allow it to be positioned in the port 832, while allowing it to be able to extend below the bottom of the lid 806, and particularly, below a bottom of the lid 806 that is adapted to be coupled to a container and/or a liner. However, the proportions of the support 859 are shown in FIG. 14 by way of example only, and one or ordinary skill in the art should understand that the support 859 could instead be coupled to a different portion of the lid 806 or another component or portion of the sample preparation system 800 and can include a different shape having different proportions, without departing from the spirit and scope of the present disclosure. For example, in some embodiments, the support 859 can be coupled to an inner surface of the lid 806 below the port 832, and the support 859 can be dimensioned more closely to the diameter of a container and/or liner to which the lid 806 is coupled, rather than being dimensioned to fit in the port 832.

Furthermore, in some embodiments, the support 859 can be hollow, and an inner surface of the support 859, in addition to or in lieu of its outer surface 861, can be functionalized to capture the analyte(s) of interest. In addition, in some embodiments, the support 859 can include one or more fluidic channels, a porous material or a collection filter (such as those described in greater detail below).

The support 859 can be formed of a variety of materials, including, but not limited to, one or more of polymers (e.g., polycarbonate, polyester, etc., combinations thereof), composites, elastomers, porous materials (e.g., cellulosics), ceramics (e.g., ceramic membranes or ceramic membrane filters), any of the materials described above with respect to the filter 134, and combinations thereof.

In use, following any of the above-described agitation, enrichment, incubation, lysing, and/or filtering steps, the lid 806 can be decoupled from the other components of the sample preparation system 800, and any analyte(s) of interest that has been collected by the support 859 can be eluted into a new receptacle, for example, using an elution solution adapted to disrupt the bond or interaction between the analyte(s) of interest and the moieties or molecules immobilized on the support 859, or a lysis reagent to lyse cells captured by the support 859. A variety of elution solutions known in the art can be used and can be specific to the interaction at hand, or can be a general nonspecific elution solution that is capable of disrupting a variety of bonds and interactions.

Any analyte(s) of interest collected by the support 859 can be eluted into a new receptacle, device or system for a variety of downstream processes. For example, the analyte(s) of interest can be eluted into a test tube, a centrifugation tube, a flask, a fresh sample preparation system, a culture device, or another receptacle for further processing, including, but not limited to, concentration, incubation, enrichment, analysis, etc. Alternatively, or in addition, the analyte(s) of interest can be eluted into a detection system adapted to identify and/or quantitate the analyte(s) of interest.

In some embodiments, the lid 806 and the sample collection system 857 can be coupled to the mating components of another sample preparation system in which the reservoir of a container or liner has been filled with a fresh diluent (e.g., an elution solution and/or enrichment media), such that when the lid 806 is coupled to the new sample preparation system, the support 859 is positioned in fluid communication with the reservoir of that sample preparation system and the media contained therein.

Because the support 859 is functionalized for specific capture of the analyte(s) of interest, the sample collection system 857 is configured to collect a sample from the sample preparation system 800 that includes substantially only the analyte(s) of interest. Other contaminants from the liquid composition, particularly contaminants having similar functionalities/moieties as the analyte(s) of interest, may be present in the sample collected, but the sample collection system 857 is designed to capture substantially only the analyte(s) of interest.

Figure 15:
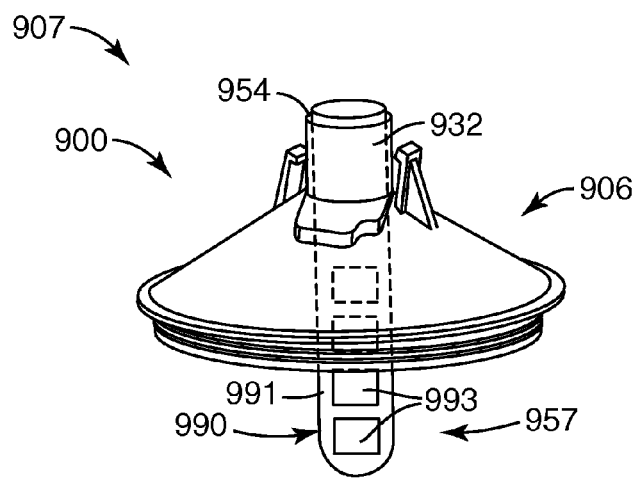
FIG. 15 is a perspective view of a sample preparation and collection system according to another embodiment of the present disclosure.

FIG. 15 illustrates a sample preparation and collection system 907 according to another embodiment of the present disclosure, wherein like numerals represent like elements. For simplicity, FIG. 15 shows only a lid 906 of the sample preparation system 900. The sample preparation and collection system 907 shares many of the same elements and features described above with reference to the illustrated embodiment of FIG. 14. Accordingly, elements and features corresponding to elements and features in the illustrated embodiment of FIG. 14 are provided with the same reference numerals in the 900 series. Reference is made to the description above accompanying FIG. 14 for a more complete description of the features and elements (and alternatives to such features and elements) of the embodiment illustrated in FIG. 15.

The sample preparation and collection system 907 includes a sample preparation system 900 and a sample collection system 957 coupled to the sample preparation system 900, and particularly, to the lid 906. The sample collection system 957 includes a capsule 990 having a hollow interior 991. The sample collection system 957 further includes one or more magnets 993 positioned with the interior 991 of the capsule 990. The magnets 993 can be used to capture analyte(s) of interest that have been magnetized, for example, by being allowed to interact with magnets (e.g., magnetic beads) that are functionalized to bind or interact with the analyte(s) of interest. Examples of suitable magnetic beads or particles include, but are not limited to, DYNAL® DYNABEADS® (Invitrogen, Inc., Carlsbad, Calif.), MAGNABINDO Streptavidin Beads (Pierce Biotechnology, Inc., Rockford, Ill.), etc., and combinations thereof.

Magnets can be used to capture analytes of interest, for example, when paramagnetic beads that have been functionalized with molecule or moieties known to bind or interact with the analyte of interest (e.g., with antibodies, steptavidin, etc.) are added to the source and/or liquid composition. For example, paramagnetic beads that have been functionalized with oligonucleotide capture probes can be added to a liquid composition to capture any nucleic acids having a nucleic acid sequence that is complementary to the probe. The same paramagnetic beads that are capable of capturing the nucleic acids of interest from the liquid composition will be attracted to the magnets 993 in the capsule 990 and will be collected from the liquid composition by the sample collection system 957. Alternatively, the functionalized paramagnetic beads can first be immobilized against the capsule 990 by virtue of their magnetic attraction to the magnets 993, and then the sample collection system 957 can be placed in fluid communication with the liquid composition. The collected nucleic acid sequences of interest can then be removed from the sample collection system 957 (e.g., by elution), transferred to another receptacle, device or system, and/or further processed (e.g., resuspended, concentrated, analyzed, etc.). The capture of nucleic acids is described above by way of example only; however, the magnetic beads can exploit any of the above-described bonds or interactions. For example, in some embodiments, the magnetic beads are functionalized with antibodies and form an antibody-antigen complex with the analyte(s) of interest, and in some embodiments, the magnetic beads form an electrostatic (charge-charge) interaction with the analyte(s) of interest.

The capsule 990 is shown in FIG. 15 as being coupled to a port 932 of the lid 906 and as being dimensioned to be received in the port 932, and particularly, in an opening 954 defined in the port 932. However, the sample collection system 957 and the capsule 990 is shown in FIG. 15 by way of example only, and it should be understood that the capsule 990 can have a variety of sizes and proportions and can be coupled to other portions of the lid 906 or other components of the sample preparation system 900 without departing from the spirit and scope of the present disclosure.

In use, the liquid composition and/or the sample preparation and collection system 907 can be agitated to facilitate bringing the liquid composition into contact with the sample collection system 957. The sample preparation and collection system 907 can also be tipped or inverted to bring the liquid composition into contact with the sample collection system 957. Furthermore, in embodiments in which the sample preparation system 900 employs a liner (or a deformable self-supporting receptacle), pressure can be applied to the liner (e.g., positive pressure can be applied to the exterior of the liner or negative pressure can be applied to the interior of the liner) to move the liquid composition into contact with the capsule 990 of the sample collection system 957.

Because the capsule 990 is adapted for magnetic capture of the analyte(s) of interest, the sample collection system 957 is configured to collect a sample from the sample preparation system 900 that includes substantially only the analyte(s) of interest. Other contaminants from the liquid composition, particularly contaminants having similar functionalities/moieties as the analyte(s) of interest (e.g., that may have become magnetized), may be present in the sample collected, but the sample collection system 957 is designed to capture substantially only the analyte(s) of interest.

In addition, in the embodiment illustrated in FIG. 15, the capsule 990 includes two closed ends. However, in some embodiments, the capsule 990 includes an open upper end, such that the interior 991 of the capsule 990 can be accessed for positioning of and removal of the magnets 993. Furthermore, in some embodiments, the magnets 993 are electromagnets, and the magnets are coupled (e.g., via an open upper end of the capsule 990) to an electrical circuit. In some embodiments, the magnets 993 comprises rare-earth magnets. In embodiments employing a capsule 990 having an open upper end, the sample preparation and collection system 907 can include a cover (not shown) that can be dimensioned to be coupled to the open upper end of the capsule 990 via any of the above-described removable, permanent or semi-permanent coupling means. In some embodiments, the sample collection system 957 functions by employing magnets, but does not include a capsule 990. That is, in some embodiments, the sample collection system 957 includes a magnet that is coupled to a portion of the sample preparation system 900 without being contained within any type of capsule.

The capsule 990 can be formed of a variety of materials, including, but not limited to, one or more of polymers, metals (e.g., non-magnetic metals), ceramics, composites, glass, elastomers, and combinations thereof.

Figure 16:
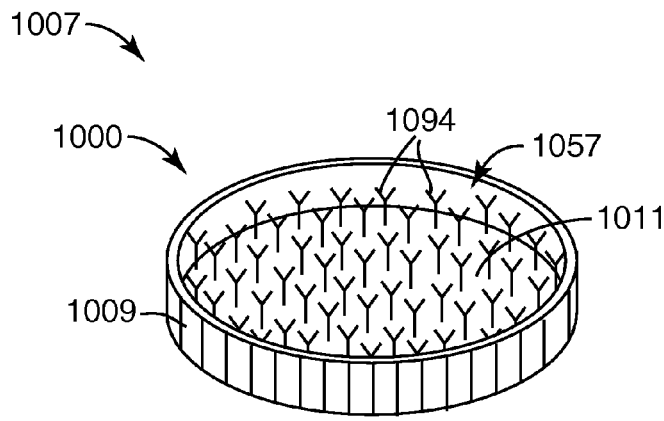
FIG. 16 is a schematic perspective view of a sample preparation and collection system according to another embodiment of the present disclosure.

FIG. 16 illustrates a sample preparation and collection system 1007 that includes a sample preparation system 1000 and a sample collection system 1057. For simplicity, FIG. 16 shows only a cover 1009 of the sample preparation system 1000. The other components of the sample preparation system 1000 can be assumed to include any of the other respective components of the sample preparation systems described above and illustrated in FIGS. 2-13, and thus for simplicity, are not shown in FIG. 16. However, by way of example only, the sample preparation system 1000 can be assumed to be the same as that of the sample preparation system 600 described above and illustrated in FIGS. 9-12.

The sample collection system 1057 includes one or more antibodies 1094 that are coupled to the cover 1009 of the sample preparation system 1000. Particularly, in the embodiments illustrated in FIG. 16, the antibodies 1094 have been coupled to (i.e., immobilized onto) an inner surface 1011 of the cover 1009. The antibodies 1094 can be adapted to form an antigen-antibody complex with the analyte(s) of interest, and the sample collection system 1057 can be positioned in fluid communication with a reservoir of the sample preparation system 1000 when the cover 1009 is coupled to a lid, a container, and/or a liner of the sample preparation system 1000.

In use, the sample preparation and collection system 1007 can be used to prepare a liquid composition comprising a source and a diluent, and the sample preparation and collection system 1007 can be closed with the cover 1009 of the sample preparation system 1000 to position the sample collection system 1057 in fluid communication with a reservoir of the sample preparation system 1000 containing the liquid composition, such that the antibodies 1094 can capture the analyte(s) of interest from the liquid composition, or a filtrate thereof. For example, a filter similar to that of the filter 634 described above and illustrated in FIGS. 9-11 can be employed in the sample preparation system 1000 to pre-filter the liquid composition.

Because the antibodies 1094 are adapted for specific capture of the analyte(s) of interest, the sample collection system 1057 is configured to collect a sample from the sample preparation system 1000 that includes substantially only the analyte(s) of interest. Other contaminants, particularly contaminants having similar functionalities/moieties as the analyte(s) of interest, may be present in the sample collected, but the sample collection system 1057 is designed to capture substantially only the analyte(s) of interest.

In addition, the liquid composition and/or the sample preparation and collection system 1007 can be agitated to facilitate bringing the liquid composition into contact with the sample collection system 1057. In addition, the sample preparation and collection system 1007 can be tipped or inverted to bring the liquid composition into contact with the sample collection system 1057. Furthermore, in embodiments in which the sample preparation system 1000 employs a liner, pressure can be applied to the liner (e.g., positive pressure can be applied to the exterior of the liner or negative pressure can be applied to the interior of the liner) to move the liquid composition into contact with the antibodies 1094 of the sample collection system 1057.

After the liquid composition has been allowed to interact with the antibodies 1094 of the sample collection system 1057, the cover 1009 can be removed from the remainder of the sample preparation system 1000, and any captured analyte(s) of interest can be removed from the antibodies 1094 of the sample collection system 1057 (e.g., by elution), transferred to another receptacle, device or system, and/or further processed (e.g., resuspended, concentrated, enriched, incubated, analyzed, lysed, etc.).

The sample collection system 1057, and particularly, the antibodies 1094 are illustrated in FIG. 16 as being coupled to the inner surface 1011 of the cover 1009. However, it should be understood that the antibodies 1094 can be instead be coupled to one or more of the other components of the sample preparation system 1000 without departing from the spirit and scope of the present disclosure.

As mentioned above, FIG. 17 illustrates a sample preparation and collection system 1107 according to one embodiment of the present disclosure. The sample preparation system 1100 shares many of the same elements and features described above with reference to the illustrated embodiments of FIGS. 2-3 and 7. Accordingly, elements and features corresponding to elements and features in the illustrated embodiments of FIGS. 2-3 and 7 are provided with the same reference numerals in the 1100 series. Reference is made to the description above accompanying FIGS. 2-3 and 7 for a more complete description of the features and elements (and alternatives to such features and elements) of the embodiment illustrated in FIG. 17.

The sample collection system 1157 is coupled to the sample preparation system 1100, such that the sample collection system 1157 is in fluid communication with the sample preparation system 1100, and such that a fluid path 1192 is defined at least partially by the sample preparation system 1100 and the sample collection system 1157. The fluid path 1192 allows a liquid composition, its filtrate, or a portion of the liquid composition or filtrate to be moved from the sample preparation system 1100 to the sample collection system 1157 by moving in the fluid path 1192 and not being exposed to ambience during the transfer between the sample preparation system 1100 and the sample collection system 1157.

In the sample preparation and collection systems 807, 907 and 1007 described above and illustrated in FIGS. 14-16, the sample collection system 857, 957, 1057 is positioned to be in fluid communication with a reservoir of the sample preparation system 800, 900, 1000, such that a fluid path can be thought to be at least partially defined by the sample preparation system 800, 900, 1000 and the respective sample collection system 857, 957, 1057. However, because the sample collection system 857, 957, 1057 is generally positioned within the interior of the sample preparation system 800, 900, 1000, transfer of a sample from the sample preparation system 800, 900, 1000 to the respective sample collection system 857, 957, 1057 is not necessarily required. Still, the sample preparation and collection systems 807, 907 and 1007 can also be thought to provide means for preparing and collecting a sample without necessarily exposing the sample to ambience, or at least not until after the collection process.

In some embodiments, the phrase "without exposing to ambience" and derivations thereof refers to not removing a sample (i.e., at least a portion of the liquid composition or filtrate) during the transfer between the sample preparation system and the sample collection system (e.g., to prevent spills or contamination), such that the sample remains in the fluid path 1192 of the sample preparation and collection system 1107 from preparation to collection, or even to another downstream step, but does not necessarily mean that the sample preparation and collection system 1107 is closed to gas-exchange or that other liquids cannot get into the sample preparation and collection system 1107. For example, in some embodiments, a lid, a cover, a container and/or a liner, or a portion thereof, is gas-permeable, or includes a gas-permeable film or membrane (e.g., for aerobic bacteria to continue to have access to oxygen).

In some embodiments, a plurality of sample preparation systems 1100 can be coupled to and in fluid communication with the same sample collection system 1157, such that samples from the plurality of sample preparation systems 1100 are pooled together prior to collection or any downstream analysis or further processing.

The sample preparation system 1100 includes a container 1102 having a first reservoir 1120, a liner 1104 having a second reservoir 1122 and dimensioned to be received in the first reservoir 1120 of the container 1102, and a lid 1106. The sample preparation system 1100 can also include a collar (not shown) to further secure the components of the sample preparation system 1100 together. The second reservoir 1122 is adapted to contain a liquid composition 1114 comprising a source 1112 and a diluent 1113.

The lid 1106 includes two upwardly-extending projections 1139 to which the sample collection system 1157 is coupled. The lid 1106 further includes a port which is substantially similar to the port 432 described above and illustrated in FIG. 7 and which is not shown in FIG. 17, because the sample collection system 1157 is coupled to the lid 1106 of the sample preparation system 1100 and, particularly, is coupled over the port and to the upwardly-extending projections 1139 of the lid 1106. The lid 1106 further includes a filter 1134 that is substantially similar to the filter 334 shown in FIGS. 5-6 and described above. The filter 1134 is adapted to filter the liquid composition 1114 to form a filtrate 1116 that comprises the analyte of interest (if present). However, it should be understood that the filter 1134 can take on any of the previously-described forms instead.

As shown in FIG. 17, the sample collection system 1157 is shaped and dimensioned to be coupled to the port and the upwardly-extending projections 1139 of the lid 1106. The sample collection system 1157 is shown in greater detail in FIG. 18. The sample collection system 1157 includes a housing 1196, an inlet 1186, and an outlet 1188. The housing 1196 includes a first portion 1196a, a second portion 1196b, and a third portion 1196c. The first, second and third portions 1196a, 1196b and 1196c can be coupled together by any of the above-described coupling means, or two or more of the first, second and third portions 1196a, 1196b and 1196c can be integrally formed. The housing 1196 includes a bore 1197 and an inner surface 1198, each of which is defined at least partially by the first portion 1196a and the second portion 1196b of the housing 1196.

The third portion 1196c includes one or more apertures 1182 in fluid communication with the bore 1197 and a seat 1199 positioned upstream of the apertures 1182 in which a collection filter 1184 can be positioned. Alternatively, the seat 1199 can be formed between the third portion 1196c and the second portion 1196b. The collection filter 1184 can be sized and/or functionalized to collect the analyte(s) of interest. In addition, a filter support (e.g., a mesh, such as a wire mesh, or other similar structure) can be positioned in the seat 1199 to support the collection filter 1184 and inhibit the collection filter 1184 from being displaced from the seat 1199 during operation. The filter support can also include a plurality of pores or apertures so as not to significantly disrupt the fluid flow through the sample collection system 1157. In some embodiments in which the collection filter 1184 is adapted to collect the analyte(s) of interest based on size, the collection filter 1184 can have an average pore size of less than 1 μm.

In some embodiments, the third portion 1196c is removably coupled to the second portion 1196b to allow the collection filter 1184 to be removed from the sample collection system 1157, e.g., to retrieve the collected analyte(s) of interest, to replace the collection filter 1184, etc. In the embodiment illustrated in FIG. 18, the third portion 1196c is coupled to the second portion 1196b via a screw-type engagement, and an inner surface of the third portion 1196c and an outer surface of the second portion 1196b include mating threads. However, it should be understood that the third portion 1196c can be coupled to the second portion 1196b using any of the above-described coupling means.

The inner surface 1198 of the housing 1196 can be coupled to the port of the sample preparation system 1100 by any of the coupling means described above, for example, by press-fit engagement with. By way of example, the port can include one or more ridges similar to the ridges 441 described above and illustrated in FIG. 7 to facilitate a press-fit or snap-fit engagement with the inner surface 1198 of the housing 1196. Alternatively, or in addition, the inner surface 1198 can include one or more mating structures, such as ribs or ridges to matingly engage with the outer surface (and/or any coupling structures formed thereon) of the port of the lid 1106.

The housing 1196 further includes one or more projections or threads 1195 adapted to allow the sample collection system 1157 to be screwed onto the port of the sample preparation system 1100 and secured underneath a radially-inwardly projecting portion of each of the projections 1139 of the lid 1106. The embodiment illustrated FIGS. 17 and 18 includes two threads spaced apart circumferentially to allow the sample collection system 1157 to be moved downwardly over the port of the lid 1106 (e.g., with both of the threads 1195 positioned out of contact with the projections 1139) and then rotated with respect to the lid 1106 to allow each of the radially-inwardly projecting portions of the projections 1139 to cam along an upper surface of one of the threads 1195 until the sample collection system 1157 is secured under the projections 1139 of the lid 1106 (e.g., such that the sample collection system 1157 is inhibited from being pulled from the sample preparation system 1100, and from being rotated either relative to the sample preparation system 1100 any further in the same direction, or in the opposite direction without sufficient force).

The housing 1196 can be formed of a variety of materials, including any of the materials listed above with respect to the container 102 and the collar 108.

The bore 1197 and the apertures 1182 define at least a portion of the fluid path 1192, such that the inlet 1186 can be in fluid communication with the sample preparation system 1100. The container 1102 of the sample preparation system 1100 includes a base 1127, and an aperture 1124 defined in the base 1127. Pressure can be applied to the liner 1104 (e.g., positive pressure can be applied to the exterior of the liner 1104 (e.g., to a base 1126 of the liner 1104, e.g., via the aperture 1124 in the base 1127 of the container 1102) or negative pressure can be applied to the interior of the liner 1104) to move the liquid composition through the filter 1134 and into the sample collection system 1157. In embodiments employing the filter 1134, the filter 1134 can function as a pre-filter to remove unwanted relatively large insoluble matter (e.g., large particles or debris) from the liquid composition 1114. Pre-filtering the liquid composition 1114 can be advantageous to enhance the purity of the material passing through the sample collection system 1157 and enhance the capture of the analyte(s) of interest. In addition, pre-filtering can help avoid clogging any portion of the sample collection system 1157 or other downstream devices, but pre-filtering is not necessary, and in some embodiments, the liquid composition 1114 will be moved into the sample collection system 1157 without being pre-filtered.

In some embodiments, negative pressure can be applied to the interior (e.g., the second reservoir 1122) of the liner 1104 by applying a vacuum to the outlet 1188 of the of the sample collection system 1157, which can be accomplished by fluidly coupling the third portion 1196c of the housing 1196 to a vacuum source, such as mechanical pump that creates a reduced pressure, or a manual pump such as a syringe-plunger combination. When negative pressure is applied to the outlet 1188 of the sample collection system 1157, the liquid composition 1114 is moved through the filter 1134 (optionally) to form a filtrate 1116, and the filtrate 1116 is forced through the sample collection system 1157, particularly, through the bore 1197 and the apertures 1182. As the filtrate 1116 passes through the collection filter 1184, the analyte(s) of interest can be trapped in the collection filter 1184, and the portions of the filtrate 1116 that are not trapped by the collection filter 1184 can pass through the collection filter 1184, and optionally to waste or another receptacle. For example, the housing 1196 can be fluidly coupled to a vacuum source via a receptacle adapted to collect the portions of the filtrate 1116 that pass through the collection filter 1184. The sample preparation system 1100 can further include an aperture 1158 which can function as a vent during suction, or to which a port or valve can be coupled. Alternatively, the liner 1104 can deform in response to the negative pressure and the suction can continue until the liner 1104 has collapsed.

In some embodiments, the sample collection system 1157, or at least a portion thereof, can be coupled to another portion of the sample preparation system 1100, such as the base 1127 of the container 1102 (e.g., via the aperture 1124 in the base 1127; such embodiments may not employ a liner 1104). In such embodiments, at least a portion of the container 1102 can be removable to facilitate coupling the sample collection system 1157 to the sample preparation system 1100 and/or removing the sample collection system 1157, or a portion thereof (e.g., the collection filter 1184).

In some embodiments, one or more portions or components of the sample preparation and collection system 1107 can include means for agitating the liquid composition 1114 and/or the filtrate 1116. For example, in some embodiments, the lid 1106, the container 1102 and/or the liner 1104 can include one or more means for agitating the liquid composition. By way of example only, in some embodiments, the sample preparation and collection system 1107 can include a first lid (or other removable portion of the sample preparation system 1100) that includes means for agitating the liquid composition 1114, and a second lid 1106, as shown in FIG. 17, that can be coupled to the sample collection system 1157. In such embodiments, the first lid can be coupled to the container 1102 and/or the liner 1104 to agitate the liquid composition 1114, and then the first lid can be replaced with the second lid 1106 of FIG. 17 to collect one or more analytes of interest.

Figure 26:
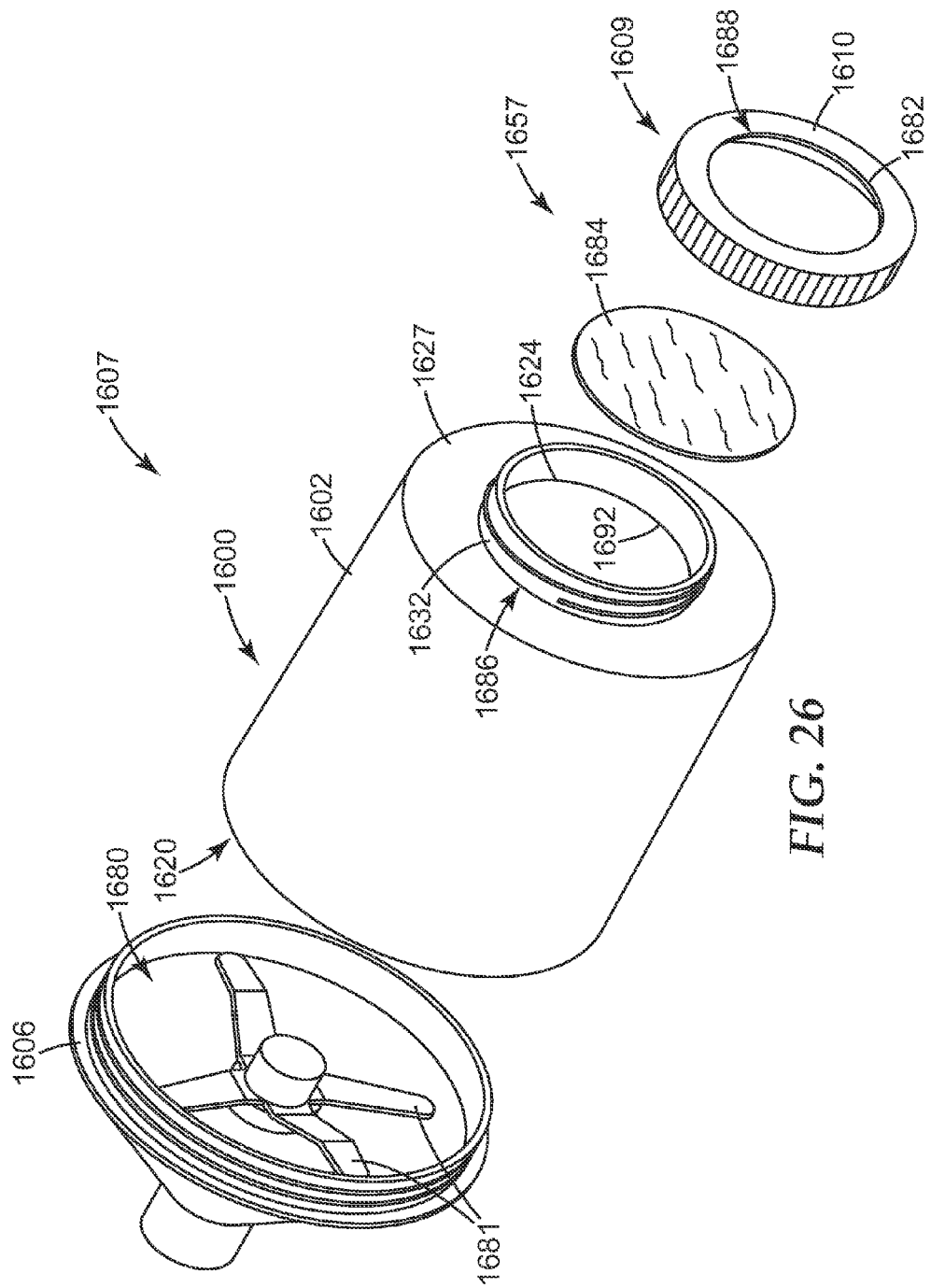
FIG. 26 is an exploded perspective view of a sample preparation and collection system according to another embodiment of the present disclosure.

In some embodiments, the sample collection system 1157 can be positioned at one end of the sample preparation and collection system 1107 (e.g., at the lid 1106 or the base 1127 of the container 1102 of the sample preparation system 1100), and means for agitating the liquid composition 1114 (and/or the filtrate 1116) can be positioned at another (e.g., opposite) end. In such embodiments, the liquid composition 1114 (and/or the filtrate 1116) can be agitated by orienting the sample preparation and collection system 1107 in a first orientation (e.g., toward blending blades), and the sample preparation and collection system 1107 can then be oriented in a second orientation (e.g., inverted) to move at least a portion of the liquid composition 1114 (or filtrate 1116) in the fluid path 1192 to the sample collection system 1157. Such an embodiment is illustrated in FIG. 26 and described in greater detail below.

As mentioned above, the collection filter 1184 can be sized and/or functionalized to collect the analyte(s) of interest. As a result, the collection filter 1184 can be adapted for specific or non-specific collection of the analyte(s) of interest. In some embodiments, the collection filter 1184 can include a depth filter. The collection filter 1184 can be formed of a variety of materials, including those listed above with respect to the filter 134 shown in FIGS. 2-3, and additionally including, but not limited to, carbon, particle-loaded materials (e.g. 3M™ EMPORE™ solid phase extraction products (3M Company, St. Paul, Minn.)), and combinations thereof. The collection filter 1184 can include a variety of filter types, including, but not limited to, depth filters, surface filters, membrane filters, or the like, or combinations thereof.

In embodiments in which the collection filter 1184 is functionalized to bind or interact with the analyte(s) of interest, the sample collected by the sample collection system 1157, and particularly by the collection filter 1184, can include substantially only the analyte(s) of interest. However, in embodiments in which the collection filter 1184 is not functionalized, and the analyte(s) of interest are collected nonspecifically (e.g., by size and/or charge), the sample collected by the collection filter 1184 may not necessarily include substantially only the analyte(s) of interest, but rather may include other material from the liquid composition 1114 from which the analyte(s) of interest can be isolated in subsequent processing steps (e.g., enrichment, incubation, inoculation, etc.).

FIGS. 19-20 illustrate a sample collection system 1257 according to another embodiment of the present disclosure. The sample collection system 1257 shares many of the same elements and features described above with reference to the illustrated embodiment of FIGS. 17-18. Accordingly, elements and features corresponding to elements and features in the illustrated embodiment of FIGS. 17-18 are provided with the same reference numerals in the 1200 series. Reference is made to the description above accompanying FIGS. 17-18 for a more complete description of the features and elements (and alternatives to such features and elements) of the embodiment illustrated in FIGS. 19-20.

The sample collection system 1257 functions similarly to the sample collection system 1157 described above. The sample collection system 1257 includes a housing 1296, an inlet 1286 and an outlet 1288. The housing 1296 includes projections or threads 1295 that are adapted to be coupled to a lid of a sample preparation system, and particularly, to projections of the lid. The housing 1296 includes a bore 1297 and an inner surface 1298. The inner surface 1298 can be coupled to a port of a lid of a sample preparation system to couple the inlet 1286 of the sample collection system 1257 to a sample preparation system and position the bore 1297 in fluid communication with a reservoir of the sample preparation system.

The housing 1296 includes a chamfered portion 1296a which can facilitate coupling of the sample collection system 1257 with other devices (e.g. a vacuum source). The bore 1297 of the housing 1296 narrows toward the outlet 1288 to form an upper portion 1297a of the bore 1297 that has a smaller diameter, and which can form a seat in which a collection filter 1284 (not shown in FIG. 20) can be positioned. As shown in FIG. 20, a plurality of channels 1293 are defined in the inner surface 1298 at the top of the housing 1296, and the housing 1296 further includes a port 1294 that defines an aperture or bore 1282 (shown in FIG. 20) which can function as the outlet 1288 of the sample collection system 1257. The channels 1283 facilitate fluid flow from the collection filter 1284 to the aperture 1282. In the embodiment illustrated in FIGS. 19-20, the sample collection system 1257 includes three diametric channels 1283 spaced equally about the central aperture 1282; however, a variety of other channel configurations suitable for facilitating fluid flow from the collection filter 1284 to the aperture 1282 can be employed without departing from the spirit and scope of the present disclosure.

The bore 1297, the channels 1293, and the aperture 1282 define at least a portion of a fluid path 1292 (shown in FIG. 20), such that the inlet 1286 can be in fluid communication with a sample preparation system. In some embodiments, negative pressure can be applied to the outlet 1288 of the of the sample collection system 1257 (e.g., by fluidly coupling at least a portion of the housing 1296 to a vacuum source). When negative pressure is applied to the outlet 1288 of the sample collection system 1257, a liquid composition can be moved into the sample collection system 1257 (or the liquid composition can be moved through a pre-filter to form a filtrate, and the filtrate can be forced through the sample collection system 1257), particularly, through the bore 1297, the collection filter 1284, the aperture 1282 and possibly, the channels 1293. As the liquid composition (or filtrate) passes through the collection filter 1284, the analyte(s) of interest can be trapped in the collection filter 1284, and the portions of the liquid composition (or filtrate) that are not trapped by the collection filter 1284 can pass through the collection filter 1284, and optionally to waste or another receptacle. The collection filter 1284 can be sized, charged and/or functionalized to collect the analyte(s) of interest.

Figure 21:
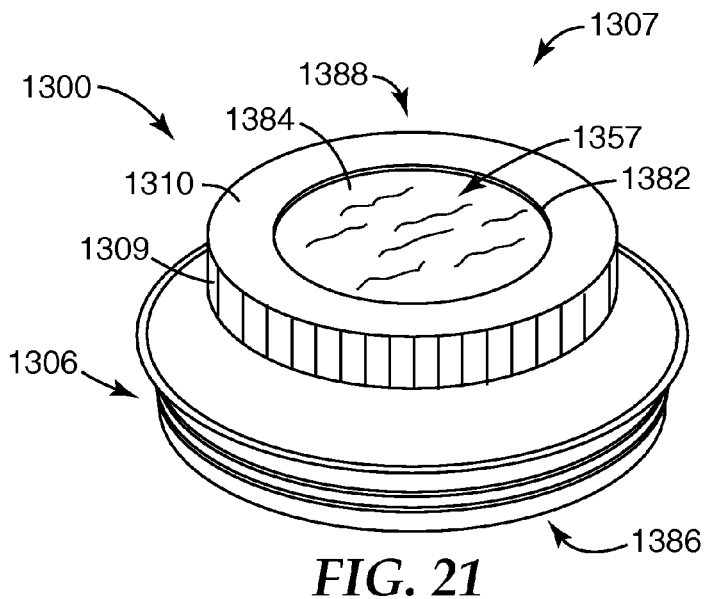
FIG. 21 is an assembled perspective view of a sample preparation and collection system according to another embodiment of the present disclosure.
Figure 22:
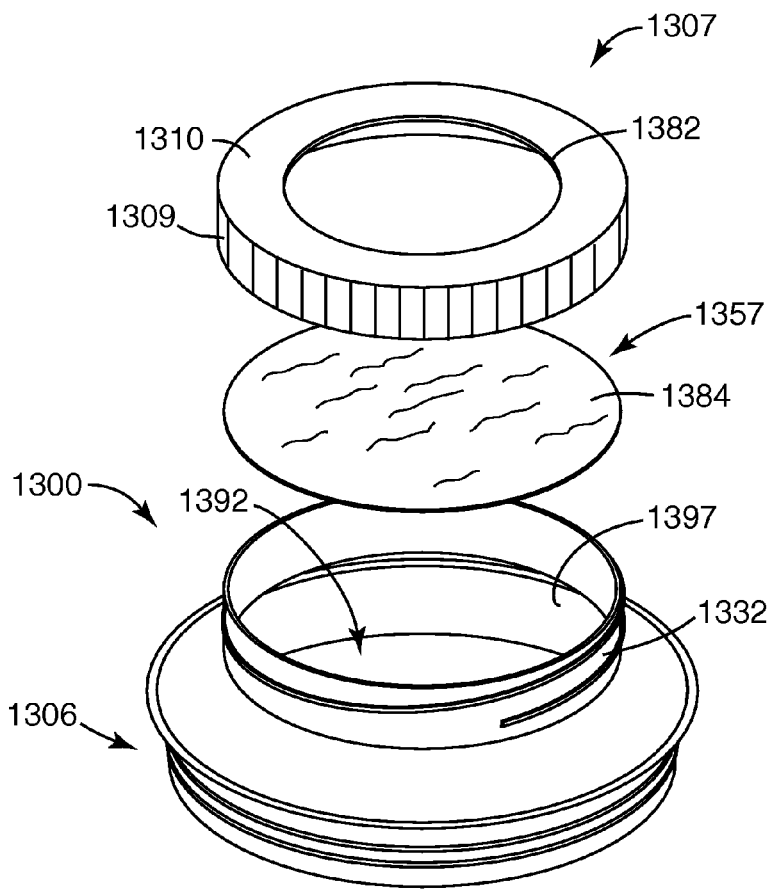
FIG. 22 is an exploded perspective view of the sample preparation and collection system of FIG. 21.

FIGS. 21-22 illustrate a sample preparation and collection system 1307 according to another embodiment of the present disclosure, the sample preparation and collection system 1307 including a sample preparation system 1300 and a sample collection system 1357. The sample preparation system 1300 share many of the same elements and features described above with reference to the illustrate embodiment of FIGS. 9-12, and the sample collection system 1357 shares many of the same elements and features described above with reference to the illustrated embodiment of FIGS. 17-18. Accordingly, elements and features corresponding to elements and features in the illustrated embodiments of FIGS. 9-12 and 17-18 are provided with the same reference numerals in the 1300 series. Reference is made to the description above accompanying FIGS. 9-12 and 17-18 for a more complete description of the features and elements (and alternatives to such features and elements) of the embodiment illustrated in FIGS. 21-22.

The sample preparation system 1300 includes a lid 1306 and a cover 1309 substantially similar to that described above with respect to FIGS. 9-12, except that the cover 1309 does not include a frangible barrier. The cover 1309 includes an upper wall 1310 and an aperture 1382 defined in the upper wall 1310. The lid 1306 includes a port 1332 that defines at least a portion of a bore 1397 that can be positioned in fluid communication with a reservoir of a sample preparation system by coupling the lid 1306 to a container and/or liner of the sample preparation system. The cover 1309 can be coupled to the lid 1306 via any of the above-described coupling means and is shown as being removably coupled to the lid 1306 via a screw-type engagement by way of example only.

The sample collection system 1357 includes a collection filter 1384 that can be coupled between the cover 1309 and an upper surface of the port 1332 of the lid 1306, as shown in FIGS. 21-22, such that the collection filter 1384 is positioned in fluid communication with the bore 1397 of the lid 1306 and a reservoir (not shown) of the sample preparation system 1300. All of the components shown in FIGS. 21-22 are considered to form a portion of the sample preparation and collection system 1307, and the cover 1309 and the lid 1306 are described as being a portion of the sample preparation system 1300 by way of example only. In some embodiments, the cover 1309 and the lid 1306 can be thought of as a portion of the sample collection system 1357 that is coupled to a sample preparation system (e.g., a container and/or a liner/deformable self-supporting receptacle), and in such embodiments, the sample collection system 1357 can define an inlet 1386 and an outlet 1388 of the sample collection system 1357.

The bore 1397 in the lid 1306 and the aperture 1382 in the cover 1309 define at least a portion of a fluid path 1392 (shown in FIG. 22), such that the inlet 1386 can be in fluid communication with a sample preparation system. In some embodiments, negative pressure can be applied to the outlet 1388 of the of the sample collection system 1357 (e.g., by fluidly coupling at least a portion of the cover 1309 and/or the lid 1306 to a vacuum source). When negative pressure is applied to the outlet 1388, a liquid composition can be moved into the bore 1397 (or the liquid composition can be moved through a pre-filter to form a filtrate, and the filtrate can be moved into the bore 1397), through in the lid 1306, the collection filter 1384, and the aperture 1382 in the cover 1309.

As the liquid composition (or filtrate) passes through the collection filter 1384, the analyte(s) of interest can be trapped in the collection filter 1384, and the portions of the liquid composition (or filtrate) that are not trapped by the collection filter 1384 can pass through the collection filter 1384, and optionally to waste or another receptacle. The collection filter 1384 can be sized, charged and/or functionalized to collect the analyte(s) of interest.

Figure 23:
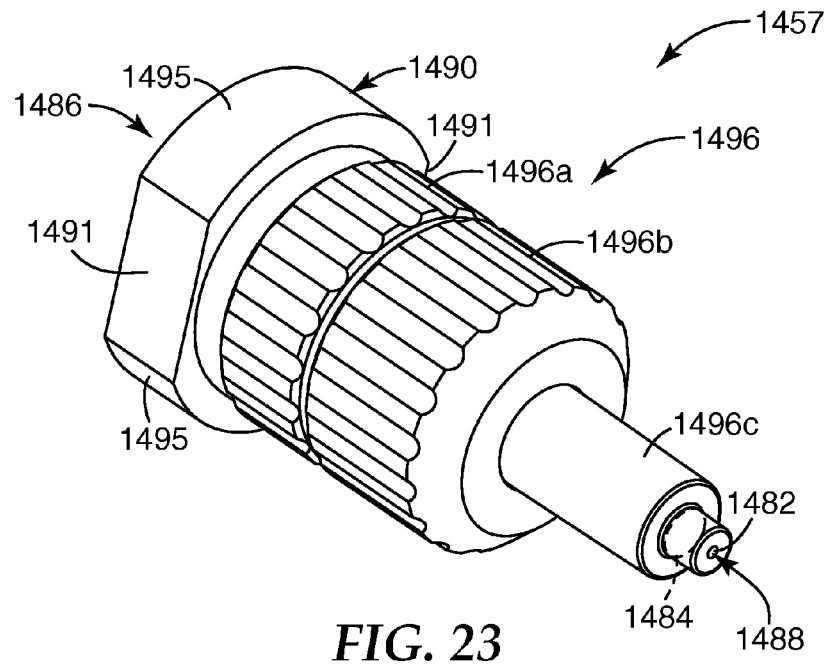
FIG. 23 is an assembled perspective view of a sample collection system according to another embodiment of the present disclosure.
Figure 24:
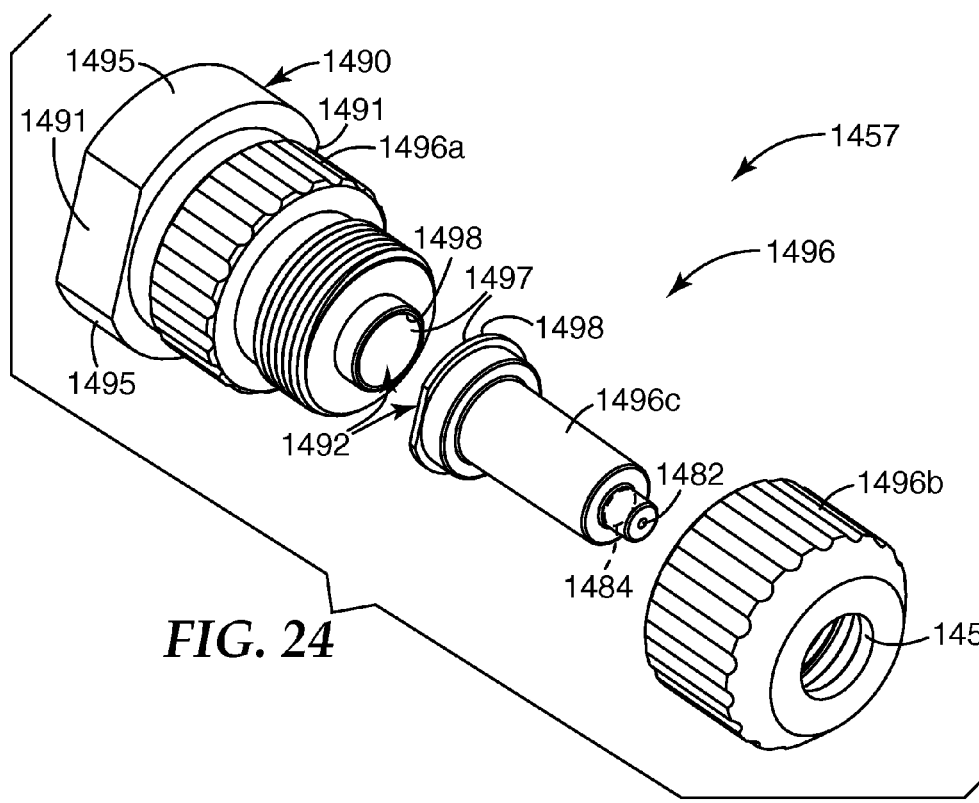
FIG. 24 is an exploded perspective view of the sample collection system of FIG. 23.

FIGS. 23-24 illustrate a sample collection system 1457 according to another embodiment of the present disclosure. The sample collection system 1457 shares many of the same elements and features described above with reference to the illustrated embodiment of FIGS. 17-18. Accordingly, elements and features corresponding to elements and features in the illustrated embodiment of FIGS. 17-18 are provided with the same reference numerals in the 1400 series. Reference is made to the description above accompanying FIGS. 17-18 for a more complete description of the features and elements (and alternatives to such features and elements) of the embodiment illustrated in FIGS. 23-24.

The sample collection system 1457 functions similarly to the sample collection system 1157 described above. The sample collection system 1457 includes a housing 1496, an inlet 1486 and an outlet 1488. The housing 1496 includes a first portion 1496*a*, a second portion 1496*b*, and a third portion 1496*c*. The first portion 1496*a*, the second portion 1496*b*, and the third portion 1496*c* can be coupled via any of the above-described coupling means but the first and second portions 1496*a* and 1496*b* are shown in FIG. 24 as being removably coupled via a screw-type engagement by way of example only. Particularly, in the embodiment illustrated in FIGS. 23-24, the second portion 1496*b* is adapted to receive at least an upper portion of the first portion 1496*a* of the housing 1496, and each of the first portion 1496*a* and the second portion 1496*b* include mating threads to allow the second portion 1496*b* to be screwed down over at least an upper portion of the first portion 1496*a* of the housing 1496. In addition, the second portion 1496*b* includes an aperture 1454 dimensioned to received a least a portion of the third portion 1496*c* of the housing 1496, as shown in FIG. 23.

The first portion 1496a of the housing 1496 includes a base 1490 with two opposing flat faces 1491 and two opposing cylindrical projections 1495. The base 1490 is adapted to be coupled to a lid of a sample preparation system, and particularly, to a port and projections of the lid. The housing 1496 includes a bore 1497 and an inner surface 1498 defined at least partially by the first and third portions 1496a and 1496c of the housing 1496. The inner surface 1498 can be coupled to a port of a lid of a sample preparation system to couple the inlet 1486 of the sample collection system 1457 to a sample preparation system and position the bore 1497 in fluid communication with a reservoir of the sample preparation system. Particularly, the base 1490 of the first portion 1496a of the housing 1496 can be dimensioned to receive the port of the lid, and the inner surface 1498 can be coupled to an outer surface of the port of the lid. In addition, the sample collection system 1457 can be moved downwardly into position over the port of the lid (e.g., with both of the cylindrical projections 1495 positioned out of contact with the projections 1139) and then rotated with respect to the lid to position the cylindrical projections 1495 under radially-inwardly projecting portions of projections on the lid (e.g., similar to the projections 1139 shown in FIG. 17), for example, to inhibit the sample collection system 1457 from being pulled from the sample preparation system.

The third portion 1496c of the housing 1496 includes a base structure similar to that of the base 1490 of the first portion 1496a, such that the base structure of the third portion 1496c can be dimensioned to receive an upper portion of the first portion 1496a of the housing 1496 and can be coupled between the first and second portions 1496a and 1496b when the second portion 1496b is coupled to the first portion 1496a. The first portion 1496a of the housing 1496 defines the inlet 1486 to the sample collection system 1457, and the third portion 1496c includes a port that defines an aperture 1482 that functions as the outlet 1488 of the sample collection system 1457. A collection filter 1484 can be positioned at the junction between the main body of the third portion 1496c and the port. As shown in FIG. 23, the collection filter 1484 is dimensioned to fit at the entrance to the port. Alternatively, however, the collection filter 1484 can be positioned at the base of the main body of the third portion 1496c and can be dimensioned more closely to the bore 1497 through the main body, rather than to that of the port. In addition, at least a portion of the inner surface 1498 in the third portion 1496c of the housing 1496 can include channels (e.g., similar to the channels 1293 described above and illustrated in FIG. 20) positioned behind (i.e., downstream) of the collection filter 1484 to facilitate fluid flow between the collection filter 1484 and the aperture 1482.

The bore 1497 and the aperture 1482 define at least a portion of a fluid path 1492 (shown in FIG. 24), such that the inlet 1486 can be in fluid communication with a sample preparation system. In some embodiments, negative pressure can be applied to the outlet 1488 of the of the sample collection system 1457 (e.g., by fluidly coupling at least a portion of the housing 1496 to a vacuum source). When negative pressure is applied to the outlet 1488 of the sample collection system 1457, a liquid composition can be moved into the sample collection system 1457 (or the liquid composition can be moved through a pre-filter to form a filtrate, and the filtrate can be forced through the sample collection system 1457), particularly, through the bore 1497, the collection filter 1484, and the aperture 1482. As the liquid composition (or filtrate) passes through the collection filter 1484, the analyte(s) of interest can be trapped in the collection filter 1484, and the portions of the liquid composition (or filtrate) that are not trapped by the collection filter 1484 can pass through the collection filter 1484, and optionally to waste or another receptacle. The collection filter 1484 can be sized, charged and/or functionalized to collect the analyte(s) of interest.

In the embodiment illustrated in FIGS. 23-24 and by way of example only, the first and second portions 1496a and 1496b are formed of metal, and particularly, of stainless steel, and the third portion 1496c is formed of a translucent polymeric material, and particularly, of polypropylene. Forming the third portion 1496c of a more transparent or translucent material can facilitate visualization of a collected sample. However, these materials are illustrated by way of example only, and one of ordinary skill in the art should understand that the first, second, and third portions 1496a, 1496b and 1496c of the housing 1496 can be can be formed of a variety of materials, including those listed above with respect to the container 102 or the collar 108. One or more of the portions 1496a, 1496b, 1496c can be formed of the same or a different material.

After the liquid composition (or filtrate) has passed through the sample collection system 1457, and the collection filter 1484 has been allowed to capture any analyte(s) of interest, the second portion 1496b of the housing 1496 can be decoupled from the first portion 1496a of the housing 1496, and the third portion 1496c comprising the collection filter 1484 and the collected sample (and any captured analyte(s) of interest) can be removed from the sample collection system 1457. The collection filter 1484 can be removed from the third portion 1496c for further processing and/or analysis, or the third portion 1496c itself can be transferred to another device for concentration, enrichment, incubation, analysis (e.g., a detection device), etc. For example, the third portion 1496c can be placed in a tube containing enrichment media, and following enrichment of the captured analyte, a sample can be added to a tube strip, which can then be positioned in automated processing equipment adapted to automatically handle the tube strip and add any necessary reagents for further processing, etc. (e.g. an enriched sample can be placed in the receiving tube ("SPR") of a VIDAS® instrument (VIDAS, bioMerieux, Hazelwood, Mo.)).

Figure 25:
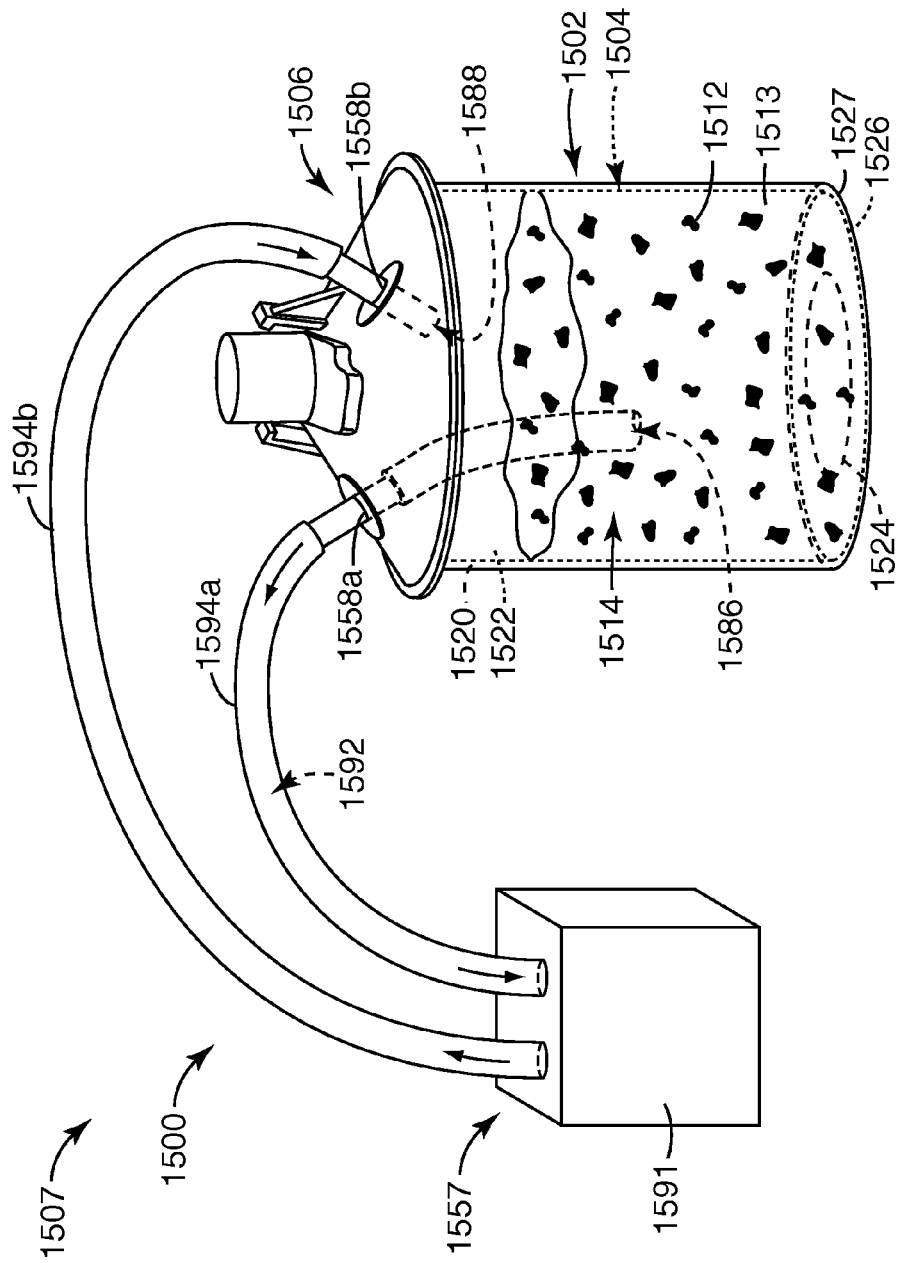
FIG. 25 is a perspective view of a sample preparation and collection system according to another embodiment of the present disclosure.

FIG. 25 illustrates a sample preparation and collection system 1507 according to another embodiment of the present disclosure. The sample preparation system 1500 shares many of the same elements and features described above with reference to the illustrated embodiments of FIGS. 2-3 and 7. Accordingly, elements and features corresponding to elements and features in the illustrated embodiments of FIGS. 2-3 and 7 are provided with the same reference numerals in the 1500 series. Reference is made to the description above accompanying FIGS. 2-3 and 7 for a more complete description of the features and elements (and alternatives to such features and elements) of the embodiment illustrated in FIG. 25.

The sample preparation and collection system 1507 includes a sample preparation system 1500 and a sample collection system 1557. The sample collection system 1557 is coupled to the sample preparation system 1500, such that the sample collection system 1557 is in fluid communication with the sample preparation system 1500, and such that a fluid path 1592 is defined at least partially by the sample preparation system 1500 and the sample collection system 1557. The fluid path 1592 allows a liquid composition, its filtrate, or a portion of the liquid composition or filtrate to be moved from the sample preparation system 1500 to the sample collection system 1557 by moving in the fluid path 1592 and not being exposed to ambience during the transfer between the sample preparation system 1500 and the sample collection system 1557.

The sample preparation system 1500 includes a container 1502 having a first reservoir 1520, a liner 1504 having a second reservoir 1522 and dimensioned to be received in the first reservoir 1520 of the container 1502, and a lid 1506. The sample preparation system 1500 can also include a collar (not shown) to further secure the components of the sample preparation system 1500 together. The second reservoir 1522 is adapted to contain a liquid composition 1514 comprising a source 1512 and a diluent 1513.

The lid 1506 includes a first aperture 1558a and a second aperture 1558b. The sample collection system 1557 includes an inlet 1586, defined by a first conduit 1594a and an outlet 1588 defined by a second conduit 1594b. The sample collection system 1557 further includes a flow cell 1591 which can include any of the above sample collection elements or features described in the embodiments above to capture the analyte(s) of interest via any of the above described bonds or interactions, including, but not limited to, magnets, immobilized molecules or moieties (e.g., antibodies and/or oligonucleotides), a collection filter that can be sized, charged and/or functionalized, etc., and combinations thereof.

The first and second conduits 1594a and 1594b are coupled to the lid 1506 of the sample preparation system 1500 via the first and second apertures 1558a and 1558b, respectively, using standard fluid connectors. At least a portion of the fluid path 1592 is defined by the first and second conduits 1594a and 1594b of the sample collection system 1557. A variety of tubing and connectors known to those of ordinary skill in the art can be used to fluidly couple the flow cell 1591 of the sample collection system 1557 to the sample preparation system 1500.

In the embodiment illustrated in FIG. 25, the liquid composition 1514 can be recirculated in the sample preparation system 1500. That is, the liquid composition 1514 can be moved from the second reservoir 1522 into the inlet 1586 of the sample collection system 1557, through the first conduit 1594a, into the flow cell 1591, and any analyte(s) of interest can be captured from the liquid composition as the liquid composition is moved through the flow cell 1591. The liquid composition (e.g., minus some captured analyte(s) of interest, if present) can then be moved into the second conduit 1594b out the outlet 1588 of the sample collection system 1557, and back into the second reservoir 1522 of the liner 1504. The liquid composition 1514 can continue to be recirculated between the sample preparation system 1500 and the sample collection system 1557 in this manner to enhance the removal and collection of any analyte(s) of interest. Furthermore, the flow cell 1591 or any portion of the fluid path 1592 can include enrichment media (e.g., coated or adsorbed onto an inner surface of a structure that defines at least a portion of the fluid path 1592).

The liquid composition 1514 can be moved between the sample preparation system 1500 and the sample collection system 1557 in a variety of ways. In some embodiments, the flow cell 1591 is coupled to or is part of a mechanical pump (e.g., a peristaltic pump), which can drive the movement of the liquid composition 1514. In some embodiments, the liner 1504 can be deformed to encourage the movement of the liquid composition 1514 from the sample preparation system 1500 and can be returned to its original shape as the liquid composition 1514 returns to the sample preparation system 1500, and so on. The liner 1504 can be deformed in any of the above-described ways, including applying positive pressure to exterior of the liner 1504 (e.g., manually by hand, manually with another device such as a plunger, or automatically with a another device), and the exterior of the liner 1504 (e.g., the base 1526 of the liner 1504) can be accessed, for example, via an aperture 1524 in a base 1527 of the container 1502. Alternatively, or in addition, negative pressure can be applied to the interior of the liner 1504, e.g., by fluidly coupling a vacuum source to the sample collection system 1557 and the second reservoir 1522 of the liner 1504. The vacuum source can be any of those described above, including, but not limited to, mechanical pumps, manual devices (e.g., a syringe-plunger combination), etc., and combinations thereof.

The sample preparation and collection system 1507 can further include a pre-filter (not shown) similar to any of the above-described filters (e.g., one or more of filters 134, 234, 334, etc.) positioned in the fluid path 1592. For example, one or more filters (e.g., similar to the filter 134 of FIGS. 2-3, a planar filter, a foam, a sponge, etc., and combinations thereof) can be dimensioned to be coupled to or within the first conduit 1594a at a variety of locations, including the inlet end, the outlet end, or at some location between the inlet and the outlet of the first conduit 1594a. By way of further example, a filter substantially similar to that of the filter 234 or the filter 534 can be positioned in the second reservoir 1522, such that the source 1512 is contained by the filter, and the filtrate can be positioned outside of (e.g., and in fluid communication with), the filter in the second reservoir 1522 to be recirculated.

In the embodiment illustrated in FIG. 25, the flow cell 1591 includes one or more magnets (not shown) which can function similarly to the magnets 993 described above and illustrated in FIG. 15 (e.g., to attract functionalized paramagnetic beads). The liquid composition 1514 can come into direct contact with the magnets and/or magnetic beads in the flow cell 1591, or the magnets can be positioned inside some type of capsule, similar to the capsule 990 described above and illustrated in FIG. 15.

FIG. 26 illustrates a sample preparation and collection system 1607 according to another embodiment of the present disclosure. The sample preparation and collection system 1607 includes a sample preparation system 1600 and a sample collection system 1657. The sample preparation system 1600 shares many of the same elements and features described above with reference to the illustrated embodiments of FIGS. 2-3 and 7; and the sample collection system 1657 shares many of the same elements and features described above with reference to the illustrated embodiment of FIGS. 21-22. Accordingly, elements and features corresponding to elements and features in the illustrated embodiments of FIGS. 2-3, 7, 21 and 22 are provided with the same reference numerals in the 1600 series. Reference is made to the description above accompanying FIGS. 2-3, 7, 21 and 22 for a more complete description of the features and elements (and alternatives to such features and elements) of the embodiment illustrated in FIG. 26.

The sample collection system 1657 is coupled to the sample preparation system 1600, such that the sample collection system 1657 is in fluid communication with the sample preparation system 1600, and such that a fluid path 1692 is defined at least partially by the sample preparation system 1600 and the sample collection system 1657. The fluid path 1692 allows a liquid composition, its filtrate, or a portion of the liquid composition or filtrate to be moved from the sample preparation system 1600 to the sample collection system 1657 by moving in the fluid path 1692 without necessarily being exposed to ambience during the transfer between the sample preparation system 1600 and the sample collection system 1657.

As shown in FIG. 26, the sample preparation system 1600 includes a lid 1606 and a container 1602 that defines a reservoir 1620. The sample preparation and collection system 1607 further includes an agitation system 1680 coupled to the lid 1606 of the sample preparation system and positioned in the fluid path 1692 and in fluid communication with the reservoir 1620 when the lid 1606 is coupled to the container 1602. The agitation system 1680 shown in FIG. 26 includes one or more blades 1681 rotatable about an axis and positioned to agitate (e.g., blend) a liquid composition in the sample preparation and collection system 1607 (e.g., in the container 1602) when the lid 1606 is coupled to the container 1602. In some embodiments, the agitation system 1680 can be adapted to be connected to a power source or can include a power source. In some embodiments, the agitation system 1680 can be adapted to be driven by an external drive (e.g., an external motor, rotor, etc. to which the agitation system 1680 can be coupled to cause the blades to rotate about a central axis and into contact with the liquid composition). The blades 1681 are illustrated by way of example only; however, it should be understood that any means for performing any of the above-described agitation methods can be employed in the agitation system 1680 instead of or in addition to the blades 1681. By way of example only, the agitation system 1680 can include a blending device similar to the blending device of U.S. Pat. Nos. D532,253, 6,338,569, 6,854,875, 7,147,365, 7,168,845, and 7,309,156, each of which is incorporated herein by reference.

The container 1602 includes a base 1627 and an aperture 1624 formed therein. In some embodiments, as shown in FIG. 26, the sample collection system 1657 can be coupled to the container 1602 via the aperture 1624. Particularly, the sample collection system 1657 includes or is coupled to a port 1632 that is in fluid communication with the interior of the container 1602 via the aperture 1624. The sample collection system 1657 further includes a collection filter 1684 adapted to be coupled to the port 1632. The collection filter 1684 can be secured to the port 1632 (and therefore to the container 1602) with a cover 1609. The cover 1609 includes an upper wall 1610 and an aperture 1682 defined in the upper wall 1610. The cover 1609 can be coupled to the port 1632 via any of the above-described coupling means and is shown as being removably coupled to the port 1632 via a screw-type engagement by way of example only.

The collection filter 1684 can be coupled between the cover 1609 and an upper surface of the port 1632 of the lid 1606, such that the collection filter 1684 is positioned in fluid communication with the reservoir 1620 of the sample preparation system 1600. The cover 1609, the collection filter 1684 and the port 1632 are shown and described as being a part of the sample collection system 1657; however, in some embodiments, the sample collection system 1657 can also include a lower portion of the container 1602, the aperture 1624 and the base 1627, and in some embodiments, the sample collection system 1657 can include the collection filter 1684 and the other components can form a portion of the sample preparation system 1600. Such categorization of components or parts is not critical, and all components shown in FIG. 26 can instead form a portion of the sample preparation and collection system 1607. In the embodiment illustrated in FIG. 26, the sample collection system 1657 includes an inlet 1686 and an outlet 1688 of the sample collection system 1357.

The port 1632 coupled to or forming the base 1627 of the container 1602 and the aperture 1682 in the cover 1609 define at least a portion of a fluid path 1692, such that the inlet 1686 can be in fluid communication with the sample preparation system 1600. In some embodiments, negative pressure can be applied to the outlet 1688 of the of the sample collection system 1657 (e.g., by fluidly coupling at least a portion of the cover 1609 to a vacuum source). When negative pressure is applied to the outlet 1688, a liquid composition can be moved into the port 1632 (or the liquid composition can be moved through a pre-filter to form a filtrate, either prior to or in the port 1632), through the collection filter 1684, and the aperture 1682 in the cover 1609. As the liquid composition (or filtrate) passes through the collection filter 1684, the analyte(s) of interest can be trapped in the collection filter 1684, and the portions of the liquid composition (or filtrate) that are not trapped by the collection filter 1684 can pass through the collection filter 184, and optionally to waste or another receptacle. The collection filter 1684 can be sized, charged and/or functionalized to collect the analyte(s) of interest.

As mentioned above, the sample collection system 1657 shown in FIG. 26 is similar to that of the sample collection system 1357 of FIGS. 21 and 22; however, it should be understood that any of the sample collection systems 857, 957, 1057, 1157, 1257, 1357, 1457 and 1557 described above can be used in the sample preparation and collection system 1607 instead.

In use, a liquid composition can be positioned in the reservoir 1620 of the container 1602. In some embodiments, the sample preparation and collection system 1607, or a portion thereof, can be oriented in a first orientation in which the liquid composition is directed toward the agitation system 1680 for agitation (e.g., oriented so that the agitation system 1680 is at the bottom of the sample preparation and collection system 1607). After the liquid composition has been agitated, the sample preparation and collection system 1607, or a portion thereof, can be oriented in a second orientation (e.g., inverted) in which the liquid composition is directed toward the sample collection system 1657 for capture of one or more analytes of interest (e.g., oriented so that the sample collection system 1657 is at the bottom of the sample preparation and collection system 1607). Said another way, the liquid composition can be moved in the fluid path 1692 to the agitation system 1680 for agitation without being exposed to ambience, and the liquid composition can then be moved in the fluid path 1692 to the sample collection system 1657 without being exposed to ambience.

The sample preparation and collection system 1607 of FIG. 26 is shown as not including a filter for pre-filtering the liquid composition prior to collection, or a liner, but it should be understood that such features can be employed in the sample preparation and collection system 1607 similar to how such features are employed in various embodiments described above. For example, in some embodiments, the agitation system 1680 can instead be formed in a base of a liner, and the sample collection system 1657 can be employed in the lid 1606 (e.g., such as the case for the sample collection system 1357 described above and illustrated in FIGS. 21 and 22). In such embodiments, the lid 1606 can be adapted to be coupled to the liner, and following use of the sample preparation and collection system 1607, the lid 1606, the liner, the agitation system 1680 and/or portions of the sample collection system 1657 that are not used in subsequent processing steps can be discarded.

In the embodiment illustrated in FIG. 26, the agitation system 1680 is coupled to the lid 1606 and the sample collection system 1657 is coupled to the base 1627 of the container 1602. However, it should be understood that the agitation system 1680 can instead be coupled to the base 1627 of the container 1602 (or a base of a liner) and the sample collection system 1657 can be coupled to the lid 1606. Furthermore, in some embodiments, the agitation system 1680 and the sample collection system 1657 can be coupled to the same end of the sample preparation and collection system 1607. For example, in some embodiments, the agitation system 1680 can be coupled to the lid 1606 (or the container 1602), as shown in FIG. 26, and the sample collection system 1657 can also be coupled to the lid 1606 (or the container 1602). In such embodiments, the sample preparation and collection system 1607 can be oriented in one orientation for agitation and collection. Additionally, a liner can be employed in embodiments in which both the agitation system 1680 and the sample collection system 1657 are coupled to the lid 1606.

In some embodiments, such as the embodiment illustrated in FIG. 26, the agitation system 1680 can be positioned in a portion of the sample preparation and collection system 1607 that is removable (e.g., the lid 1606 or a removable portion of the container 1602), such that the agitation system 1680 is movable into and out of the fluid path 1692 and into and out of fluid communication with the reservoir 1620 and/or the liquid composition. However, in some embodiments, reduced risk of contamination can result when the liquid composition is not exposed to ambience throughout the processing steps (e.g., agitating, and/or pre-filtering, etc.) and the collecting step. However, in some embodiments, the sample preparation and collection system 1607 can be opened following collection in order to retrieve the sample collection system 1657, or a portion thereof, for further processing.

In some embodiments, the sample preparation and collection system 1607 (e.g., the sample preparation system 1600) can include a first lid 1606, as shown in FIG. 26, and a second lid, for example, that can resemble the lid 106 shown in FIG. 2. In such embodiments, after the liquid composition has been agitated, the sample preparation and collection system 1607 can be inverted (e.g., the liquid composition can be moved away from the agitation system 1680), the lid 1606 can be removed, and the second lid can be coupled to the container 1602 (and/or a liner). In some embodiments, the container 1602 includes a first removable portion (e.g., that includes the base 1627) that includes the agitation system 1680 and a second removable portion that can be coupled to the remainder of the container 1602 after agitation and after removal of the first removable portion. Similarly, in some embodiments, the sample collection system 1657 can be coupled to a removable portion (e.g., a lid, base, etc.) of the sample preparation and collection system 1607 (e.g., the sample preparation system 1600). While such replaceable components can be employed to accomplish the various processing and collection steps, embodiments that do not require opening of the fluid path 1692 can provide reduced risk of contamination.

Any of the sample collection systems 857, 957, 1057, 1157, 1257, 1357, 1457, 1557, and 1657 described above can include multiple pre-filtering and/or multiple collection filtering steps. For example, a liquid composition can be filtered to form a first filtrate. The first filtrate can then be filtered again to form a second filtrate. This could be accomplished, for example, using the filters 234 and 234' described above and illustrated in FIG. 4. The second filtrate can then be moved into a sample collection system, and through a first collection filter that includes a first functionality to collect a first analyte of interest. The portion of the second filtrate that passes through the first collection filter can then be passed through a second collection filter that includes a second functionality to collect a second analyte of interest. In this example, the first and second pre-filters and the first and second collection filters are positioned in series. However, one or both of the pre-filters and the collection filters can be used in parallel instead. For example, the second collection filter can be located in a fluid path at the same location as the first collection filter such that a liquid composition or a filtrate can pass through both collection filters at the same time. A variety of other configurations and numbers of pre-filters and collection filters can be conceived of, based on the embodiments described herein and illustrated in the accompanying drawings.

In addition, a sample collection system of the present disclosure (e.g., any of sample collection systems 857, 957, 1057, 1157, 1257, 1357, 1457, 1557, and 1657 described above) can be employed in a portion of a sample preparation system (e.g., any of the sample preparation systems 100, 200, 300, 400, 500, 600, 700, 800, 900, 1000, 1100, 1300, 1500, and 1600 described above) that is movable between a first position in which the liquid composition is in fluid communication with the sample collection system and a second position in which the liquid composition is not in fluid communication with the sample collection system. For example, in some embodiments, the sample collection system can be employed in a lid (e.g., any of the lids 106, 206, 306, 406, 506, 606, 706, 806, 906, 1106, 1306, 1506, and 1606 described above) that is movable between a first position with respect to a container (e.g., any of the containers 102, 202, 402, 502, 1102, 1502, and 1602 described above) and/or a liner (e.g., any of the liners 104, 404, 504, 604, 1104, 1504) in which the sample collection system is positioned to collected any analyte(s) of interest from the liquid composition, and a second position with respect to the container and/or the liner in which the sample collection system is positioned to elute any collected analyte(s) of interest out of the sample preparation system. By way of example only, the sample collection system can be employed in a lid of a sample preparation system, and the lid can be rotatable between a first position and a second position with respect to the container and/or the liner.

Furthermore, any of the above sample collection systems 857, 957, 1057, 1157, 1257, 1357, 1457, 1557, and 1657 can include more than one type of capture or collection, e.g., nonspecific and specific capture can both be utilized in one sample collection system.

Any of the sample preparation and collection systems 807, 907, 1007, 1107, 1207, 1307, 1407, 1507, and 1607 comprising any of the sample preparation systems 100, 200, 300, 400, 500, 600, 700, 800, 900, 1000, 1100, 1300, 1500, and 1600 and any of the sample collection systems 857, 957, 1057, 1157, 1257, 1357, 1457, 1557, and 1657 described herein, and portions and combinations thereof, can be used together to prepare and collect samples by generally following the sample preparation and collection method 10 described above and illustrated in FIG. 1. One of ordinary skill in the art will also understand that various components from one sample preparation system described herein can be used in combination with other components from another sample preparation system described herein, without departing from the spirit and scope of the present disclosure. For example, the receptacle 604 can be used in place of the liner 1104 in the sample preparation system 1100. Similarly, various components from one sample preparation and collection system can be used in combination with other components from another sample preparation and collection system, and various components from one sample collection system can be used in combination with other components from another sample collection system. For example, any of the above-described sample collection systems can be coupled to a lid of a sample preparation system and/or to a base of the sample preparation system.

An exemplary method will now be described in detail using the sample preparation system 600 of FIGS. 9-12, the sample collection system 1057 of FIG. 16, and the sample collection system 1357 of FIGS. 21-22. In the following example, however, the sample collection system 1057 will be assumed to be coupled to the base 626 of the receptacle 604, rather than to the cover 609. The base 626 of the receptacle 604 will be assumed to be removable and replaceable (e.g., by a base 626 that does not include the sample collection system 1057), if necessary.

A source can be positioned within the filter 634, the filter 634 can be coupled to the lid 606 (which is coupled to the receptacle 604), and a diluent can be poured through the filter 634 to form a liquid composition in the reservoir 622 comprising the source and the diluent. Nutrients for one or more bacteria of interest can be coated or adsorbed onto an inner surface of the receptacle 604, and can become hydrated when the diluent is added to the reservoir 622.

The liquid composition can be agitated to mix the source and the diluent (including the rehydrated nutrients) and to dissolve, disperse, suspend and/or emulsify the source in the diluent. Agitation may include any of the above-described processes, and for example, can be linear, in a circular orbit, an elliptical orbit, a random orbit, a combination thereof, or of other means to ensure effective and efficient mixing of the source and the diluent. The sample preparation system 600 may be further secured by clamping or other means during agitation to minimize spillage and/or loss of the liquid composition.

In some embodiments, the liquid composition can be agitated by coupling the sample preparation system 600 to a Burell Model 75 Wrist Action Shaker (Burrell Scientific, Pittsburgh, Pa.), and agitating the sample preparation system 600 at a frequency of 10 to 2000 cycles/minute, and in some embodiments, at a frequency of 200 to 500 cycles/minute for a selected duration of time. In some embodiments, the sample preparation system 600 can be mounted at a distance from the shaker arm from between 5 cm and 50 cm, and in some embodiments, between 10 cm and 20 cm. In some embodiments, the sample preparation system 600 can inscribe an arc of 5 degrees to 30 degrees, and in some embodiments, between 15 degrees and 20 degrees. The liquid composition may be agitated for at least 10 seconds, in some embodiments, at least 15 seconds, in some embodiments, at least 30 seconds, in some embodiments, at least 40 seconds, and in some embodiments, at least 60 seconds. In some embodiments, the liquid composition can be agitated for at most 15 minutes, in some embodiments, at most 10 minutes, in some embodiments, at most 5 minutes, and in some embodiments, at most 3 minutes.

In some embodiments, the liquid composition can be vortexed in a VX-2500 Multi-Tube Vortexer (VWR Scientific Products, West Chester, Pa.) at an agitation frequency of 200 to 5000 rpm, and in some embodiments, of 1000 to 3000 rpm for a selected duration of time. The vortex orbit can be linear, circular, elliptical, random, or a combination thereof. In some embodiments, the orbit is between 0.25 cm and 5 cm, and in some embodiments, between 1 cm and 3 cm.

A plurality of sample preparation systems can be agitated simultaneously, by being placed on a plate, an arm or other device, and secured by gravity, clamping or other means for subsequent agitation. For example, in some embodiments, one to about fifty sample preparation systems are agitated simultaneously, and in some embodiments, about 10 to about 25 sample preparation systems are agitated simultaneously on a single agitation device or with multiple agitation devices.

In some embodiments, the liquid composition can be agitated by the addition of a mechanical stirrer having a shaft and stirring blades, which may be inserted through any of the possible apertures described above that are not occupied. In some embodiments, the liquid composition can be agitated by employing a lid (e.g., lid 1106) or a base (e.g., base 1127 of container 1102) that includes means for agitating (e.g., blending blades); coupling such a lid or base to the container (e.g., container 1102) and/or liner (e.g., liner 1104, if employed); orienting the sample preparation and collection system (e.g., 1107) toward the means for agitating; and operating the means for agitating. In some embodiments, agitation of the liquid composition can be accomplished with steel ball bearings, magnetic stirring bars, blades, and other means to assist in breaking up and/or dispersing the source in the diluent to release any analyte(s) of interest from the source. The agitation methods described above are included by way of example only and are not intended to be limiting. One of ordinary skill in the art will understand that other similar agitation methods can be employed.

The filter 634 can act as a pre-filter (and need not include the lower portion 635b of the frame 635) to catch relatively large insoluble matter and to filter the liquid composition to form a filtrate that is positioned in the reservoir 622 below the filter 634. The filtrate can then be allowed to interact with the sample collection system 1057, and particularly, with the antibodies 1094 that are immobilized at the base 626 of the receptacle 604. In some embodiments, the antibodies 1094 can be immobilized on a removable strip that is coupled to an inner surface of the base 626 of the receptacle 604, and the removable strip, after being allowed to interact with the antibodies 1094, can be removed and transferred to another device for subsequent processing.

After the filtrate has been formed in the reservoir 622 of the receptacle 604, the cover 609 can be coupled to the lid 606 to close the sample preparation system 600 and to allow the filtrate to interact with the antibodies 1094. The sample preparation system 600 can be transferred to an incubation environment to further enrich the filtrate. Prior to or after incubation, the filter assembly 633 can be removed from the reservoir 622; however, the filter assembly 633 need not be removed.

In some embodiments, after the bacteria of interest have been captured by the antibodies 1094, the bacteria can be further processed. For example, the filter assembly 633 and any uncaptured filtrate can be removed from the reservoir 622 of the receptacle 604, such that all that remains in the reservoir 622 are the captured bacteria of interest (alternatively, the base 626 or a removable strip in the base 626 can be removed and positioned in a new sample preparation system 600). A lysing agent and, optionally, an elution solution (e.g., a second diluent comprising one or more of these items) can then be added to the reservoir 622 to lyse the bacteria that have been captured by the antibodies 1094, and, optionally, to elute the bacteria from the antibodies 1094.

Then, the sample collection system 1357 comprising the collection filter 1384 can be coupled between the lid 606 and the cover 609 (alternatively, a new lid 606/1306 and cover 609/1309 can be coupled to the receptacle 604). The collection filter 1384 can be functionalized to capture specific nucleic acid sequences from the bacteria of interest. The filter assembly 633 (and, likely a new filter assembly 633) can be positioned in the reservoir 622 to filter any cellular debris resulting from the lysing process. A vacuum can be applied to the outlet 1388 of the sample collection system 1357, the liquid composition comprising the second diluent and the lysed bacteria of interest can be forced through the filter 634 to form a filtrate, and the filtrate can be forced through the collection filter 1384 to collect the nucleic acids of interest from the bacteria of interest. As described above, positive pressure can be applied to the receptacle 604 to move the liquid composition through the filter 634 and the collection filter 1384, rather than negative pressure, using any of the above-described techniques.

The cover 609 can then be decoupled from the sample preparation system 600, and the collection filter 1384 with the captured nucleic acids of interest can be removed and transferred to another device or location for subsequent processing.

The above detailed example is included by way of example only and is not intended to be limiting. Based on the above descriptions of the sample preparation and collection method 10, and the various embodiments of the sample preparation and collection system of the present disclosure, one of skill in the art should understand the various ways in which the sample preparation and collection system of the present disclosure can be used to prepare and collect samples.

The embodiments described and exemplified above and illustrated in the figures are presented by way of example only and are not intended as a limitation upon the concepts and principles of the present invention. As such, it will be appreciated by one having ordinary skill in the art that various changes in the elements and their configuration and arrangement are possible without departing from the spirit and scope of the present invention. Various features and aspects of the invention are set forth in the following claims.

What is claimed is:

1. A system for preparing and collecting samples for analyte testing, the system comprising:
    a sample preparation system comprising:
        a freestanding container comprising a first reservoir,
        a deformable self-supporting receptacle dimensioned to be received in the first reservoir of the freestanding container and comprising a second reservoir, the second reservoir adapted to contain a liquid composition comprising a source and a diluent,
        the freestanding container including a base comprising an aperture formed therein through which the deformable self-supporting receptacle can be accessed, wherein the deformable self-supporting receptacle is freestanding;
    a sample collection system coupled to the sample preparation system, the sample collection system positioned in fluid communication with the second reservoir of the sample preparation system, the sample collection system adapted to capture an analyte of interest from the liquid composition.

2. The system of claim 1, wherein the sample preparation system further comprises a lid adapted to be coupled to at least one of the freestanding container and the deformable self-supporting receptacle, wherein the sample collection system is coupled to the lid.

3. The system of claim 1, wherein the sample collection system includes a support comprising at least one of immobilized antibodies and immobilized oligonucleotides, the support being positioned in fluid communication with the liquid composition.

4. The system of claim 1, wherein the sample collection system includes at least one magnet adapted to capture the analyte of interest.

5. The system of claim 1, wherein the sample collection system includes a collection filter adapted to collect the analyte of interest.

6. The system of claim 1, wherein the analyte of interest includes at least one of a microorganism, a parasite, a biomolecule, a chemical, a metal ion, a metal-ion-containing complex, and combinations thereof.

7. The system of claim 1, wherein the analyte of interest comprises at least one of *Salmonella* spp., *Acinetobacter* spp., *Vibrio* spp., *Listeria monocytogenes*, *Escherichia coli*, *Staphylococcus aureus*, *Clostridium perfringens*, *Campylobacter jejuni*, *Pseudomonas aeruginosa*, *Bacillus anthracis*, *Bacillus cereus*, *Clostridium difficile*, methicillin-resistant *Staphylococcus aureus*, vancomycin-resistant *Enterococcus*, Norovirus, Norwalk virus, Rotavirus, Adenovirus, and a combination thereof.

8. The system of claim 1, wherein the analyte of interest comprises at least one of staphylococcal enterotoxin, *Bacillus* diarrheal toxin, *Clostridium difficile* toxin, aflatoxin, peanut allergen, egg allergen, and a combination thereof.

9. The system of claim 1, wherein the sample preparation system further comprises enrichment media adsorbed onto an inner surface of the deformable self-supporting receptacle, the enrichment media adapted to grow at least the analyte of interest.

10. The system of claim 5, wherein the collection filter comprises at least one of nylon, PTFE, modified cellulose, fiberglass, paper, and combinations thereof.

11. The system of claim 5, wherein the collection filter is functionalized to capture a specific analyte of interest.

12. The system of claim 5, wherein the collection filter is functionalized with at least one of antibodies and oligonucleotides.

13. The system of claim 5, wherein the sample collection system further comprises a housing configured to retain the collection filter in a fluid path defined at least partially by the sample preparation system and the sample collection system.

14. The system of claim 13, wherein the sample preparation system further comprises a lid adapted to be coupled to at least one of the freestanding container and the deformable self-supporting receptacle, wherein the lid includes at least one upwardly-extending projection, and wherein the housing includes at least one projection adapted to be coupled to the at least one upwardly-extending projection of the lid.

15. The system of claim 1, wherein the sample collection system is coupled to one end of the sample preparation system, and further comprising means for agitating the liquid composition coupled to another end of the sample preparation system.

16. A method for preparing and collecting samples for analyte testing, the method comprising:
    providing a sample preparation system comprising a deformable self-supporting receptacle dimensioned to be received in a freestanding container, the freestanding container being more rigid than the deformable self-supporting receptacle, the deformable self-supporting receptacle comprising a reservoir, the freestanding container including a base comprising an aperture formed therein through which the deformable self-supporting receptacle can be accessed, wherein the deformable self-supporting receptacle is freestanding;
    providing a sample collection system coupled to the sample preparation system, the sample collection system positioned in fluid communication with the reservoir of the deformable self-supporting receptacle, the sample collection system adapted to capture an analyte of interest;
    providing a liquid composition comprising a source and a diluent;
    providing a fluid path defined at least partially by the sample preparation system and the sample collection system;
    positioning the liquid composition in the reservoir of the deformable self-supporting receptacle; and moving at least a portion of the liquid composition in the fluid path to the sample collection system.

17. The method of claim 16, further comprising capturing the analyte of interest from the liquid composition with the sample collection system to form a collected sample.

18. The method of claim 17, further comprising decoupling at least a portion of the sample collection system from the sample preparation system, the decoupled portion of the sample collection system including the collected sample.

19. The method of claim 17, wherein the sample collection system includes at least one of immobilized antibodies and immobilized oligonucleotides, and wherein capturing the analyte of interest includes binding the analyte of interest to at least one of the immobilized antibodies and immobilized oligonucleotides.

20. The method of claim 17, wherein the sample collection system includes at least one magnet, and wherein capturing the analyte of interest includes attracting the analyte of interest to the at least one magnet.

21. The method of claim 16, wherein moving at least a portion of the liquid composition includes applying pressure to the exterior of the deformable self-supporting receptacle via the aperture.

22. The method of claim 16, wherein moving at least a portion of the liquid composition in the fluid path to the sample collection system includes moving at least a portion of the liquid composition in the fluid path to the sample collection system without exposing the liquid composition to ambience during the transfer from the sample preparation system to the sample collection system.

23. The method of claim 16, wherein moving at least a portion of the liquid composition in the fluid path to the sample collection system includes recirculating the liquid composition between the sample collection system and the sample preparation system.

24. The method of claim 16, further comprising agitating the liquid composition, wherein agitating the liquid composition includes orienting the freestanding container in a first orientation and wherein moving at least a portion of the liquid composition in the fluid path to the sample collection system includes orienting the freestanding container in a second orientation.

* * * * *

UNITED STATES PATENT AND TRADEMARK OFFICE
CERTIFICATE OF CORRECTION

PATENT NO.       : 8,647,574 B2                                    Page 1 of 1
APPLICATION NO.  : 12/743252
DATED            : February 11, 2014
INVENTOR(S)      : Kurt J. Halverson et al.

It is certified that error appears in the above-identified patent and that said Letters Patent is hereby corrected as shown below:

On the Title Page

Page 2, Column 2 Item (56) (Other Publications)
Line 1, Delete ""Usefullness" and insert -- "Usefulness --, therefor.
Line 11-12, Delete "Bactheriological" and insert -- Bacteriological --, therefor.

Page 3, Column 2 Item (56) (Other Publications)
Line 2, Delete "Fournal" and insert -- Journal --, therefor.

In the Specification

Column 5
Line 63, Delete "Micrococaceae," and insert -- Micrococcaceae, --, therefor.

Column 9
Line 35-36, Delete "sulphamethazine," and insert -- sulfamethazine, --, therefor.
Line 37, Delete "sulphadiazine," and insert -- sulfadiazine, --, therefor.

Column 31
Line 51, Delete "MAGNABINDO" and insert -- MAGNABIND® --, therefor.
Line 57, Delete "steptavidin," and insert -- streptavidin, --, therefor.

Column 40
Line 66, Delete "received a least" and insert -- receive at least --, therefor.

Column 49
Line 30, Delete "Burell" and insert -- Burrell --, therefor.

Signed and Sealed this
Seventeenth Day of June, 2014

Michelle K. Lee
*Deputy Director of the United States Patent and Trademark Office*